United States Patent
Ludwig

(10) Patent No.: US 9,441,308 B2
(45) Date of Patent: Sep. 13, 2016

(54) THREE-DIMENSIONAL MICROFLUIDIC MICRO-DROPLET ARRAYS FOR ELECTRONIC INTEGRATED CIRCUIT AND COMPONENT COOLING, ENERGY-HARVESTING, CHEMICAL AND BIOCHEMICAL MICROREACTORS, MINIATURE BIOREACTORS, AND OTHER APPLICATIONS

(71) Applicant: Lester F. Ludwig, San Antonio, TX (US)

(72) Inventor: Lester F. Ludwig, San Antonio, TX (US)

(73) Assignee: Lester F. Ludwig, San Antonio, TX (US)

( * ) Notice: Subject to any disclaimer, the term of this patent is extended or adjusted under 35 U.S.C. 154(b) by 619 days.

(21) Appl. No.: 13/770,934

(22) Filed: Feb. 19, 2013

(65) Prior Publication Data

US 2013/0213812 A1   Aug. 22, 2013

Related U.S. Application Data

(60) Provisional application No. 61/599,643, filed on Feb. 16, 2012.

(51) Int. Cl.

| | |
|---|---|
| *B01L 7/00* | (2006.01) |
| *C25B 9/06* | (2006.01) |
| *B01L 3/00* | (2006.01) |
| *H01L 23/473* | (2006.01) |
| *H01L 23/38* | (2006.01) |
| *F28D 15/00* | (2006.01) |

(52) U.S. Cl.
CPC ............ *C25B 9/06* (2013.01); *B01L 3/502792* (2013.01); *B01L 7/525* (2013.01); *H01L 23/38* (2013.01); *H01L 23/473* (2013.01); *B01L 2300/0874* (2013.01); *B01L 2300/185* (2013.01); *B01L 2300/1822* (2013.01); *B01L 2300/1827* (2013.01); *B01L 2300/1883* (2013.01); *B01L 2300/1894* (2013.01); *B01L 2400/0427* (2013.01); *F28D 15/00* (2013.01); *F28F 2250/08* (2013.01); *F28F 2260/02* (2013.01); *H01L 2924/0002* (2013.01)

(58) Field of Classification Search
None
See application file for complete search history.

(56) References Cited

PUBLICATIONS

J. Ding, et al., "Scheduling of Microfluidic Operations for Reconfigurable Two-Dimensional Electrowetting Arrays" IEEE Transactions on Computer-Aided Design of Integrated Circuits and Systems, vol. 20, No. 12, Dec. 2001, p. 1463-1468.*
V. K. Pamula, et al. "Cooling of integrated circuits using droplet-based microfluidics" Proceedings of the 13th ACM Great Lakes Symposium on VLSI, AMC, New York, NY: 2003, p. 84-87.*

* cited by examiner

*Primary Examiner* — J. Christopher Ball
(74) *Attorney, Agent, or Firm* — Procopio, Cory, Hargreaves & Savitch LLP

(57) ABSTRACT

A microfluidic transport system for transporting microdroplets in three spatial dimensions. In an example arrangement, a first planar arrangement for transporting microdroplets in two spatial dimensions responsive to electric fields created by electrical operation of electrodes is fluidically connected by one or more conduits to other planar arrangement for transporting microdroplets in two spatial dimensions responsive to electric fields created by electrical operation of electrodes. Microdroplets can be transported through the one or more conduits so as to be moved among the first and second planar arrangements.

The system can be used for heat transfer, fluidic transfer, and other uses, and can be implemented within a printed circuit board, integrated circuit housing, or using materials such as metal, glass, polymer, plastic, layered materials, fibrous materials, etc. Example applications include integrated circuit cooling, energy harvesting, microfluidic systems, chemical reactors, biochemical reactors, chemical analysis arrangements, biochemical analysis arrangements, and other apparatus.

19 Claims, 63 Drawing Sheets

-PRIOR ART-

Adapted from *Adaptive Cooling of Integrated Circuits Using Digital Microfludics*
by P. Paik, K. Chakrabarty, and V. Pamula, Artech House, 2007.

-PRIOR ART-

Adapted from *Adaptive Cooling of Integrated Circuits Using Digital Microfludics*
by P. Paik, K. Chakrabarty, and V. Pamula, Artech House, 2007.

-PRIOR ART-
"Confined System"
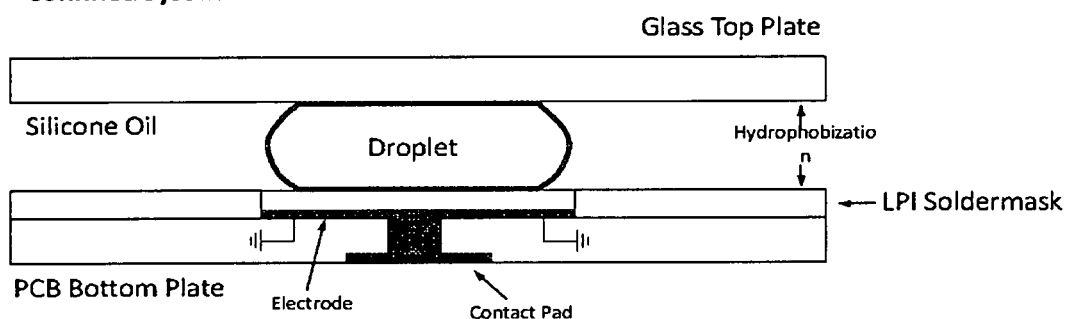
Adapted from *Adaptive Cooling of Integrated Circuits Using Digital Microfludics* by P. Paik, K. Chakrabarty, and V. Pamula, Artech House, 2007.
Figure 2
-PRIOR ART-
"Open System"
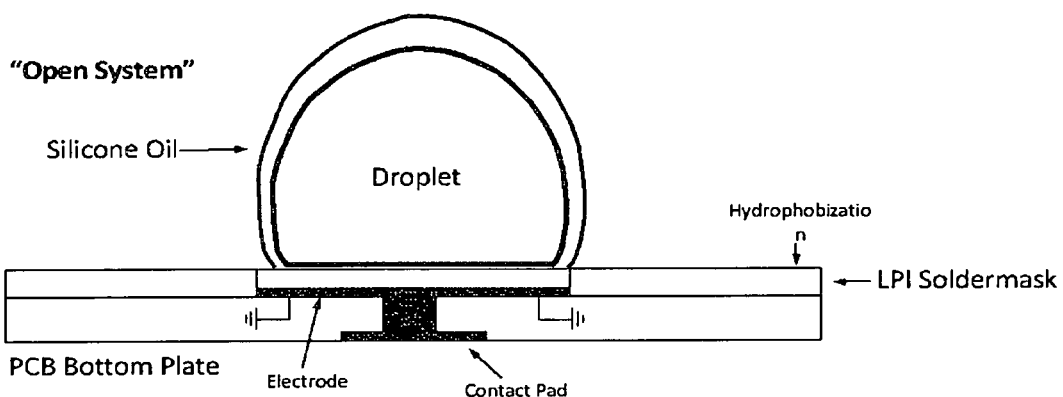
Figure 3 Adapted from *Adaptive Cooling of Integrated Circuits Using Digital Microfludics* by P. Paik, K. Chakrabarty, and V. Pamula, Artech House, 2007.

-PRIOR ART-                                    -PRIOR ART-
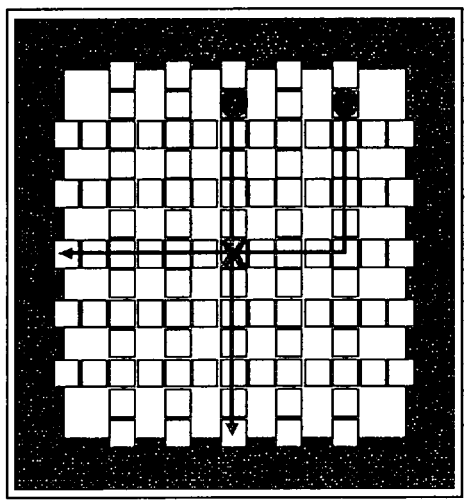   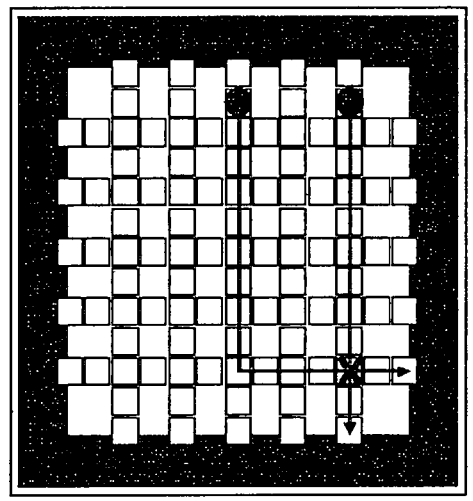
Adapted from
*Adaptive Cooling of Integrated Circuits Using Digital Microfludics*
by P. Paik, K. Chakrabarty, and V. Pamula, Artech House, 2007.
Adapted from
*Adaptive Cooling of Integrated Circuits Using Digital Microfludics*
by P. Paik, K. Chakrabarty, and V. Pamula, Artech House, 2007.
Figure 4a                                  Figure 4b

THREE-DIMENSIONAL MICROFLUIDIC MICRO-DROPLET ARRAYS FOR ELECTRONIC INTEGRATED CIRCUIT AND COMPONENT COOLING, ENERGY-HARVESTING, CHEMICAL AND BIOCHEMICAL MICROREACTORS, MINIATURE BIOREACTORS, AND OTHER APPLICATIONS

CROSS-REFERENCE TO RELATED APPLICATIONS

Pursuant to 35 U.S.C. Section 119(e), this application claims benefit of priority from Provisional U.S. Patent Application Ser. No. 61/599,643, filed Feb. 16, 2012, the contents of which are incorporated by reference in their entirety.

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND

1. Field

Aspects of the example implementations pertain to the areas of thermoelectric devices and microfluidics, and more specifically to three-dimensional microfluidic micro-droplet arrays for electronic integrated circuit and component cooling, energy-harvesting, and other applications.

2. Overview

The cooling and energy harvesting of heat-producing integrated circuits and other electronic components in computers, particularly in large high-density blade servers and data center environments, is a topic both deserving of and gaining considerable importance to commerce. Technologies addressing these problems and opportunities can be found, for example, in pending U.S. patent application Ser. No. 13/385,411 and the references therein, including chapter 1 of the text *Adaptive Cooling of Integrated Circuits Using Digital Microfludics* by P. Paik, K. Chakrabarty, and V. Pamula, published by Artech House, Inc., Norwood, Me., Artech House, 2007, ISBN 978-1-59693-138-1.

The cooling of heat-producing integrated circuits in computers by means of controlled electrowetting micro-droplet transport via microfluidic device structures has been considered in considerable detail in the above-cited text by Paik, Chakrabarty, and Pamula. In Chapter 6 of that text, those authors describe approaches to implementing microfluidic device structures for controlled electrowetting micro-droplet transport for integrated circuit cooling using Printed Circuit Boards ("PCBs").

In the afore-cited text, those authors describe first other approaches and general aspects of controlled electrowetting micro-droplet transport via microfluidic device structures. For example, FIG. 1*a*, adapted from the afore-cited text, depicts a side view representation of a microfluidic electrowetting micro-droplet transport "chip" implementation fitted over an integrated circuit package and in turn in thermal contact with an active cooling element such as a thermoelectric cooler. Additionally, FIG. 1*b*, adapted from the afore-cited text, depicts a top view representation of a number of micro-droplets being transported (via electrowetted transport) through various straight and right-angle-turn paths over a planar array of microelectrodes comprised by such a microfluidic electrowetting micro-droplet "chip." The micro-droplets are transported over the planar array of microelectrodes in tightly-controlled fashion by temporally sequencing the electric potential applied to individual microelectrodes. The micro-droplets are moved into areas of thermal contact with portions of a heat-producing integrated circuit dye, housing, packaging, heat-sink, etc., where they absorb heat and then are moved to other areas, volumes, or reservoirs where the absorbed heat can be discharged, for example by means of an active cooling element such as a thermoelectric cooler. In addition to the transport of micro-droplets, those authors describe various means of controlling the surface-area and temporal duration of micro-droplets exposure to heat sources, droplet routing strategies, and other innovations. Also useful experimental data resulting from prototypes are reported, including the fact that larger droplets with longer exposure times to heat sources perform cooling functions better than smaller droplets with shorter exposure times to heat sources.

In the afore-cited text, those authors later describe adapting the microfluidic electrowetting micro-droplet planar microelectrode array and micro-droplet transport to implementations using Printed Circuit Boards ("PCBs"). Two approaches are considered in some detail, these being the "confined system" represented in FIG. 2 and the "open system" represented in FIG. 3. In each of these systems, micro-droplets are moved into areas of thermal contact with portions of a heat-producing integrated circuit dye, housing, packaging, heat-sink, etc., where they absorb heat and then are moved (via sequencing the electric potential applied to the microelectrodes) to other areas, volumes, or reservoirs where the absorbed heat can be discharged. FIGS. 4*a* and 4*b* (each adapted from *Adaptive Cooling of Integrated Circuits Using Digital Microfluidics* by P. Paik, K. Chakrabarty, and V. Pamula, Artech House, 2007, ISBN 978-1-59693-138-1) depict example routing paths of micro-droplets over the planar microelectrode array.

However, in the afore-cited text, those authors limit themselves to planar microelectrode arrays and accordingly planar micro-droplet transport paths. For a micro-droplet exposed to heat in central areas of a microelectrode array and which must then be transported to the edges of the microelectrode array to dispense the absorbed heat, the micro-droplets can unfortunate radiate heat back into other portions of the heat-producing integrated circuits. Those authors allude to methods for minimizing the time over which unintended heat-radiation can occur by heated micro-droplets.

Further, the afore-cited text does not provide consideration to avoiding undesired electromagnetic field and electrical field effects that can interfere with adjacent high-performance electronic circuitry.

In addition to these issues and problems, the afore-cited text only considers the cooling of heat-producing integrated circuits. Energy harvesting is not considered.

Accordingly, the reciprocal properties of heat transfer and energy harvesting (via classical Peltier and Seebeck processes) are not considered, nor therefore arrangements to implement adaptive selection between cooling and energy harvesting modalities.

Additionally, the afore-cited text only considers traditional semiconductor thermoelectric elements and does not cite nor anticipate the far higher-efficiency quantum-based thermoelectric materials such as quantum well and Atvo metals. These transform classical Peltier and Seebeck processes to vastly different effects with not only radically improved performance crossing (for the first time) important application-feasibility thresholds but also, in many areas, entirely different engineering and economic tradeoffs.

SUMMARY

Example implementations of example embodiments described herein address each of the aforementioned issues of the related art, by:
Implementation of 3D micro-droplet transit structures suitable for thermal cooling and/or energy harvesting applications, and further doing so in a manner suitable for implementation in inexpensive multilayer Printed Circuit Boards ("PCBs");
Incorporating electrical-field shielding in the above 3D micro-droplet transit structures and PCB implementations to avoid undesired electromagnetic field and electrical field effects that can interfere with adjacent high-performance electronic circuitry;
Using the above 3D micro-droplet transit structures and PCB implementations to avoid undesired heat radiation by heated micro-droplets as they are transported in areas with thermal contact to the electronic component or other heat-producing element;
Using the above 3D micro-droplet transit structures to facilitate arrangements to implement adaptive selection between cooling and energy harvesting modalities.
Employing higher-efficiency quantum-based thermoelectric materials, such as quantum well and Atvo metals, so as to radically improved performance beyond important application-feasibility thresholds and access entirely different engineering and economic tradeoffs.

BRIEF DESCRIPTION OF THE DRAWINGS

The above and other aspects and features will become more apparent upon consideration of the following description of preferred embodiments taken in conjunction with the accompanying drawing figures, wherein:

FIG. 2 (adapted from *Adaptive Cooling of Integrated Circuits Using Digital Microfluidics* by P. Paik, K. Chakrabarty, and V. Pamula, Artech House, 2007, ISBN 978-1-59693-138-1) depicts a "confined system" adaptation of the microfluidic electrowetting micro-droplet planar microelectrode array and micro-droplet transport to implementations using Printed Circuit Boards ("PCBs").

FIG. 3 (adapted from *Adaptive Cooling of Integrated Circuits Using Digital Microfluidics* by P. Paik, K. Chakrabarty, and V. Pamula, Artech House, 2007, ISBN 978-1-59693-138-1) depicts an "open system" adaptation of the microfluidic electrowetting micro-droplet planar microelectrode array and micro-droplet transport to implementations using Printed Circuit Boards ("PCBs").

FIGS. 4a and 4b (each adapted from *Adaptive Cooling of Integrated Circuits Using Digital Microfludics* by P. Paik, K. Chakrabarty, and V. Pamula, Artech House, 2007, ISBN 978-1-59693-138-1) depict example routing paths of micro-droplets over the planar microelectrode array.

FIG. 5 depicts a representation of the "top" or "bottom" view of an example array of microelectrodes, each microelectrode rendered as a conductor area on a Printed Circuit Board (PCB) and provided with an associated electrically-conducting "trace" for electrically connecting the microelectrode to voltage potential control circuitry, and, interspersed between some pairs of electrodes, a physical open hole suitable for a micro-droplet to travel through.

FIG. 8 can also depict a transient situation of micro-droplet transport wherein the momentum of the micro-droplet is not suppressed (i.e., the micro-droplet is not locked into position under the leftmost microelectrode for an interval of time).

FIG. 10 can also depict a transient situation of micro-droplet transport wherein the momentum of the micro-droplet is not suppressed (i.e., the micro-droplet is not locked into position under the activated microelectrode for an interval of time).

FIG. 28 can also depict a transient situation of micro-droplet transport wherein the momentum of the micro-droplet is not suppressed (i.e., the micro-droplet is not locked into position under the activated microelectrode for an interval of time).

FIG. 30 can also depict a transient situation of micro-droplet transport wherein the momentum of the micro-droplet is not suppressed (i.e., the micro-droplet is not locked into position under the activated microelectrode for an interval of time).

FIG. 30 can also depict a transient situation of micro-droplet transport wherein the momentum of the micro-droplet is not suppressed (i.e., the micro-droplet is not locked into position under the activated microelectrode for an interval of time).

Figure 33:
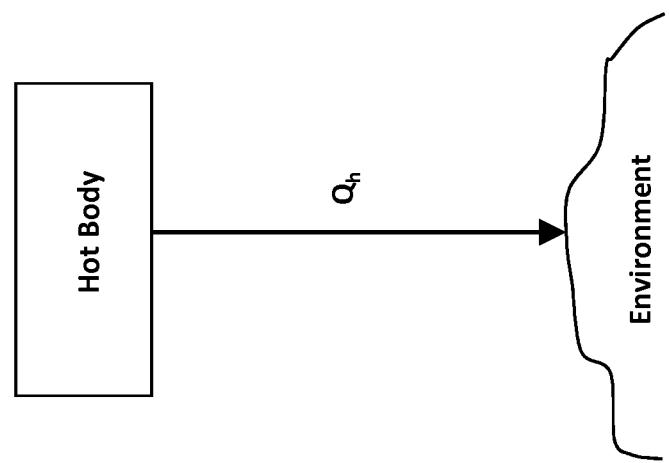
FIG. 33 depicts a general thermodynamics passive heat transfer process from a hot body to a broader environment.
Figure 35A:
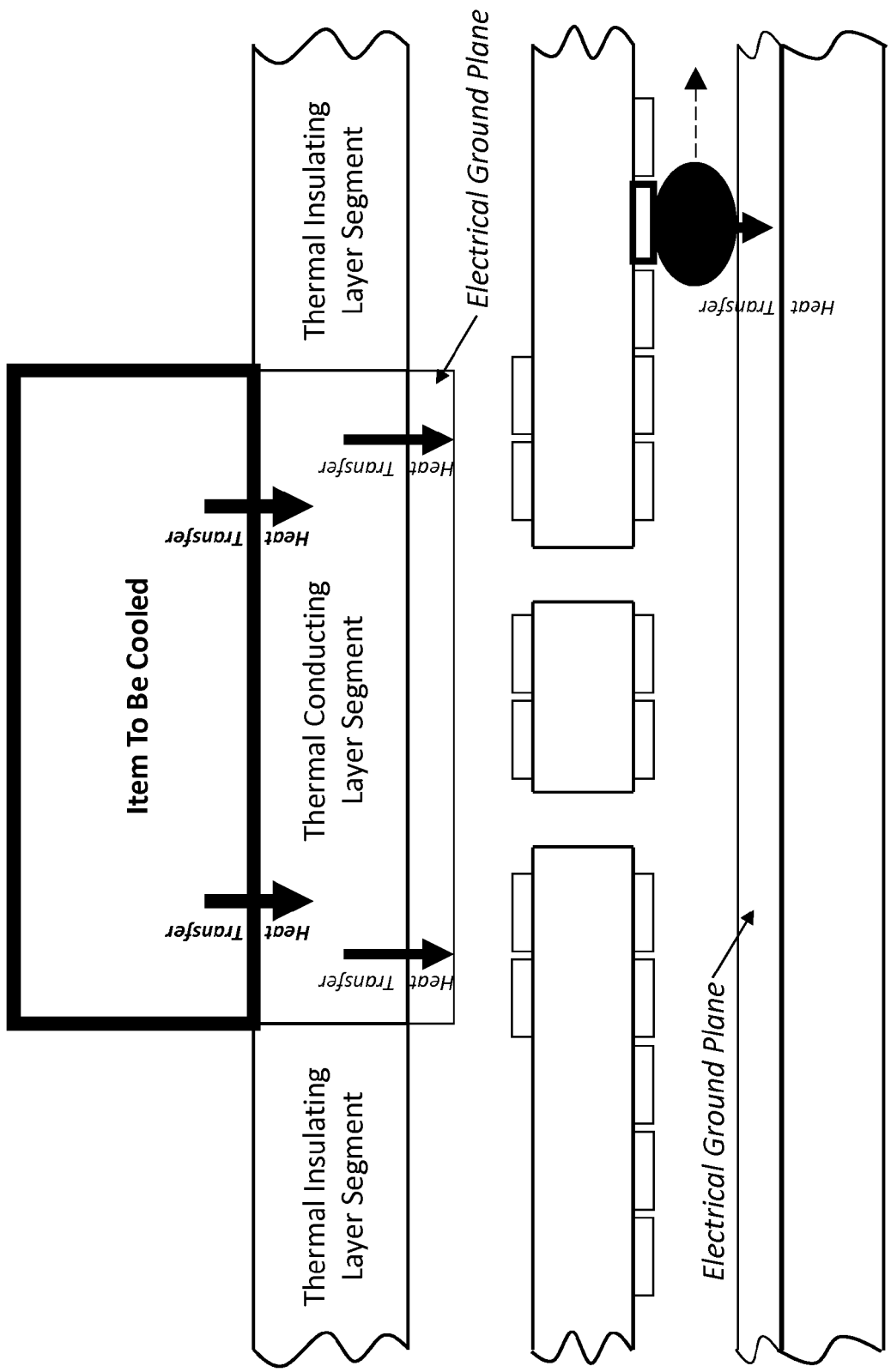
FIG. 35a depicts a representation of heat transfer from the previously heated micro-droplet to the electrical ground plane.
Figure 35B:
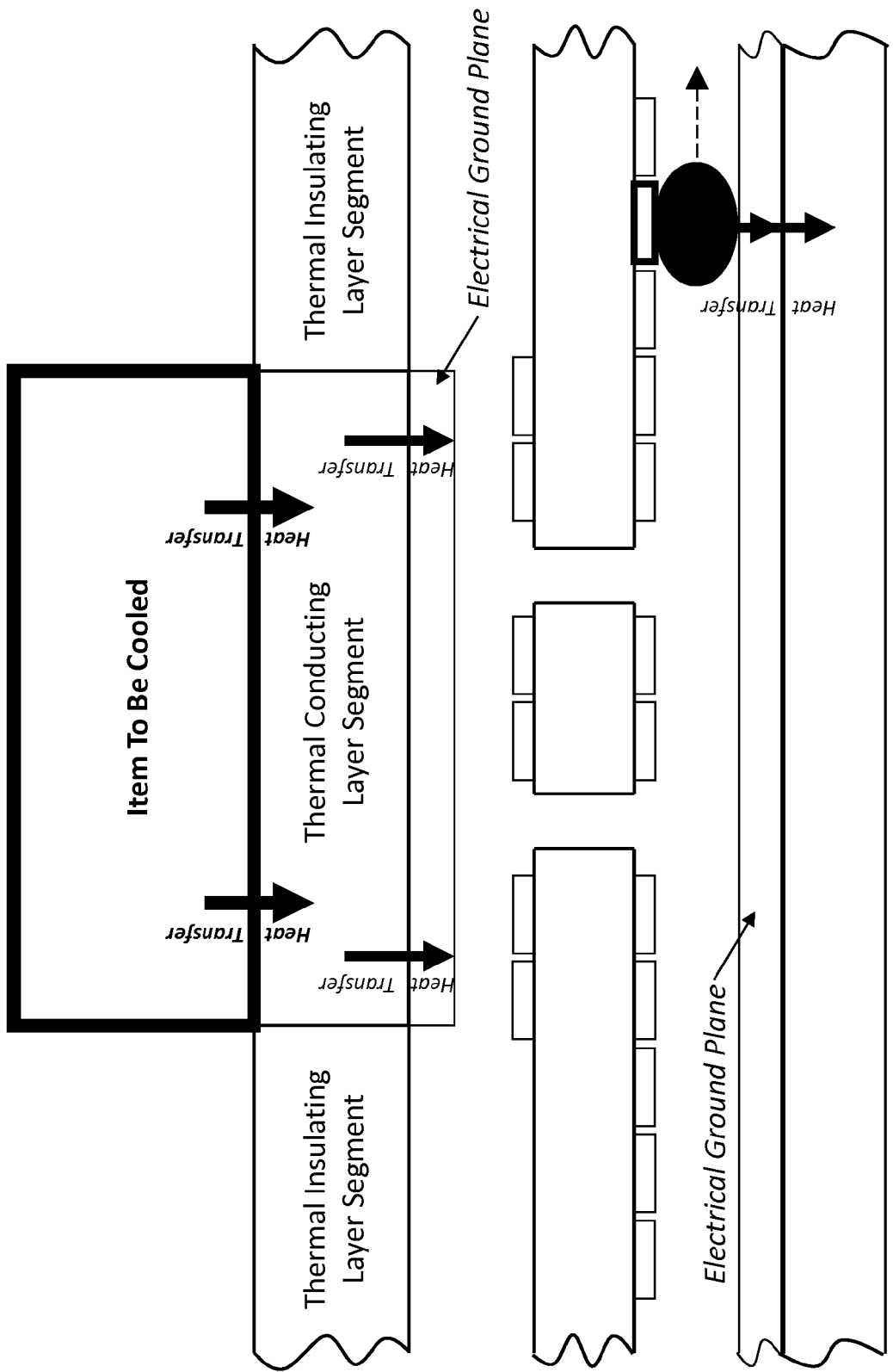
FIG. 35b depicts a representation of heat transfer from the previously heated micro-droplet to the electrical ground plane and further into the material joined to the electrical ground plane.
Figure 35C:
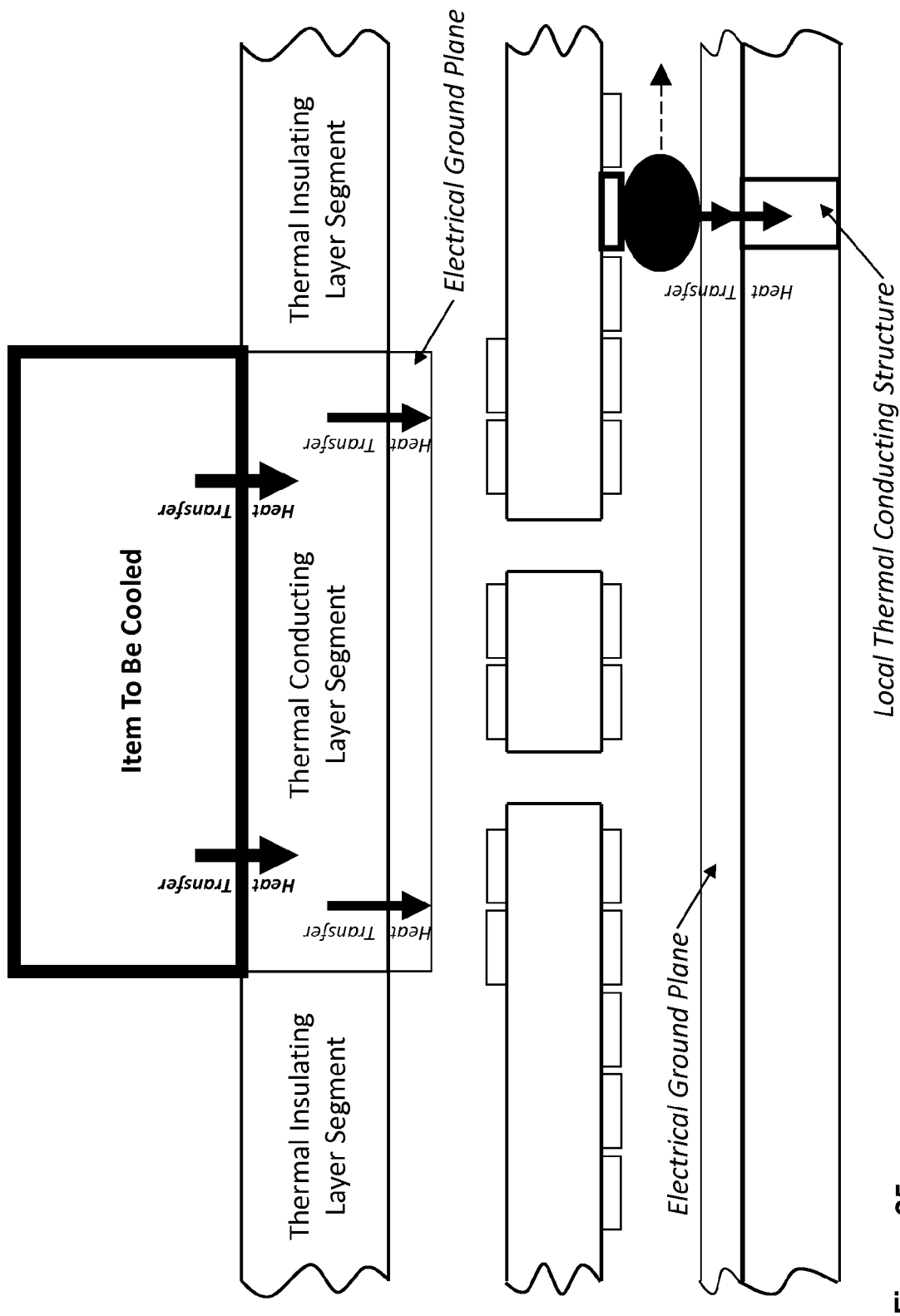
FIG. 35c depicts a representation of heat transfer from the previously heated micro-droplet to the electrical ground plane and further into a local thermal conducting structure joined to the electrical ground plane.

Each of the situations depicted in FIGS. 35a-35c are special cases of the abstract representation depicted in FIG. 33.

Figure 36:
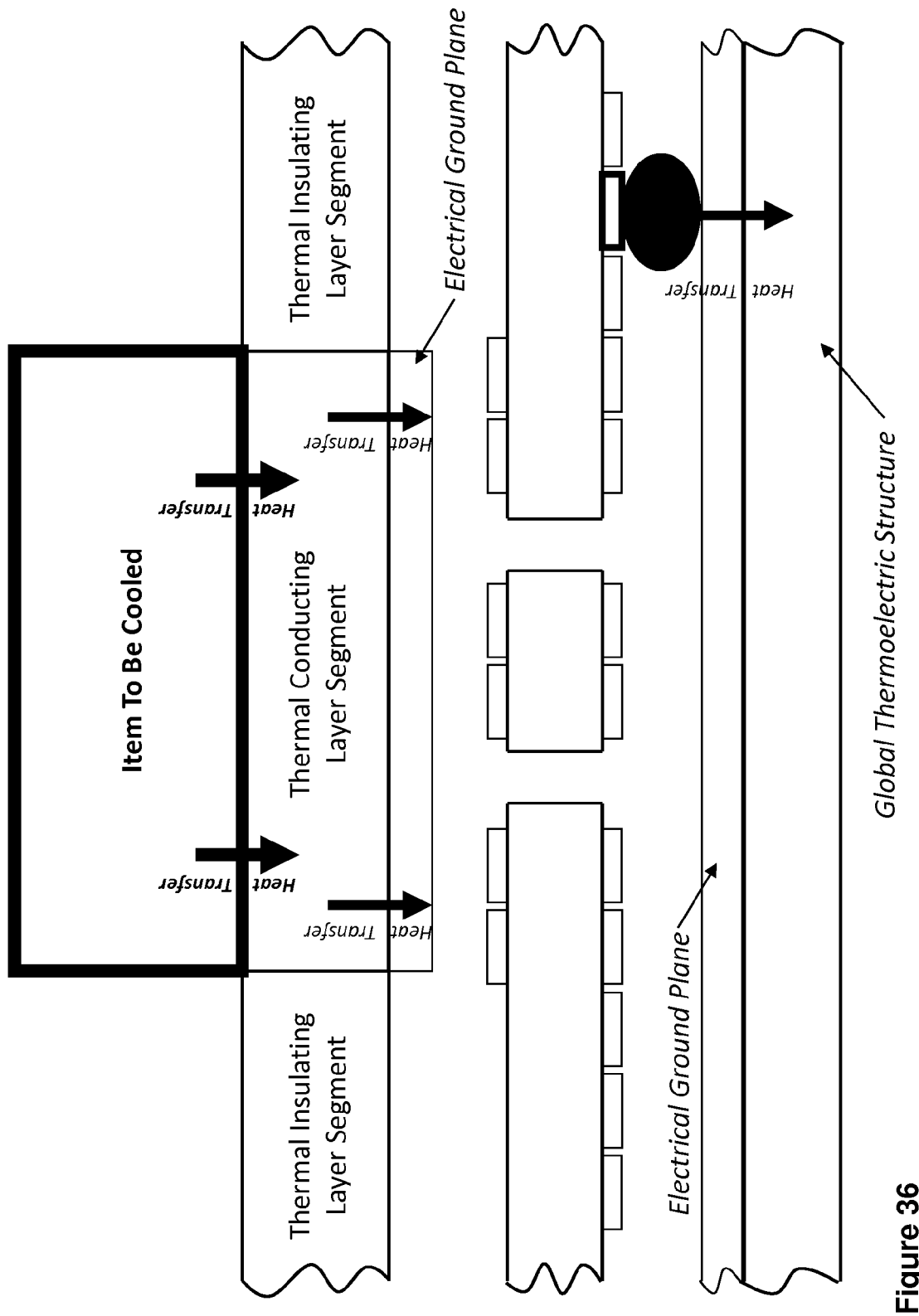

FIG. 36 depicts a variation on the arrangement of FIG. 35b wherein the material joined to the electrical ground plane comprises a "global" (large area) thermoelectric structure.

Figure 37:
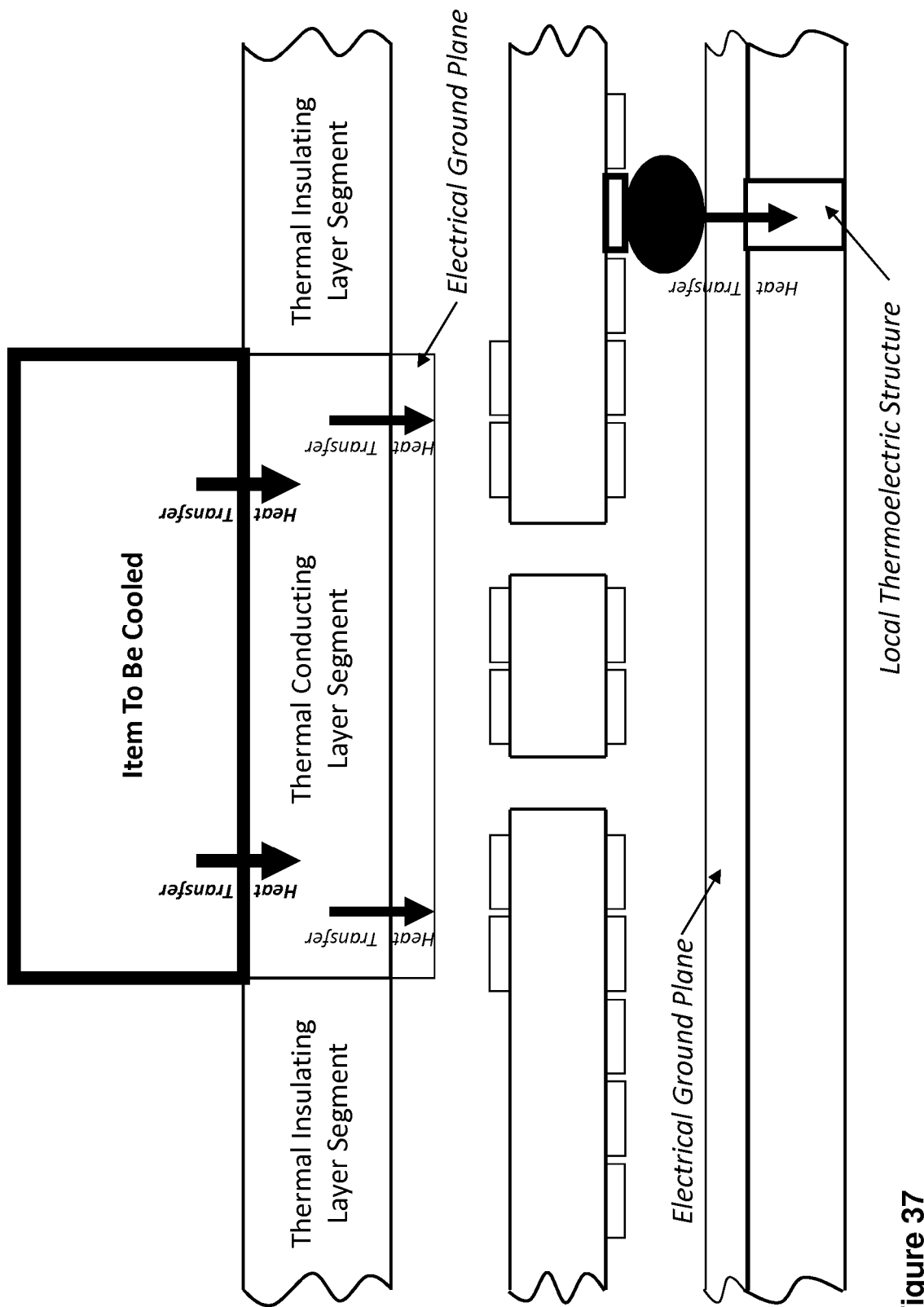

FIG. 37 depicts a variation on the arrangements of FIG. 35c and FIG. 36 combining features from each, wherein heat is transferred from the previously heated micro-droplet to a local (small area) thermoelectric structure.

Figure 38:
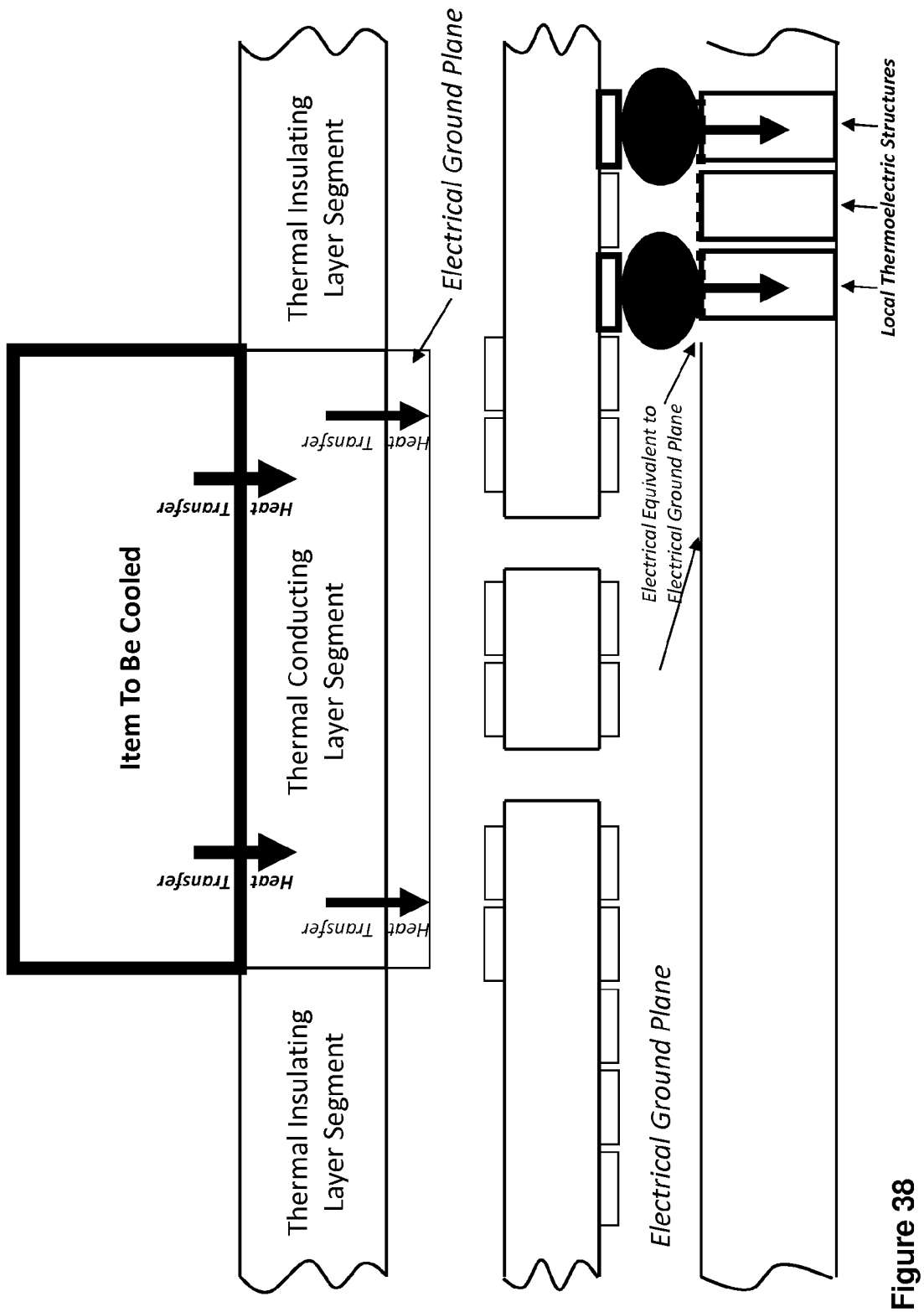

FIG. 38 depicts a variation on the arrangement of FIG. 35b comprising a plurality of local (small area) thermoelectric structures. In an embodiment, each local thermoelectric structure can separately attend to processing heat from properly positioned previously heated micro-droplet.

Figure 39:
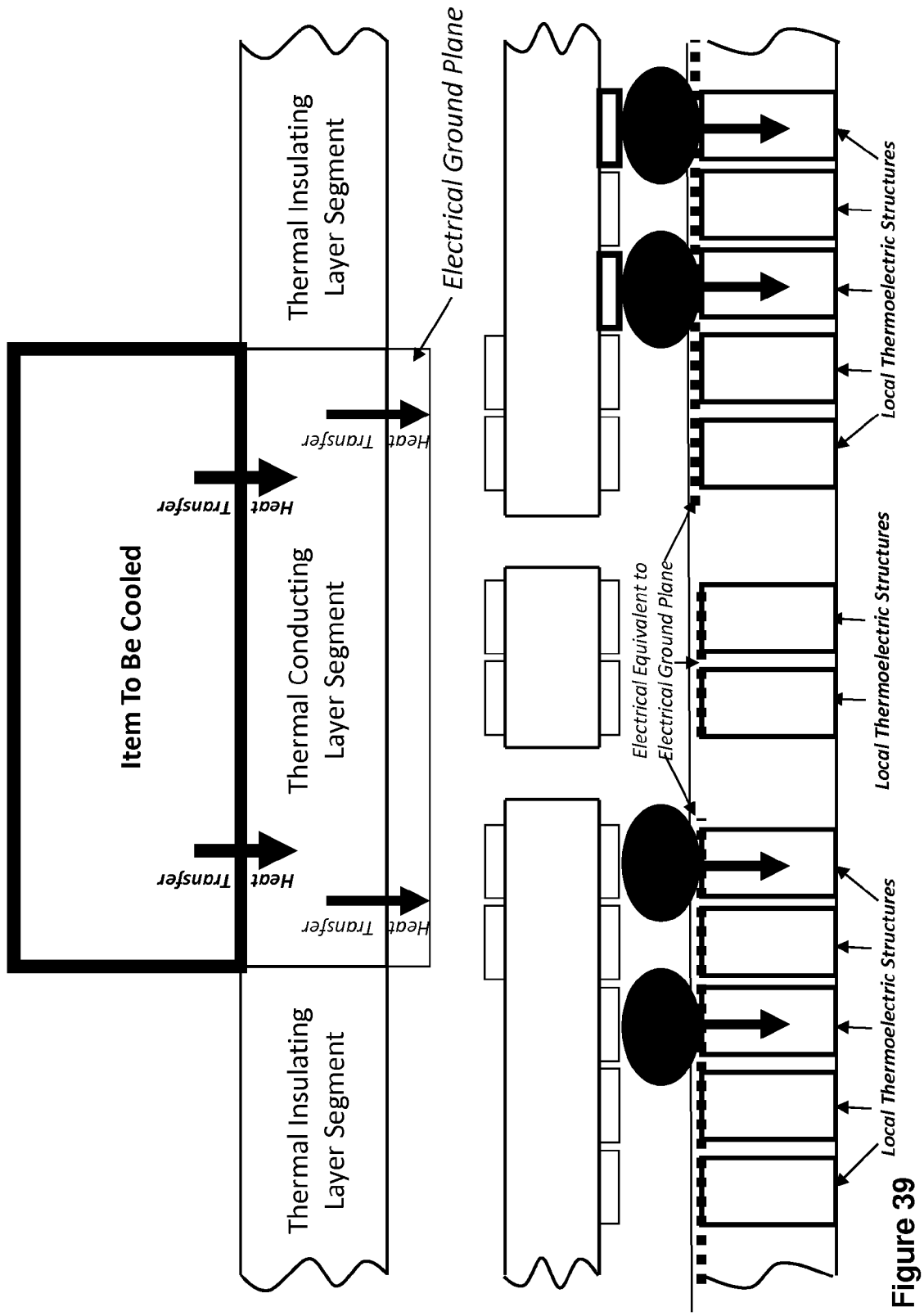

FIG. 39 depicts an expanding variation on the arrangement of FIG. 38 wherein the electrical ground plane depicted throughout earlier figures is replaced by an extended array of local thermoelectric structures.

Figure 40A:
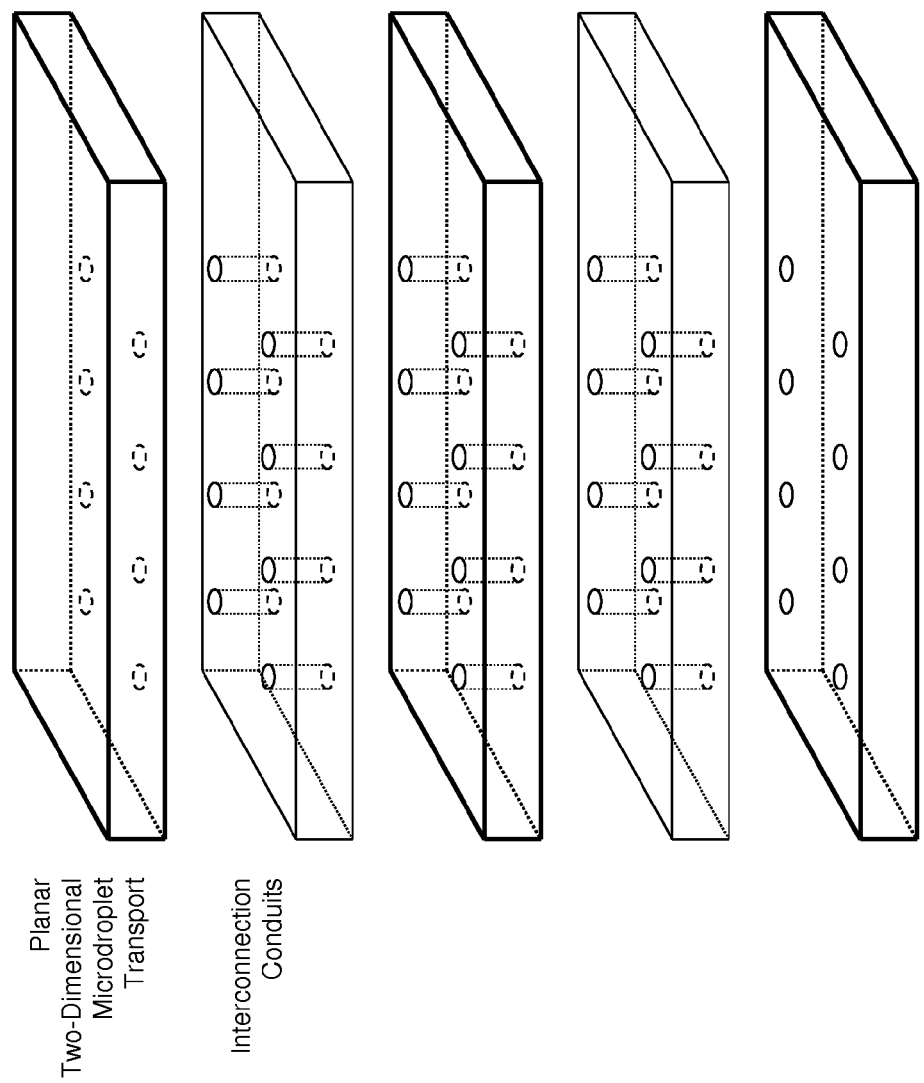

FIG. 40a depicts three planar arrangements for transporting microdroplets of fluidic material in two spatial dimensions (heavier-lined) arranged with openings for interlinking conduits and a connecting section (lighter-lined) providing conduit pathways between these two layers.

Figure 40B:
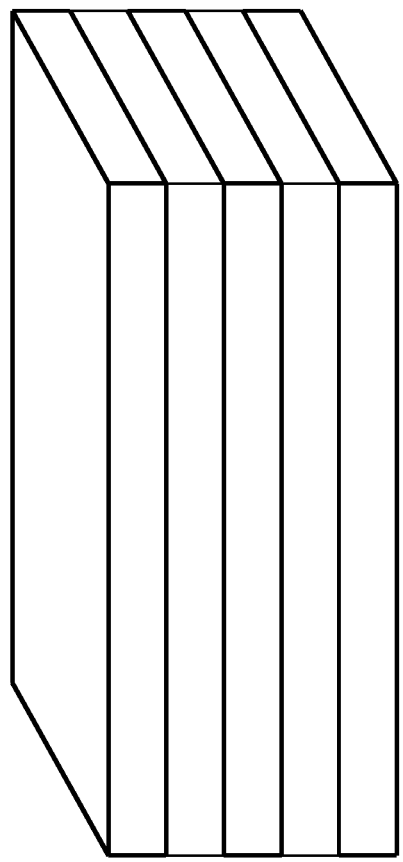

FIG. 40b depicts a final assembly of the three example planar microdroplet transport arrangement layers assembled together interleaved with the two example connecting sections presented in FIG. 40a.

Figure 40C:
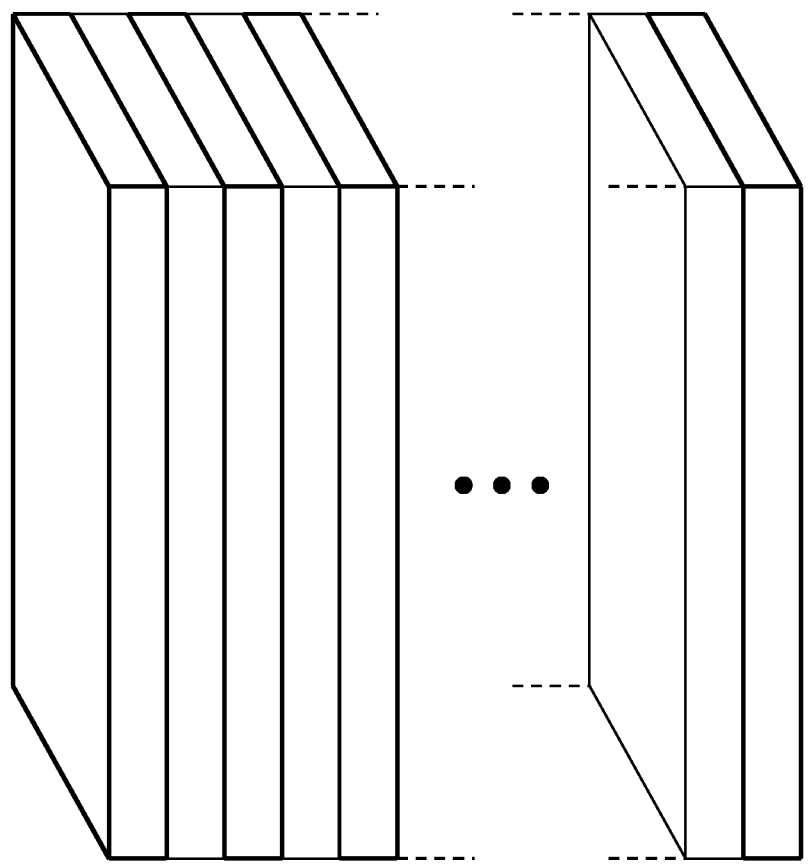

FIG. 40c depicts a representation of an example comprising some number of planar microdroplet transport arrangement layers, said number greater than three.

Figure 41A:
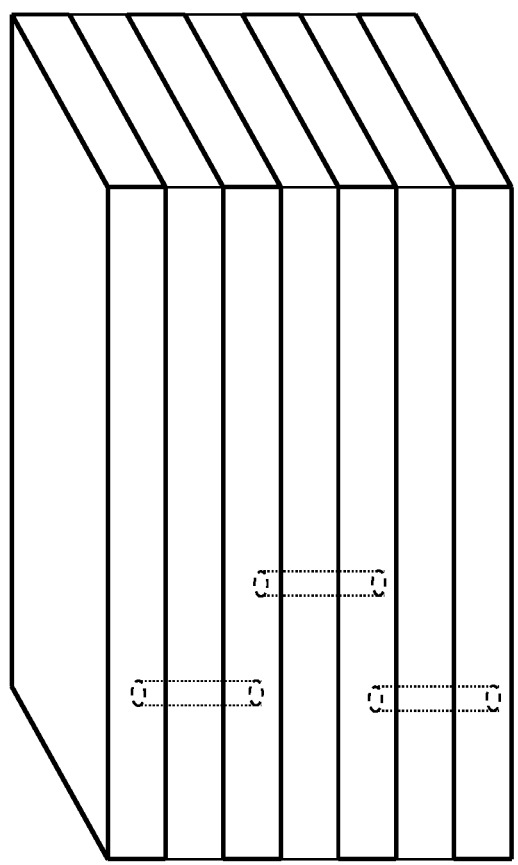

FIG. 41a depicts an example arrangement wherein pairs of planar microdroplet transport arrangement layers are connected strictly pairwise.

Figure 41B:
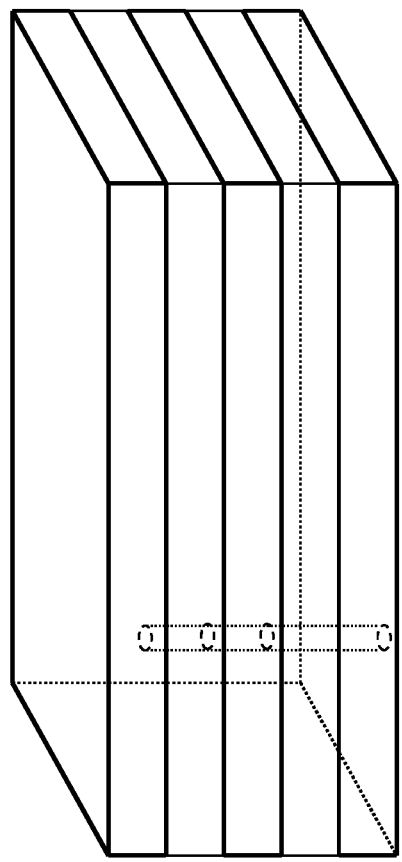

FIG. 41b depicts an example wherein at least one common extended conduit is used to connect three microdroplet transport arrangement layers.

Figure 41C:
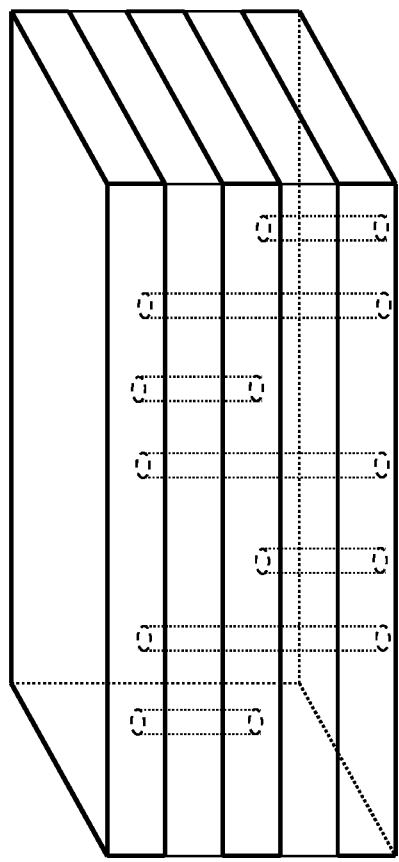

FIG. 41c depicts an example arrangement wherein the arrangements of FIGS. 41a and 41b are combined.

Figure 42A:
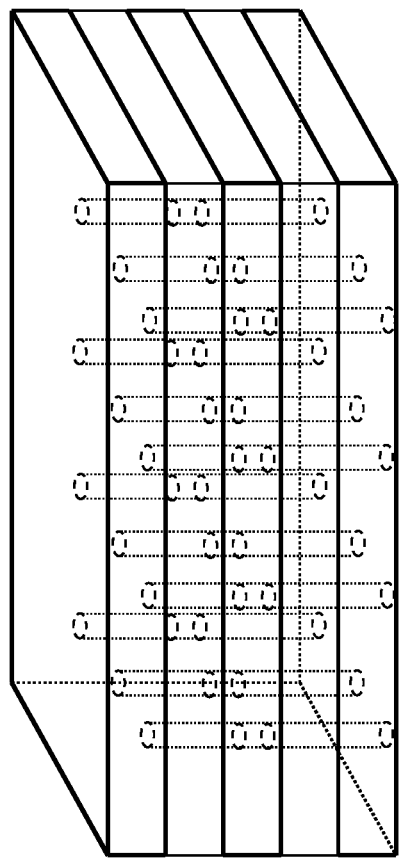

FIG. 42a depicts an arrangement that implements a connective microdroplet transport topology of at least a linear three-dimension ('tube') lattice.

Figure 42B:
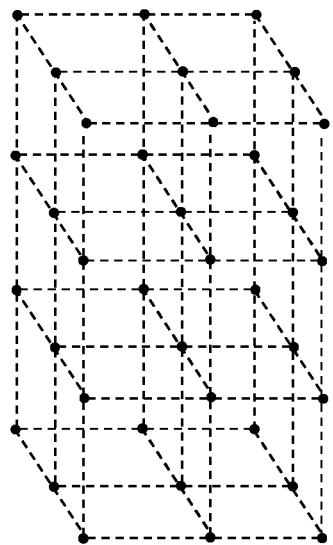

FIG. 42b depicts a linear three-dimension ('tube') microdroplet transport lattice that can be implemented by the arrangement in FIG. 42ab.

Figure 42C:
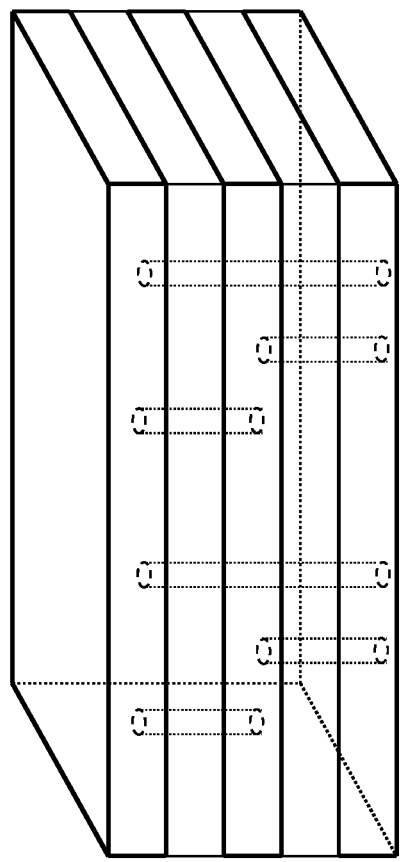

FIG. 42c illustrates a group of pairwise conduits that interconnect the microdroplet transport lattices within the three depicted microdroplet transport arrangement layers in a ring topology.

Figure 43:
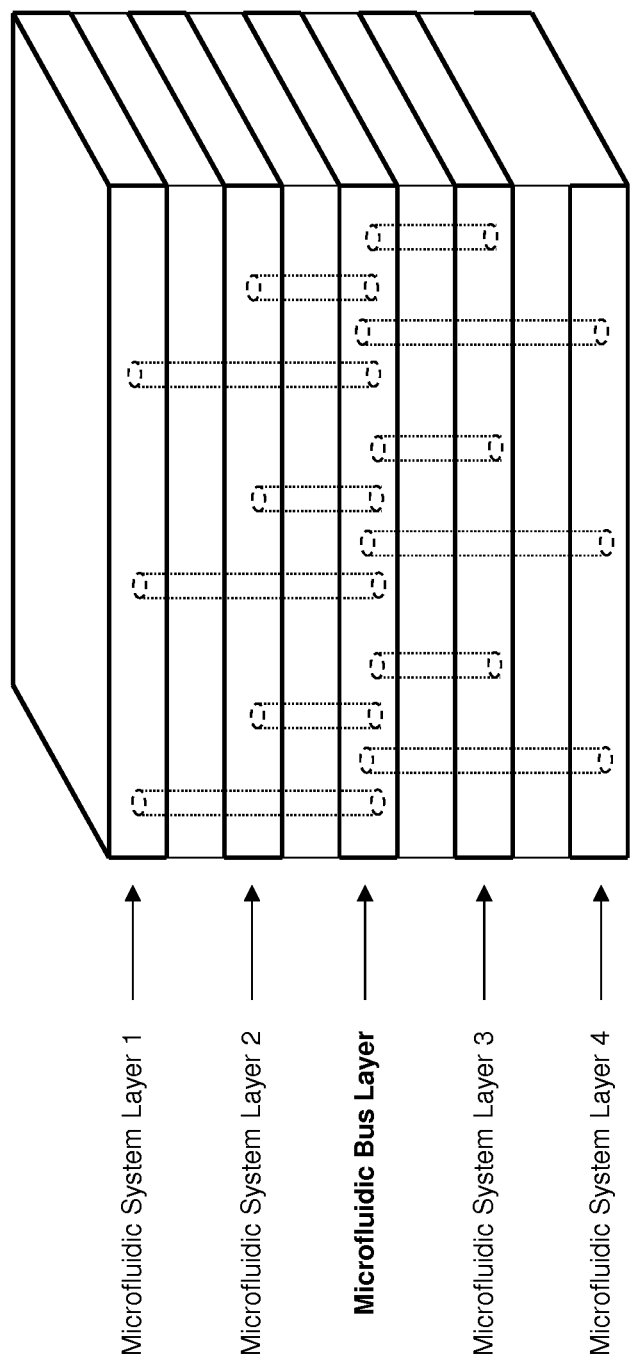

FIG. 43 depicts an example use of a single microdroplet transport arrangement layer configured to serve as a microfluidic bus in service to four other microdroplet transport arrangement layers.

Figure 44A:
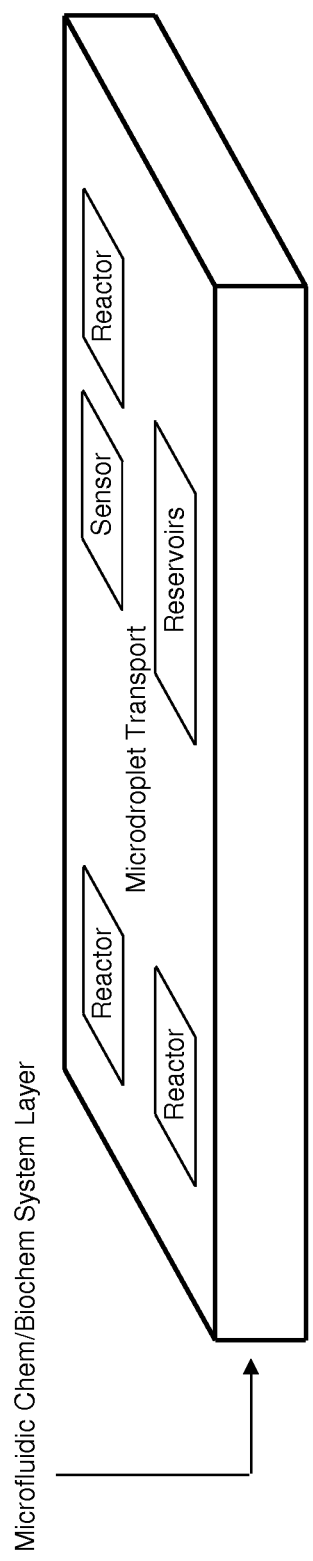
Figure 44B:
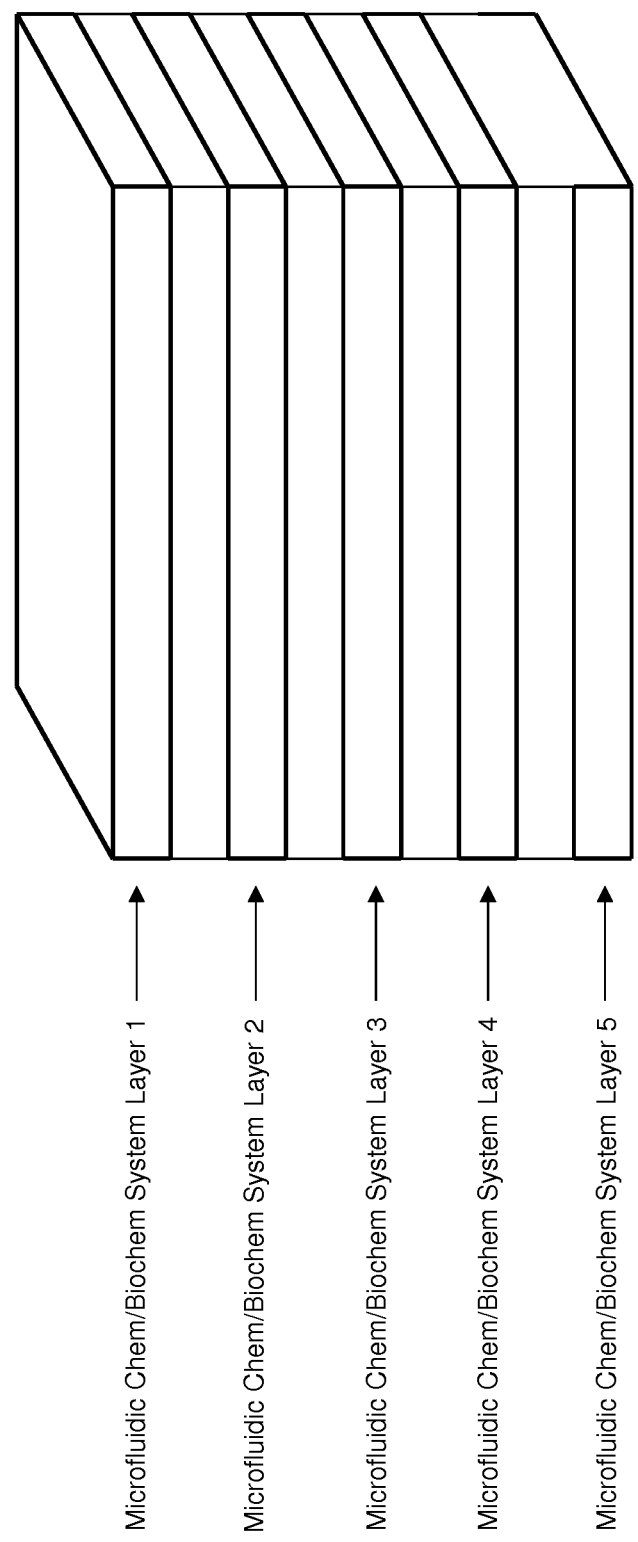

FIG. 44a depicts an example representation wherein a layer in a three-dimensional microdroplet arrangement can internally fluidically interface to one or more chemical and/or biochemical reactor elements, one or more chemical and/or biochemical analysis arrangements, one or more cell culture chambers, one or more chemical and/or biochemical sensors, one or more controlled valves, and/or other apparatus within that layer FIG. 44b depicts a representation of an example comprising at least several such layers.

DETAILED DESCRIPTION

In the following description, reference is made to the accompanying drawing figures which form a part hereof, and which show by way of illustration specific implementations of example embodiments described herein. It is to be understood by those of ordinary skill in this technological field that other embodiments may be utilized, and structural, electrical, as well as procedural changes may be made without departing from the scope of the inventive concept.

In the following description, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

Example Basic Configurations

Various embodiments can be implemented in a number of widely varied ways. This opening section provides a few example basic configurations as an orienting starting point. Many variations on this are provided example basic configuration throughout other sections of the document. None of the example configurations are to be regarded as limiting.

Initial embodiments, example arrangements, and various example implementations are first described in terms of a heat transfer application, providing considerable detail relevant to both that application area as well as several other applications. These teachings are then extended to other applications by provided descriptions of variations, adaptations, and/or substitutions.

Example Basic Configurations Applicable to Heat-Transfer Applications

Figure 1A:
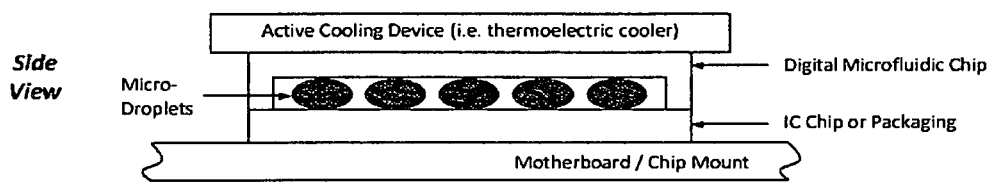
FIG. 1a (adapted from *Adaptive Cooling of Integrated Circuits Using Digital Microfluidics* by P. Paik, K. Chakrabarty, and V. Pamula, Artech House, 2007, ISBN 978-1-59693-138-1) depicts a side view representation of a microfluidic electrowetting micro-droplet transport "chip" implementation fitted over an integrated circuit package and in turn in thermal contact with an active cooling element such as a thermoelectric cooler.
Figure 1B:
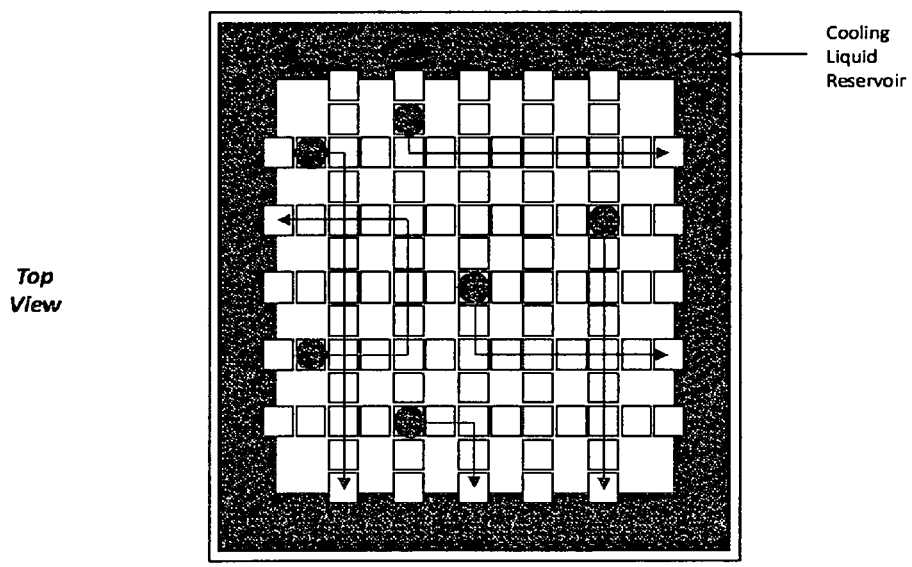
FIG. 1b (adapted from *Adaptive Cooling of Integrated Circuits Using Digital Microfluidics* by P. Paik, K. Chakrabarty, and V. Pamula, Artech House, 2007, ISBN 978-1-59693-138-1) depicts a top view representation of a number of micro-droplets being transported (via electrowetted transport) through various straight and right-angle-turn paths over a planar array of microelectrodes comprised by such a microfluidic electrowetting micro-droplet "chip."
Figure 5:
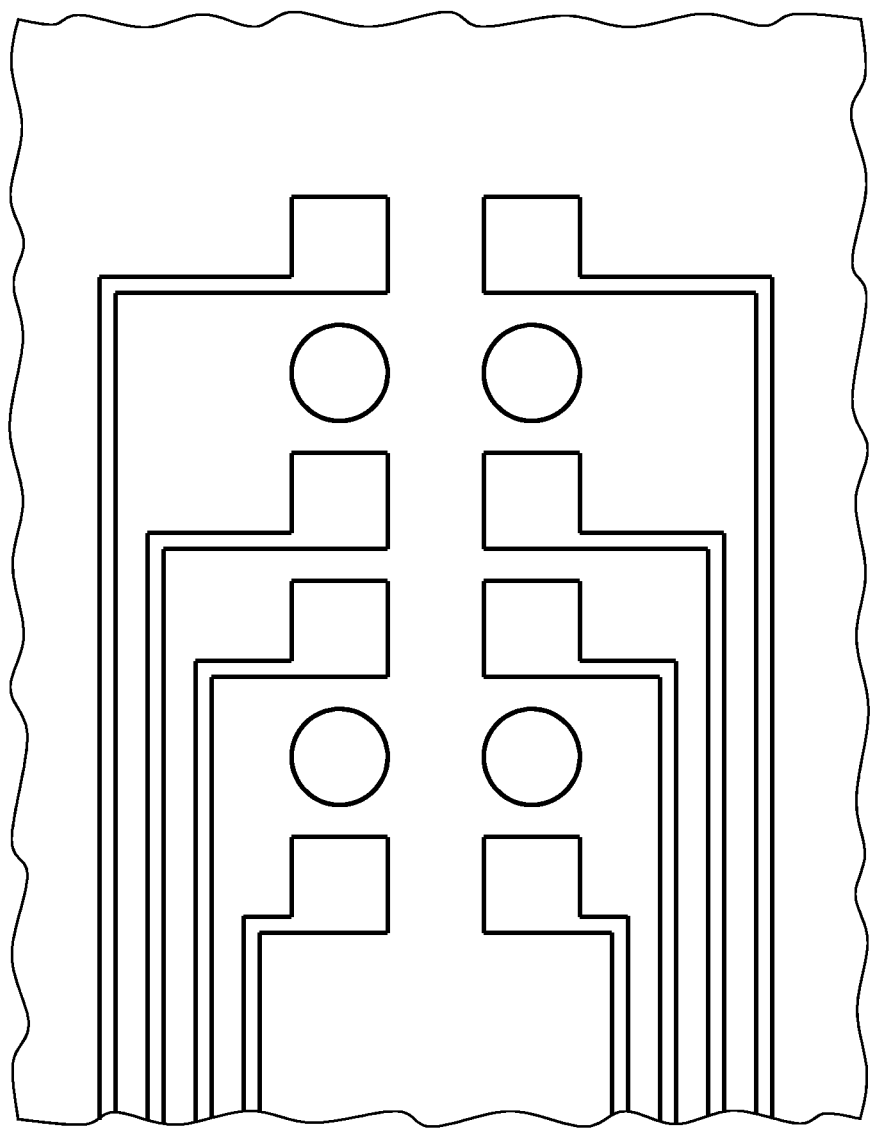

FIG. 5 depicts a representation of the "top" or "bottom" view an example array of microelectrodes, each microelectrode rendered as conductor area on a Printed Circuit Board (PCB) and provided with an associated electrically-conducting "trace" for electrically connecting the microelectrode to voltage potential control circuitry, and interspersed between some pairs of electrodes a physical open hole suitable for a micro-droplet to travel through. (Most of the subsequent remaining Figures show a side-view representation incorporating a side-view of the arrangement in FIG. 5.)

Figure 6:
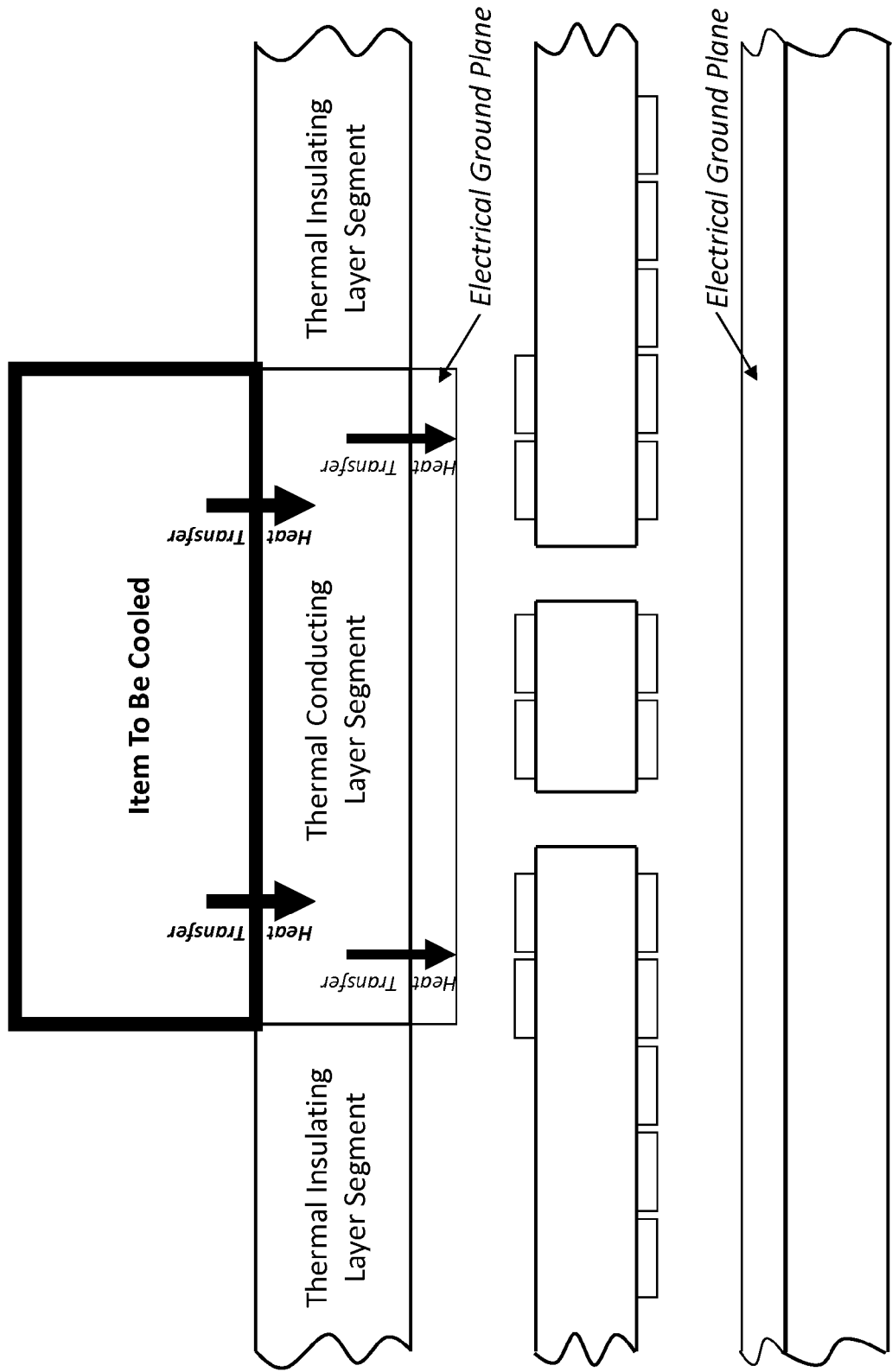
FIG. 6 depicts a side-view representation of an example two-layer micro-droplet transport arrangement with conduits linking the two micro-droplet transport region.

FIG. 6 depicts a side-view representation of an example two-layer micro-droplet transport arrangement with conduits linking the two micro-droplet transport region. This Figure incorporates a side-view of the arrangement like that depicted in FIG. 5. The view shown in FIG. 5 would herein lie in the center facing downwards and comprises additional microelectrodes; two of the physical open holes suitable for a micro-droplet to travel through depicted in FIG. 5 appear (in side-view) in FIG. 6 as the conduits linking the two micro-droplet transport region. In the depiction of FIG. 6, above the upper micro-droplet transport region is a solid layer of PCB material punctuated with thermally-conducting segments that conduct heat from the item to be cooled into the upper micro-droplet transport region. In this example embodiment, the punctuating thermally-conducting segments are also electrical conductors configured to serve as an electrical ground plane that provides both electrical shielding and serves as the ground plane for forming electric fields for micro-droplet transport via electrowetting. Also in the depiction of FIG. 6, below the lower micro-droplet transport region is a solid layer of material (for example, PCB material) whose upper area comprises an electrical conductor layer configured to serve as an electrical ground plane that provides both electrical shielding and serves as the ground plane for forming electric fields for micro-droplet transport via electrowetting.

Example Micro-Droplet Transport Through Non-Heated Transport Region

Figure 7:
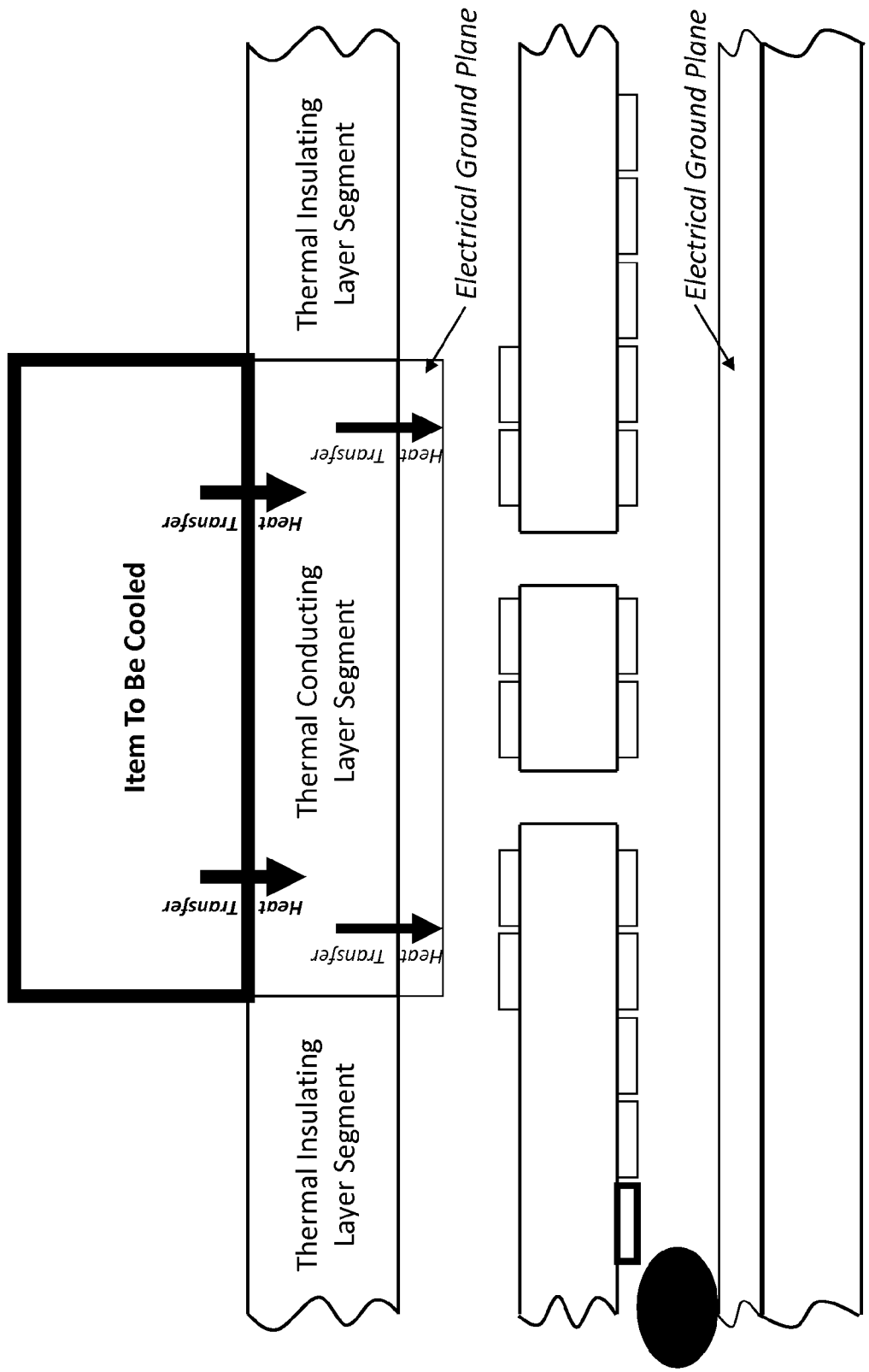
FIG. 7 depicts the example arrangement depicted in FIG. 6 wherein the leftmost microelectrode on the lower micro-droplet transport region is provided with a voltage potential with respect to the lower electric ground plane that physically attracts a micro-droplet (depicted here as a black blob), causing it to move towards said leftmost microelectrode.

FIG. 7 depicts the example arrangement depicted in FIG. 6 wherein the leftmost microelectrode on the lower microdroplet transport region is provided with a voltage potential with respect to the lower electric ground plane that physically attracts a micro-droplet (depicted here as a black blob), causing it to move towards said leftmost microelectrode. The motion of the micro-droplet towards that microelectrode provides the micro-droplet with momentum. In some embodiments the momentum can be utilized in the controlled transport of the micro-droplet towards the next electrode to the right. In other embodiments the momentum can be suppressed by locking the micro-droplet into position under said microelectrode for an interval of time, for example as depicted in FIG. 8.

Figure 8:
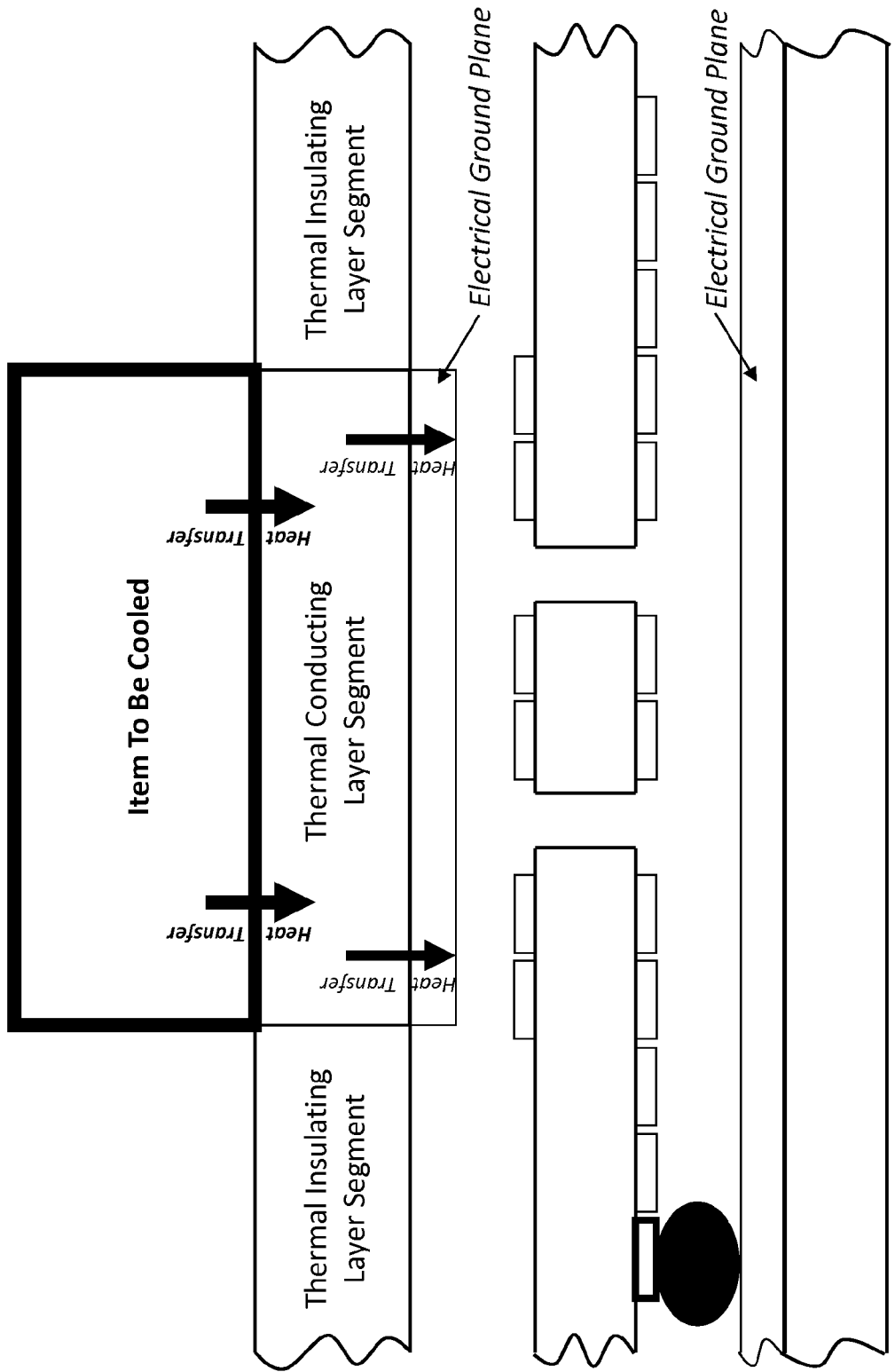
FIG. 8 can depict an arrangement for the suppression of micro-droplet momentum by locking it into position under the leftmost microelectrode for an interval of time.

FIG. 8 can depict an arrangement for the suppression of micro-droplet momentum by locking it into position under the leftmost microelectrode for an interval of time. FIG. 8 can also depict a transient situation of micro-droplet transport wherein the momentum of the micro-droplet is not suppressed (i.e., the micro-droplet is not locked into position under the leftmost microelectrode for an interval of time).

Figure 9:
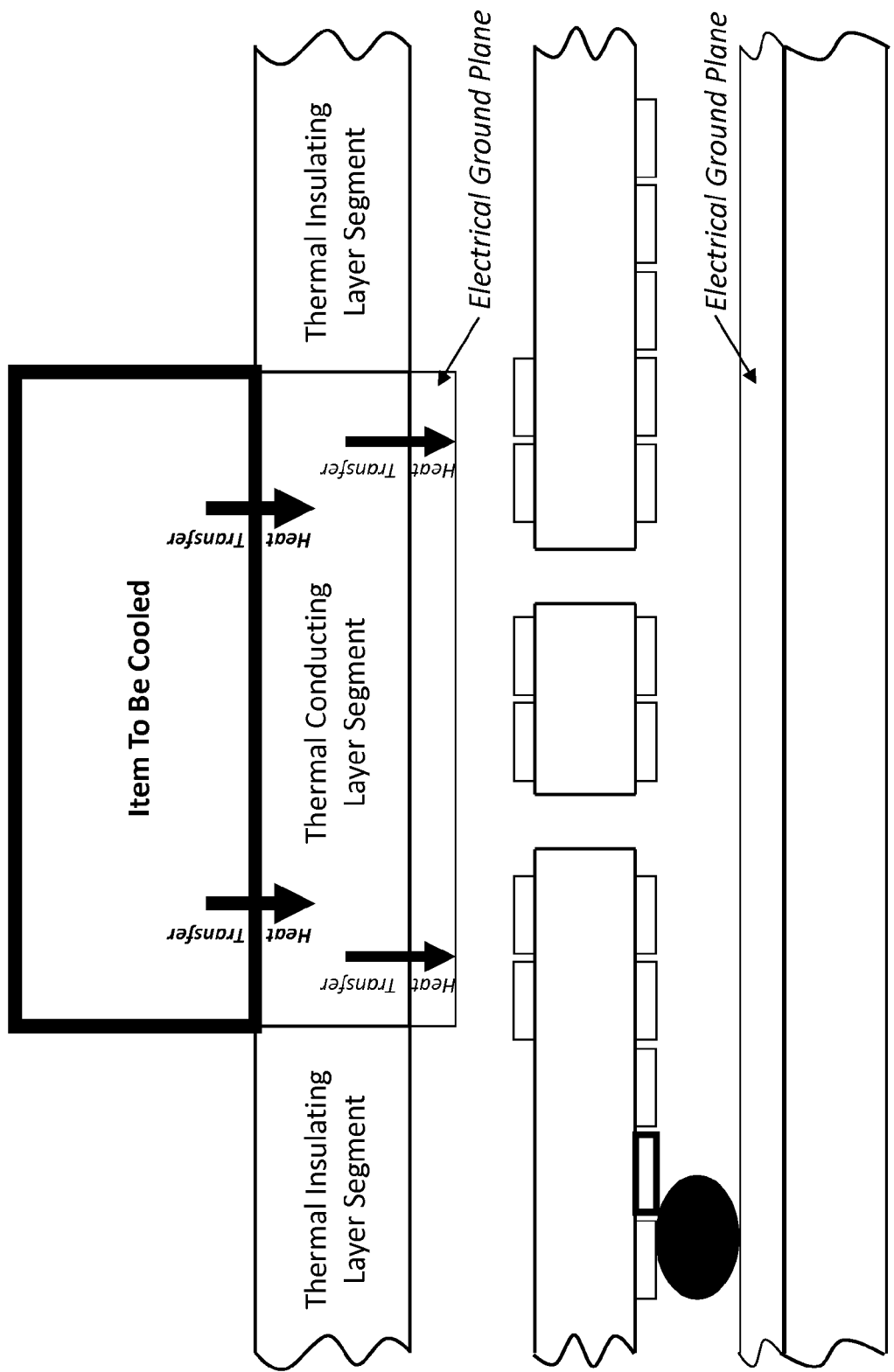
FIG. 9 depicts the deactivation of the previously applied voltage potential to the leftmost microelectrode and the application of the voltage potential to the microelectrode immediately to the right in the depiction, this causing the micro-droplet to be attracted toward the microelectrode immediately to the right and move towards it.

FIG. 9 depicts the deactivation of the previously applied voltage potential to the leftmost microelectrode and the application of the voltage potential to the microelectrode immediately to the right in the depiction, this causing the micro-droplet to be attracted toward the microelectrode immediately to the right and move towards it. In some embodiments, the situation depicted in FIG. 9 occurs immediately after the situation depicted in FIG. 8. In other embodiments, the situation depicted in FIG. 9 occurs immediately after the situation depicted in FIG. 7. Other strategies for sequencing the voltage potentials applied to the microelectrodes involved are also possible and provided for in various implementations.

Figure 10:
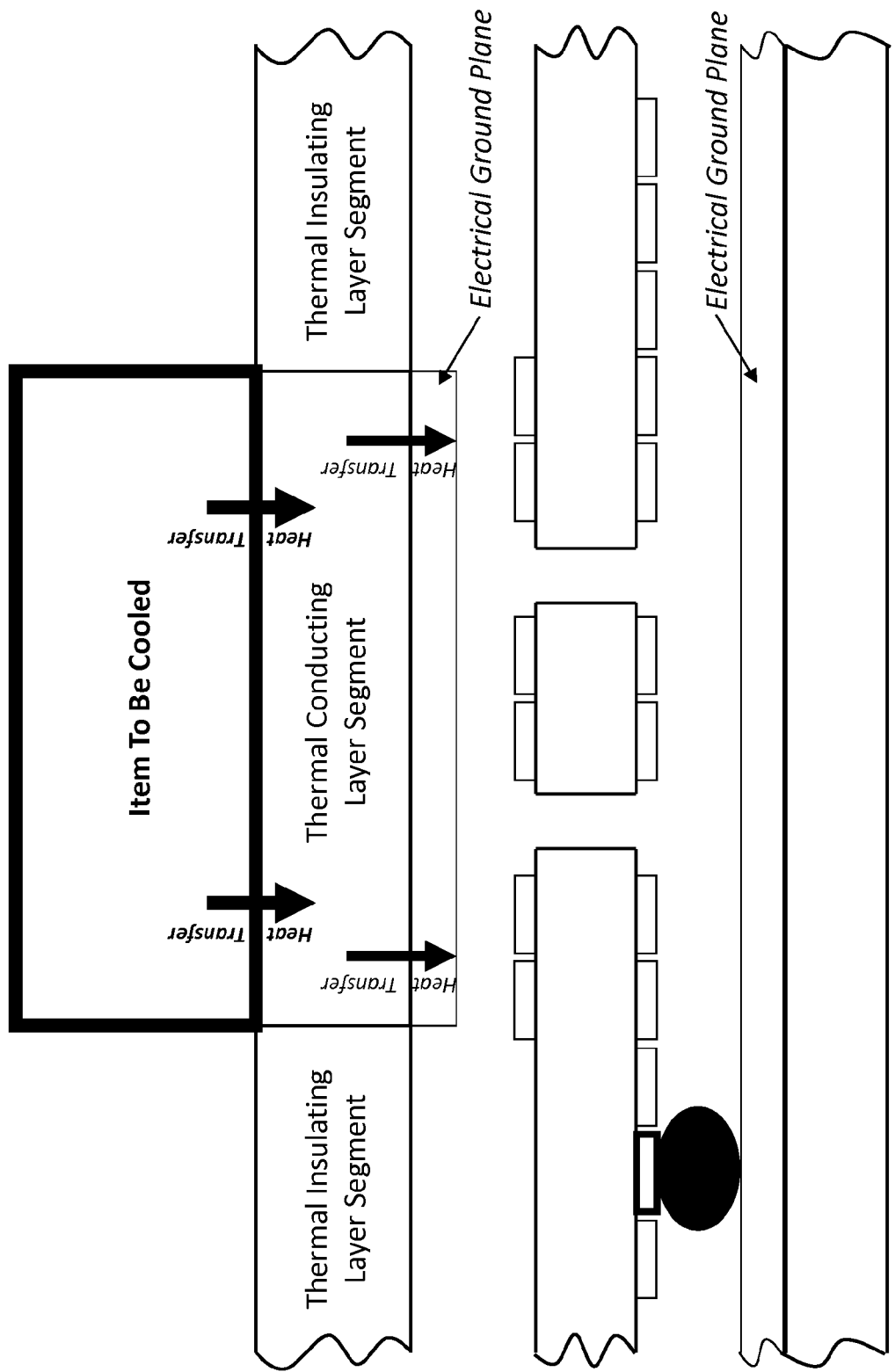
FIG. 10 can depict an arrangement for the suppression of micro-droplet momentum by locking it into position under the activated microelectrode for an interval of time.

FIG. 10 can depict an arrangement for the suppression of micro-droplet momentum by locking it into position under the activated microelectrode for an interval of time. FIG. 10 can also depict a transient situation of micro-droplet transport wherein the momentum of the micro-droplet is not suppressed (i.e., the micro-droplet is not locked into position under the activated microelectrode for an interval of time).

Figure 11:
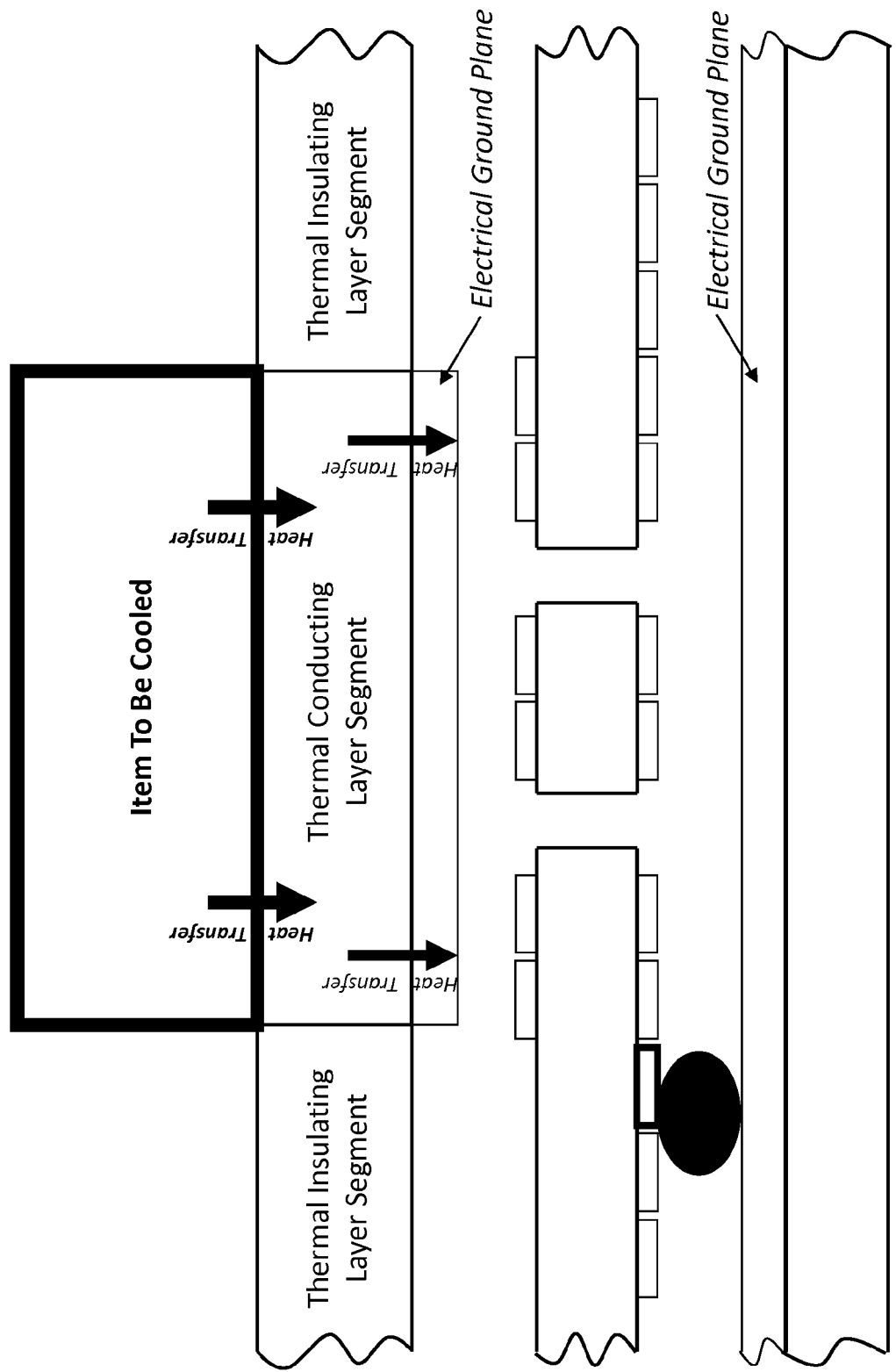
FIG. 11 depicts the deactivation of the previously applied voltage potential to the leftmost microelectrode and the application of the voltage potential to the microelectrode immediately to the right in the depiction, this causing the micro-droplet to be attracted toward the microelectrode immediately to the right and move towards it.

FIG. 11 depicts the deactivation of the previously applied voltage potential to the leftmost microelectrode and the application of the voltage potential to the microelectrode immediately to the right in the depiction, this causing the micro-droplet to be attracted toward the microelectrode immediately to the right and move towards it. In some embodiments, the situation depicted in FIG. 11 occurs immediately after the situation depicted in FIG. 10. In other embodiments, the situation depicted in FIG. 11 occurs immediately after the situation depicted in FIG. 9. Other strategies for sequencing the voltage potentials applied to the microelectrodes involved are also possible and provided for in various implementations.

Figure 12:
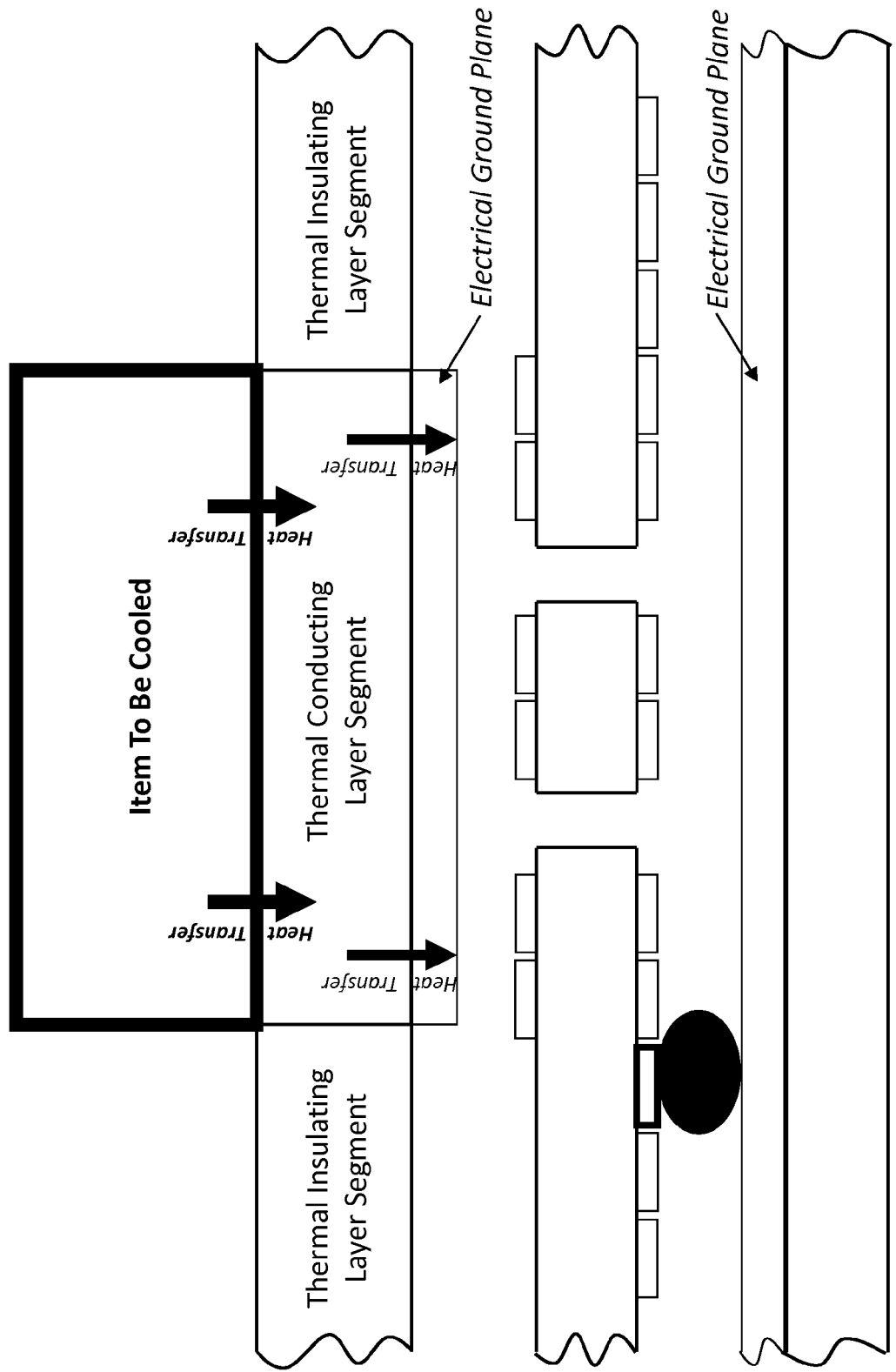
FIG. 12 depicts the situation where wherein the momentum of the micro-droplet is not suppressed (i.e., the micro-droplet is not locked into position under the activated microelectrode for an interval of time) and the micro-droplet continues moving a bit beyond the immediate region crowned by the activated microelectrode.

FIG. 12 depicts the situation where wherein the momentum of the micro-droplet is not suppressed (i.e., the micro-droplet is not locked into position under the activated microelectrode for an interval of time) and the micro-droplet continues moving a bit beyond the immediate region crowned by the activated microelectrode. Alternatively, the micro-droplet can be locked into place by maintaining activation of the activated electrode for an adequate length of time for the micro-droplet to recover from the depicted motion and (via surface tension or other droplet-maintaining processes and forces) settle into a stable position under the depicted activated electrode.

Figure 13:
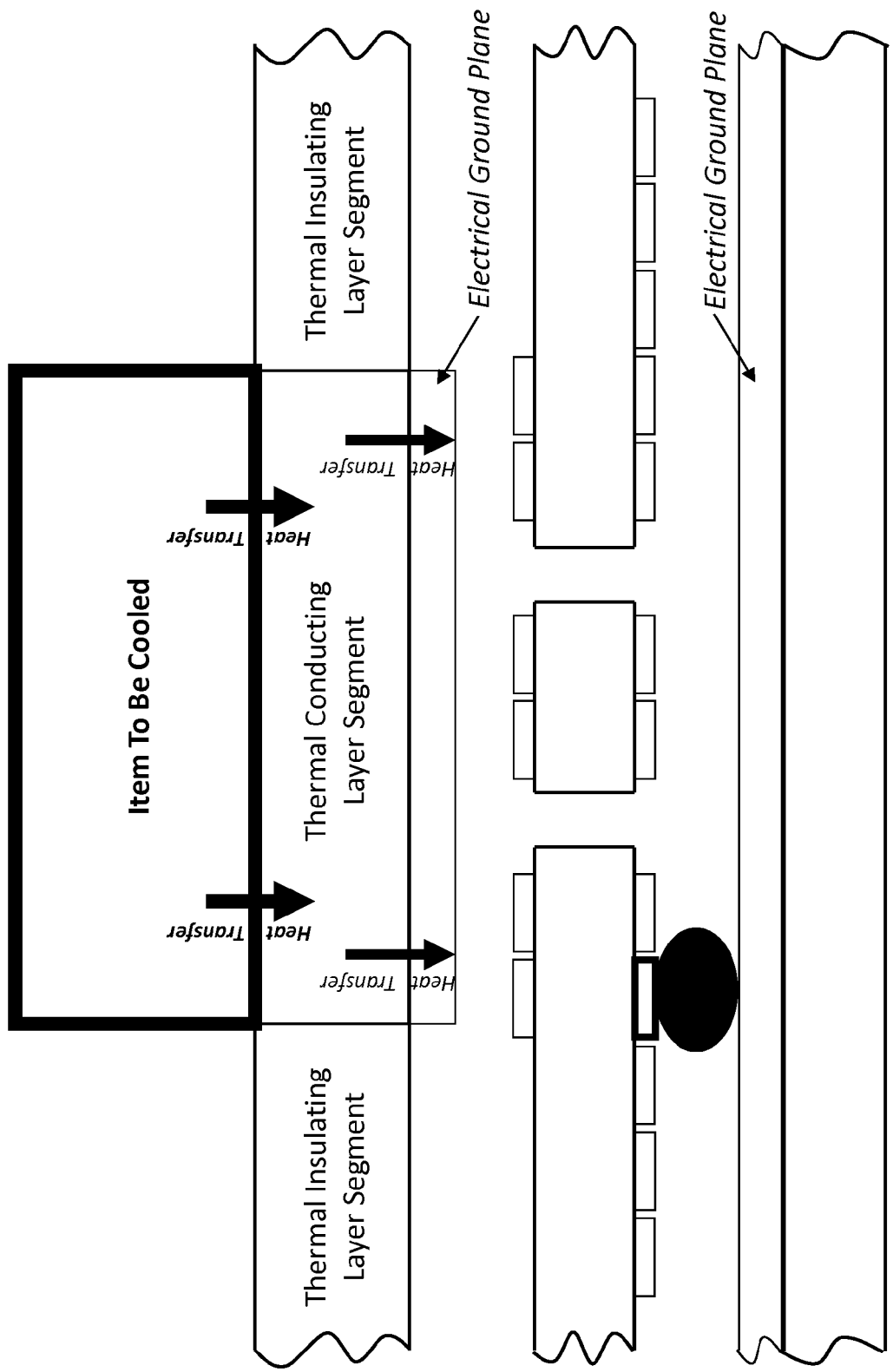
FIG. 13 also depicts a situation where wherein the momentum of the micro-droplet is not suppressed (i.e., the micro-droplet is not locked into position under the activated microelectrode for an interval of time) and the micro-droplet continues moving a bit beyond the immediate region crowned by the activated micro electrode.

FIG. 13 also depicts a situation where wherein the momentum of the micro-droplet is not suppressed (i.e., the micro-droplet is not locked into position under the activated microelectrode for an interval of time) and the micro-droplet continues moving a bit beyond the immediate region crowned by the activated micro electrode. Alternatively, the micro-droplet can be locked into place by maintaining activation of the activated electrode for an adequate length of time for the micro-droplet to recover from the depicted motion and (via surface tension or other droplet-maintaining processes and forces) settle into a stable position under the depicted activated electrode.

Figure 14:
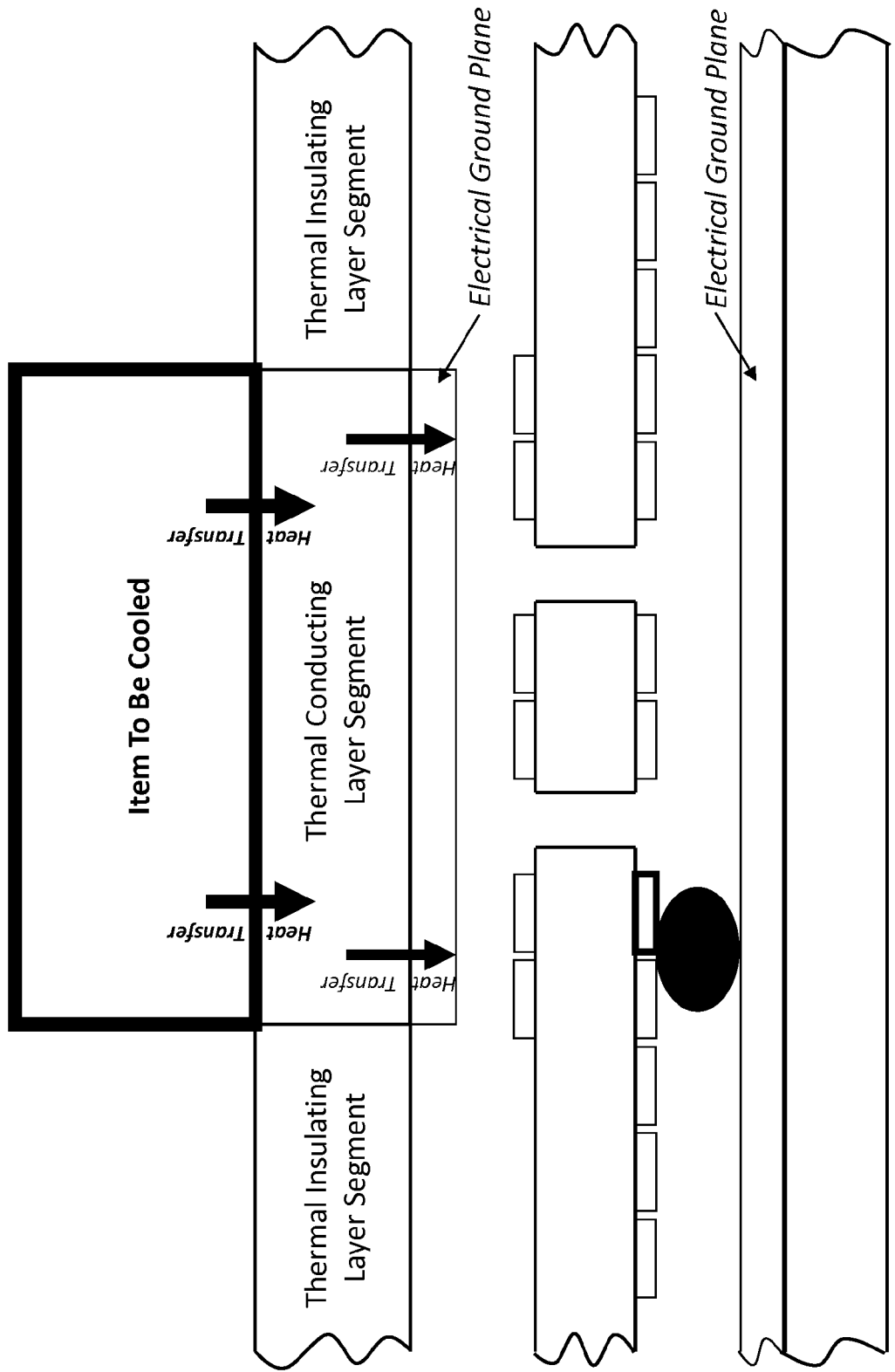
FIG. 14 depicts the deactivation of the previously applied voltage potential to the activated microelectrode of FIG. 13 and the application of the voltage potential to the microelectrode immediately to the right, this causing the microdroplet to be attracted toward the microelectrode immediately to the right and move towards it.

FIG. 14 depicts the deactivation of the previously applied voltage potential to the activated microelectrode of FIG. 13 and the application of the voltage potential to the microelectrode immediately to the right, this causing the micro-droplet to be attracted toward the microelectrode immediately to the right and move towards it.

Figure 15:
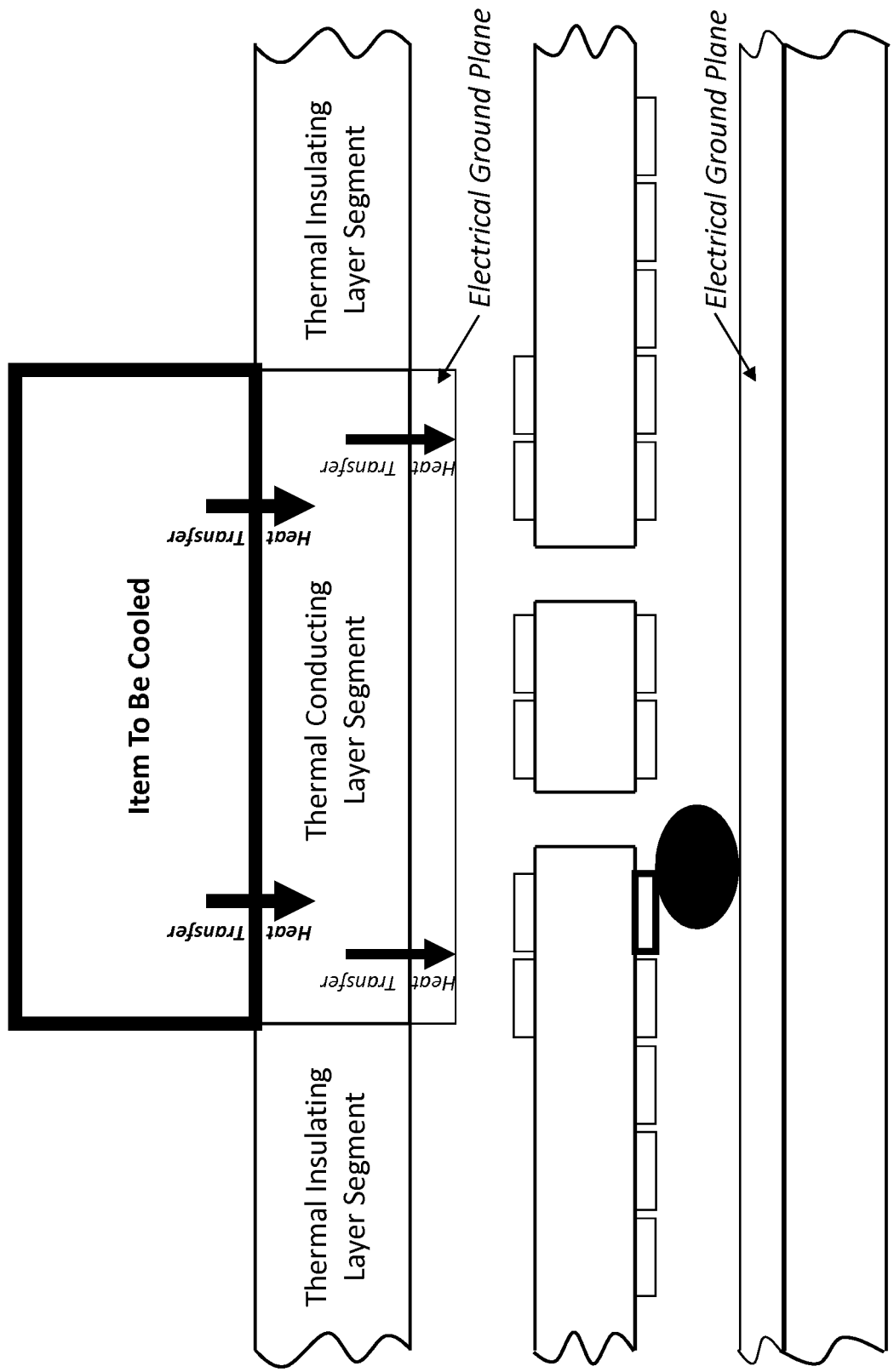
FIG. 15 depicts a situation where wherein the momentum of the micro-droplet is not suppressed (i.e., the microdroplet is not locked into position under the activated microelectrode for an interval of time) and the micro-droplet continues moving a bit beyond the immediate region crowned by the activated microelectrode. Here the microdroplet moves towards the opening of the conduit joining the lower micro-droplet transport region and the upper microdroplet transport region.

FIG. 15 depicts a situation where wherein the momentum of the micro-droplet is not suppressed (i.e., the micro-droplet is not locked into position under the activated microelectrode for an interval of time) and the micro-droplet continues moving a bit beyond the immediate region crowned by the activated microelectrode. Here the micro-droplet moves towards the opening of the conduit joining the lower micro-droplet transport region and the upper micro-droplet transport region.

Figure 16:
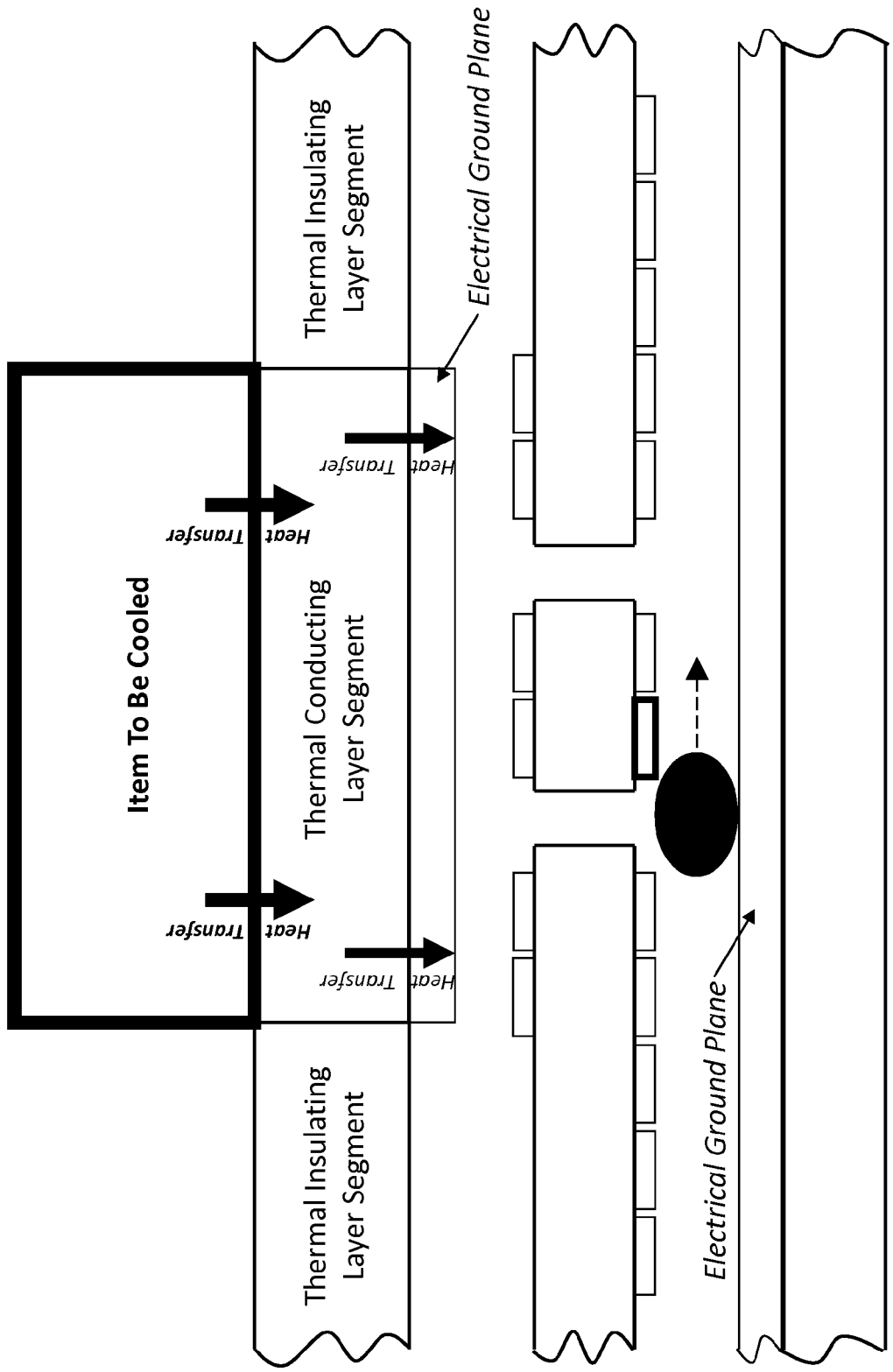
FIG. 16 depicts a situation where the micro-droplet continues its movement to the right within the lower microdroplet transport region, bypassing the chance to travel through the conduit joining the lower micro-droplet transport region and the upper micro-droplet transport region.

FIG. 16 depicts a situation where the micro-droplet continues its movement to the right within the lower micro-droplet transport region, bypassing the chance to travel through the conduit joining the lower micro-droplet transport region and the upper micro-droplet transport region.

Figure 17:
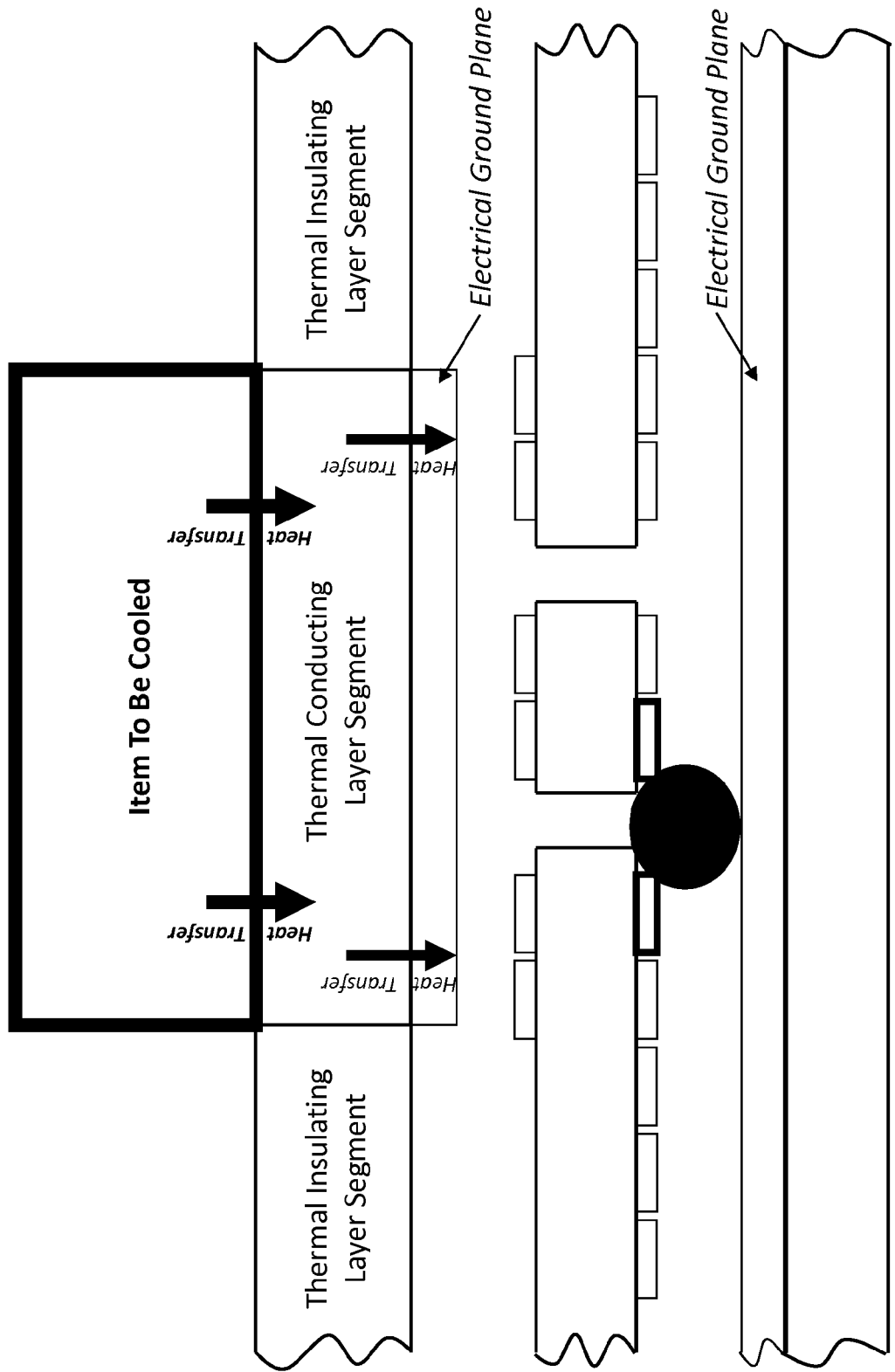
FIG. 17 depicts an example alternative to the course represented by FIG. 16, herein where the momentum of the micro-droplet is suppressed by the simultaneous activation of the microelectrodes on either side of the conduit joining the lower micro-droplet transport region and the upper micro-droplet transport region and maintaining this condition for an adequate length of time for the micro-droplet to recover from the depicted motion and (via surface tension or other droplet-maintaining processes and forces) settle into a stable position under the depicted activated electrode.
Figure 18A:
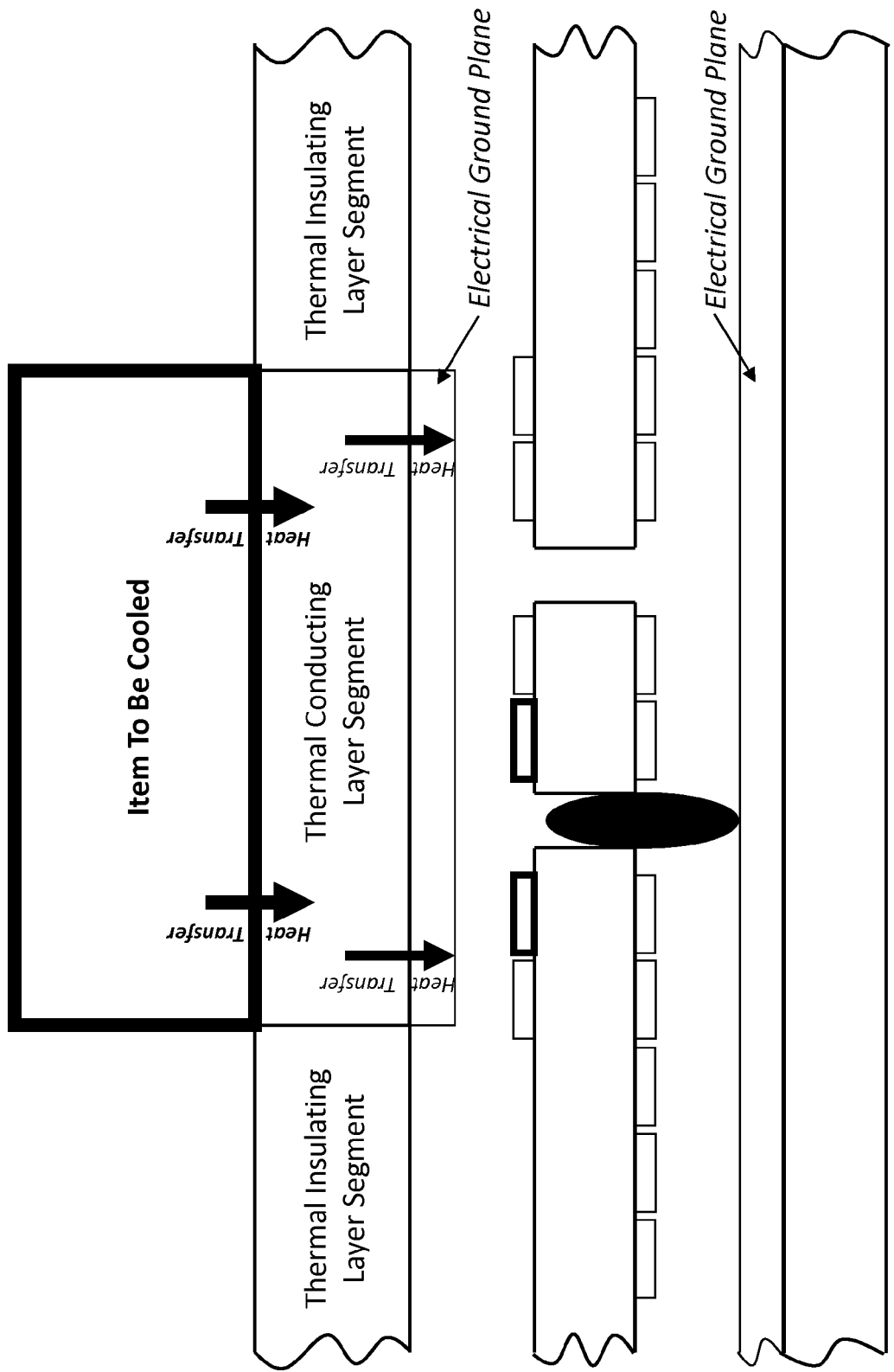
FIGS. 18a-18b, 19a-19b, 20a-20d, 21a-21b, 22a-22b, 23a-23c, 24a-24b, and 25a-25c depict two alternative arrangements for transmission through a first conduit joining two droplet-transport layers from a non-heat-gathering-layer to a heat-gathering-layer and transmission through a second conduit joining the two droplet-transport regions so as to return to a non-heat-gathering-layer. Specifically, the sequence depicted in the series of FIGS. 18a, 19a, 20a, 21a, 22a, 23a, 24a, and 25a depict transmission employing capillary forces and electric fields from distant microelectrodes, while comparatively the sequence depicted in the series of FIGS. 18b, 19b, 20b, 20c, 20d, 21b, 22b, 23b, 23c, 24b, 25b, and 25c depict controlled transmission employing proximate microelectrodes.
Figure 18B:
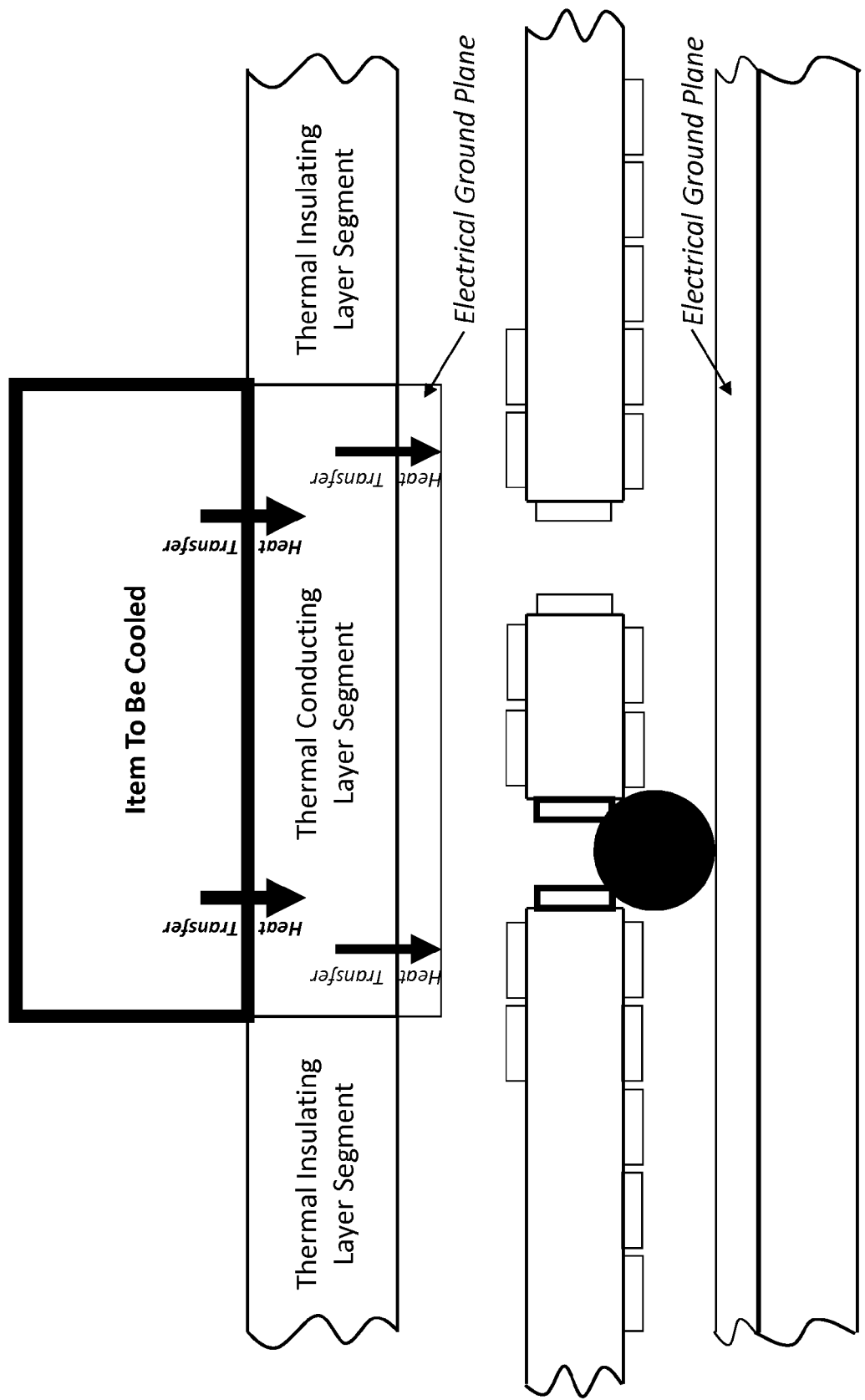
Figure 19A:
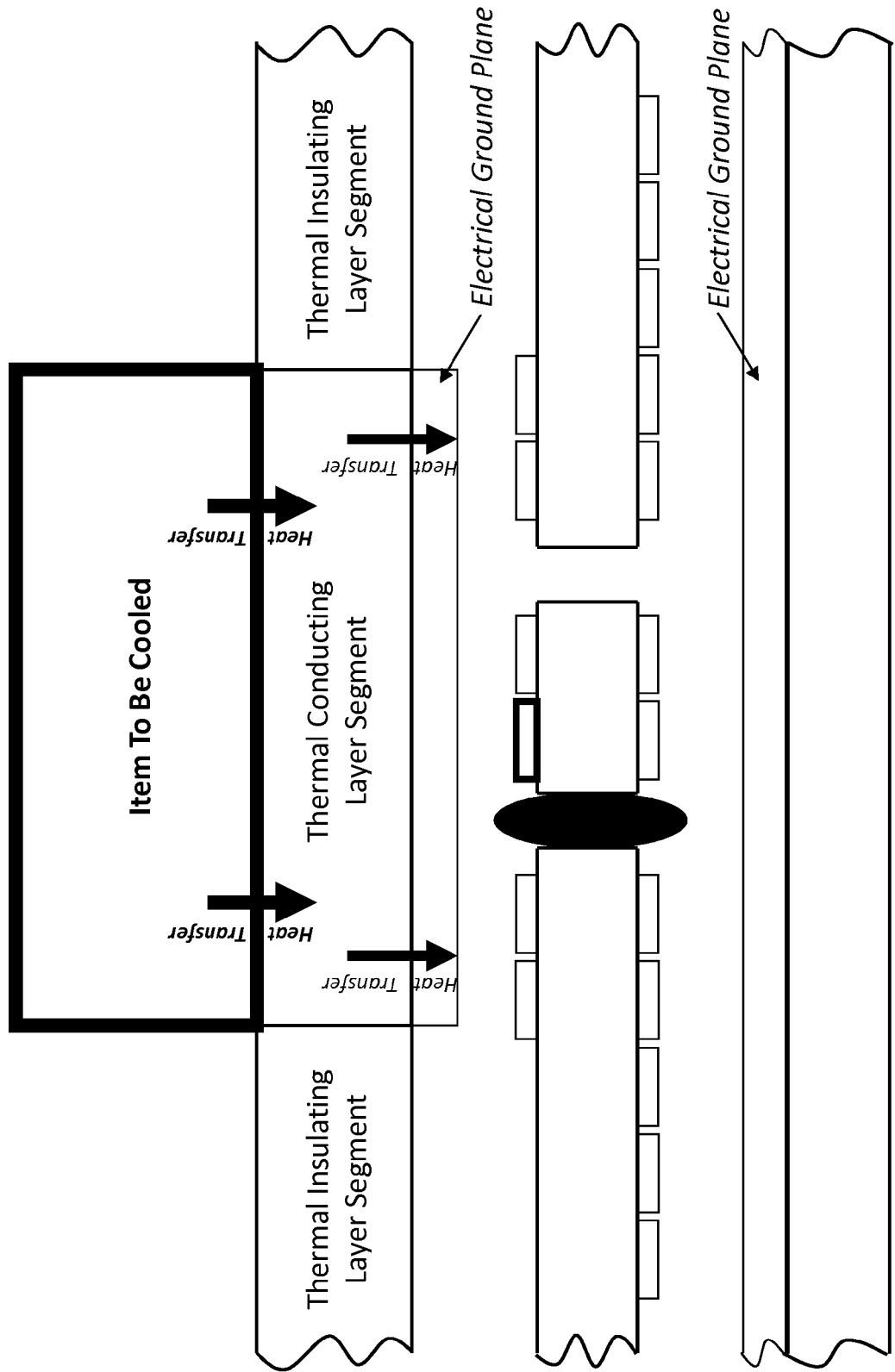
Figure 19B:
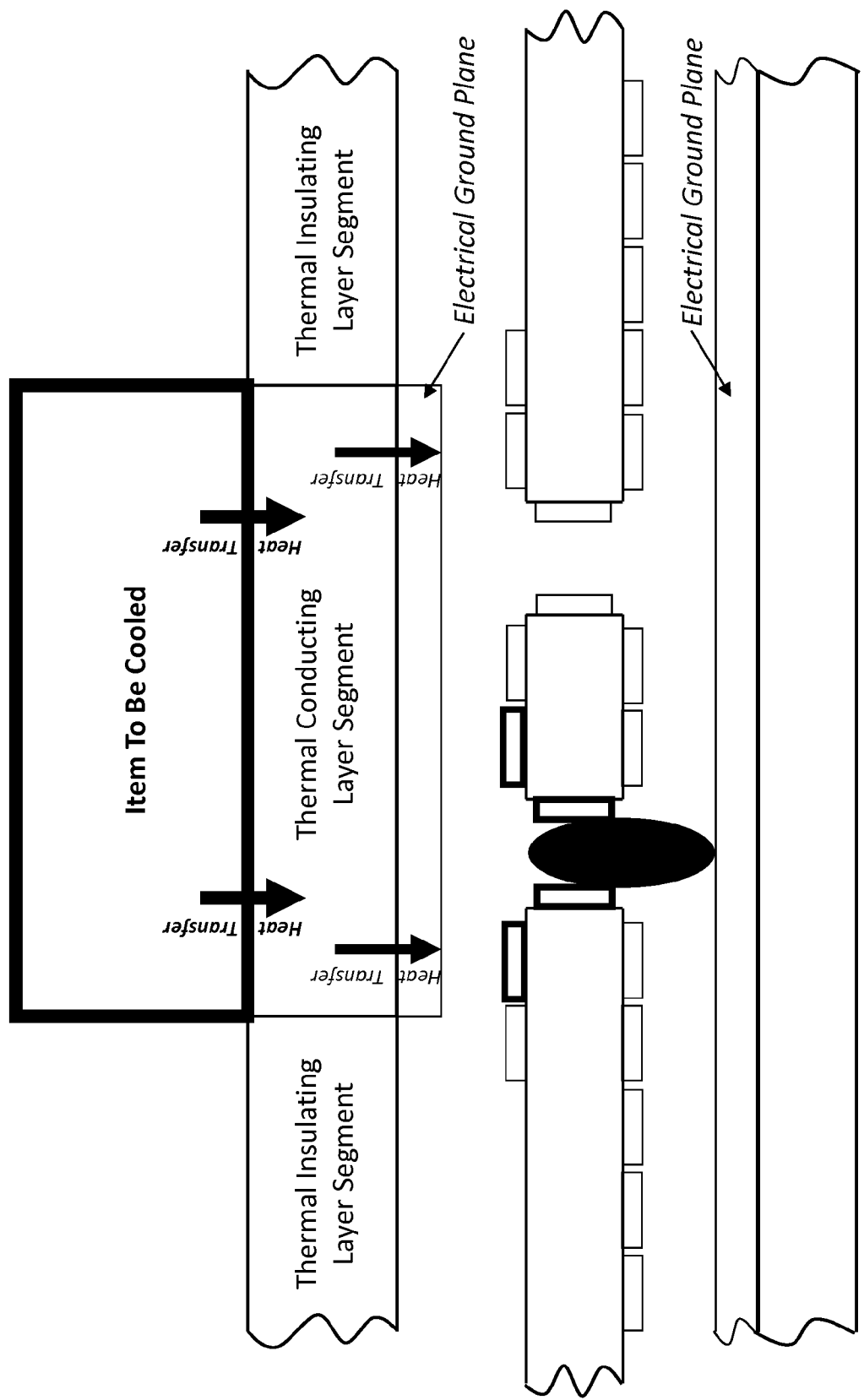
Figure 20A:
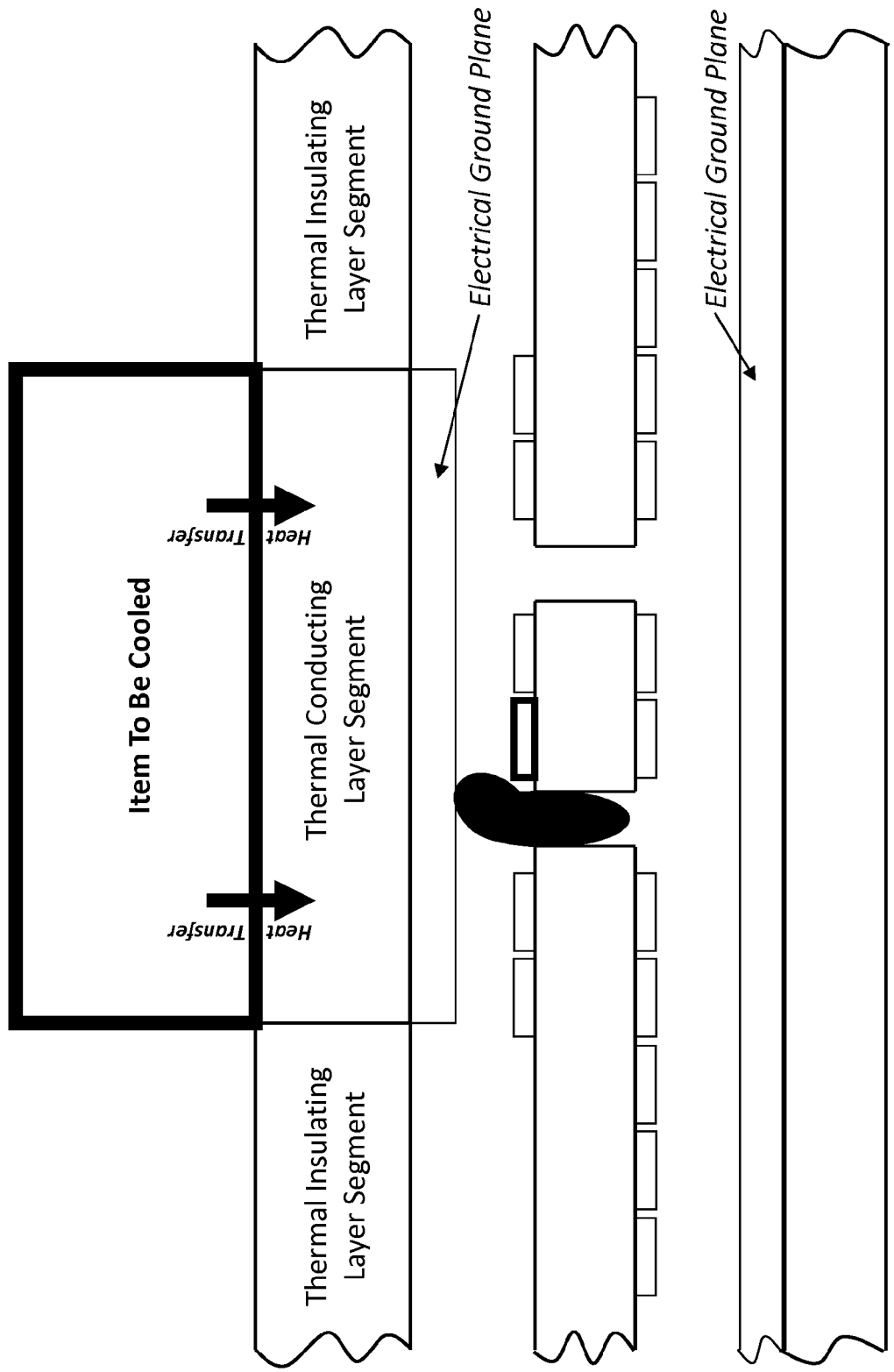
Figure 20B:
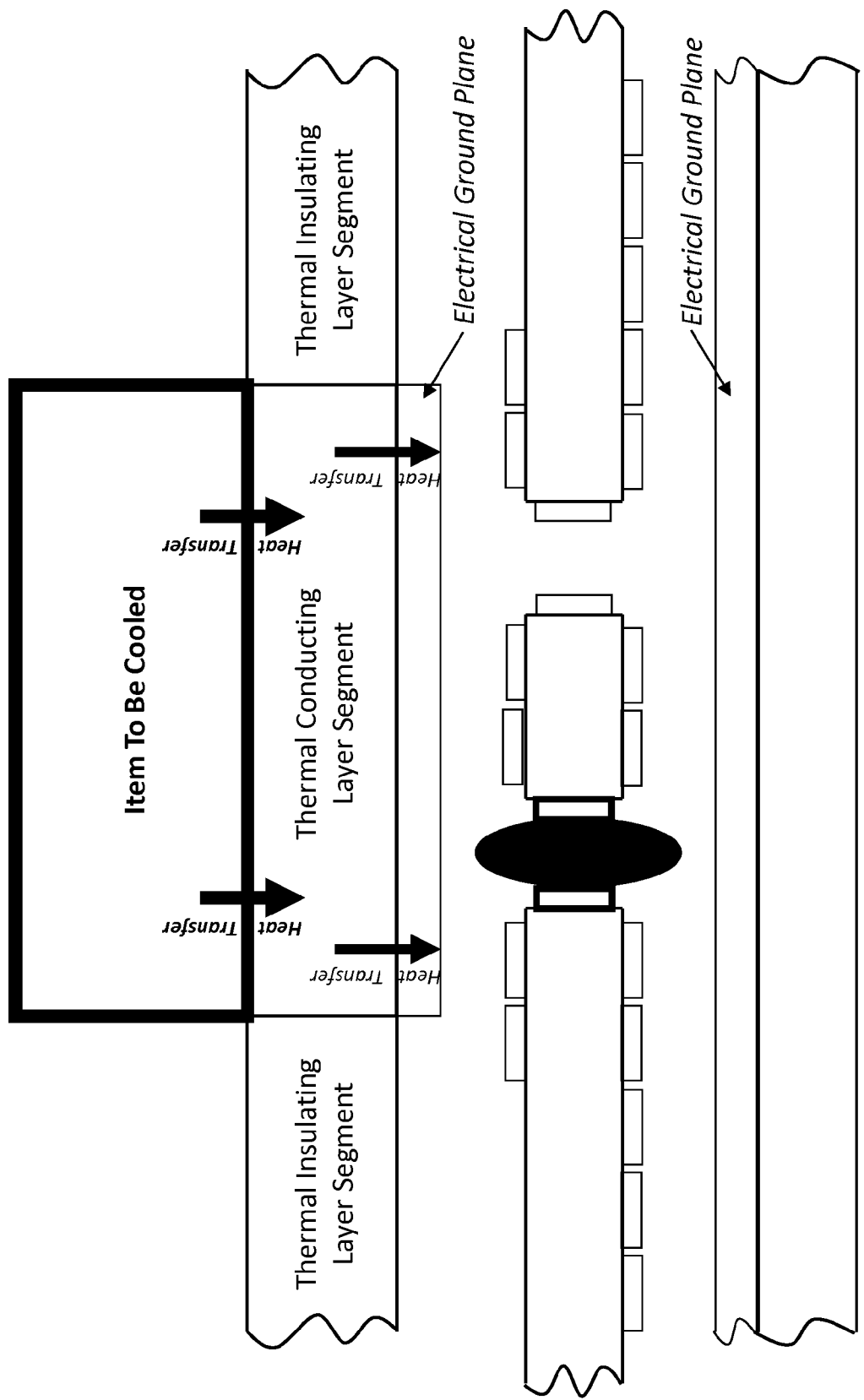
Figure 20C:
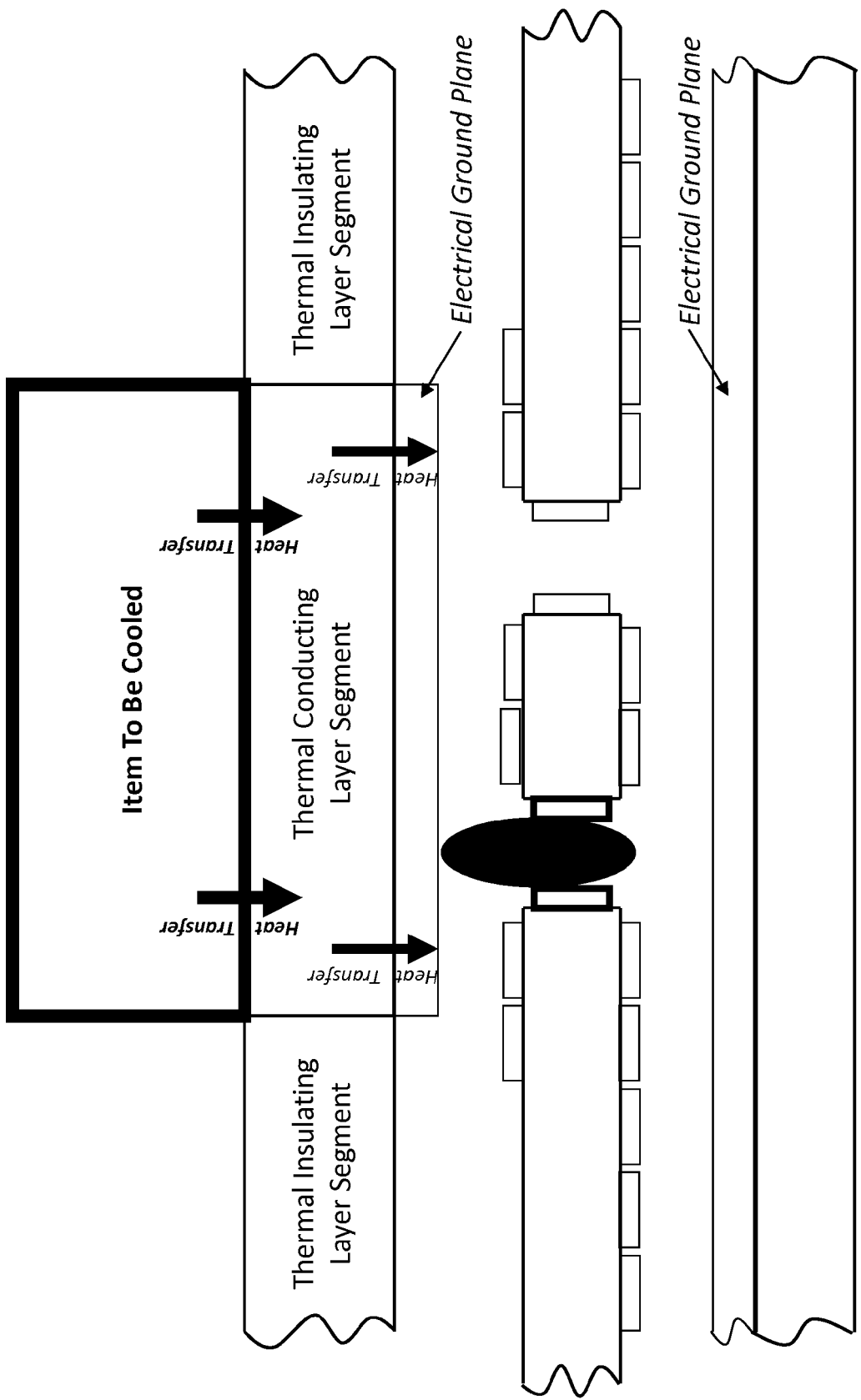
Figure 20D:
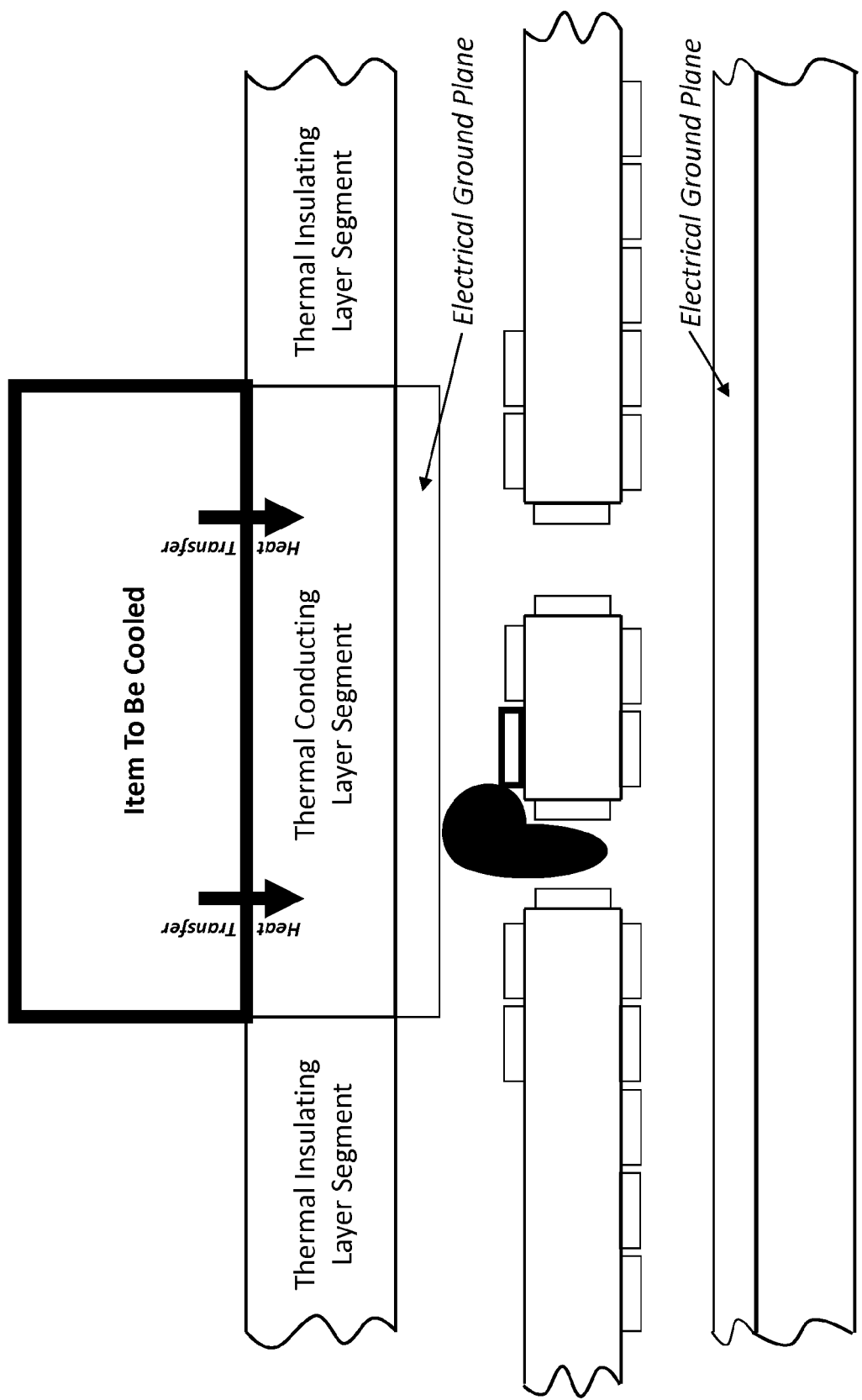
Figure 21A:
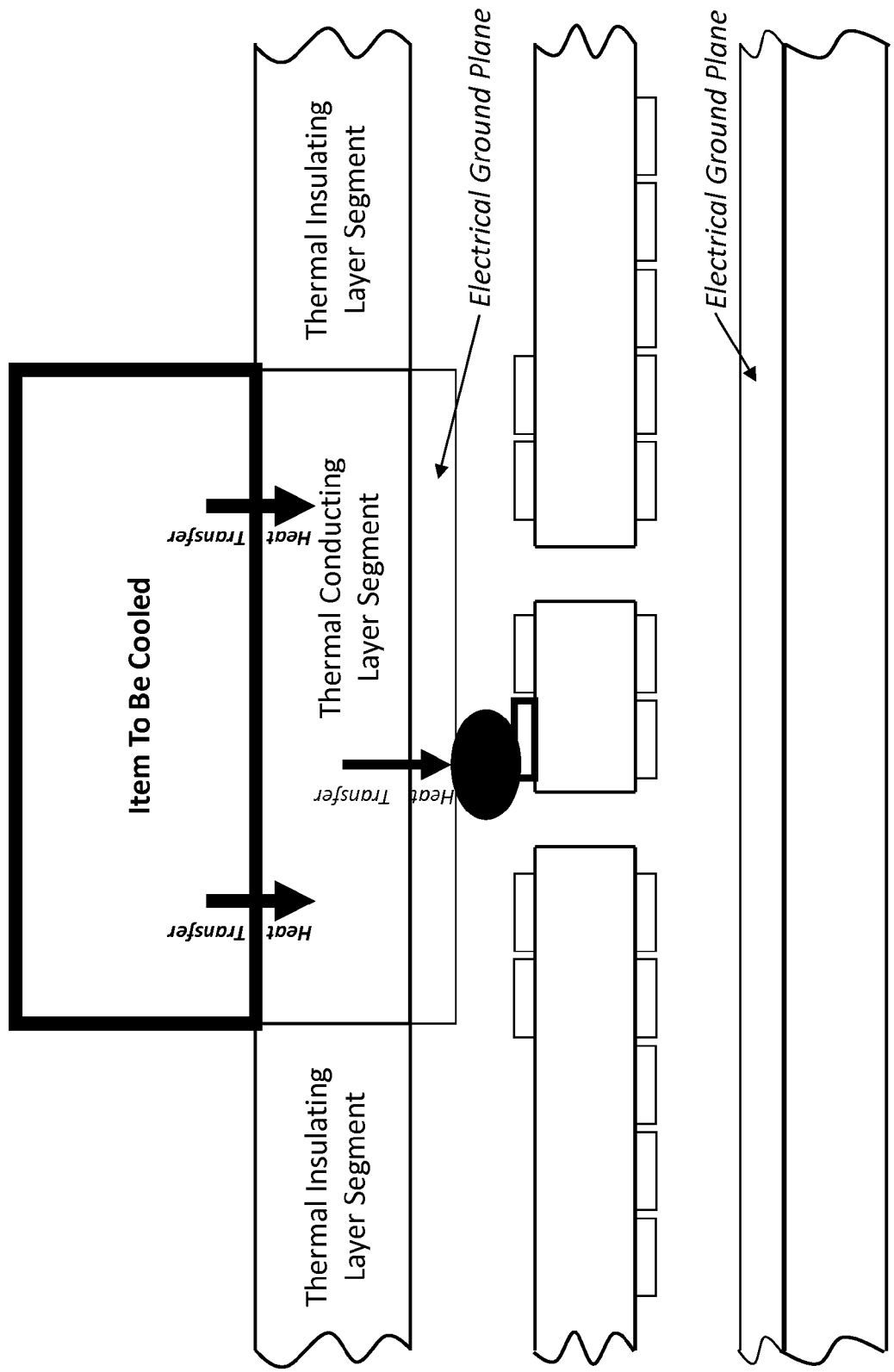
Figure 21B:
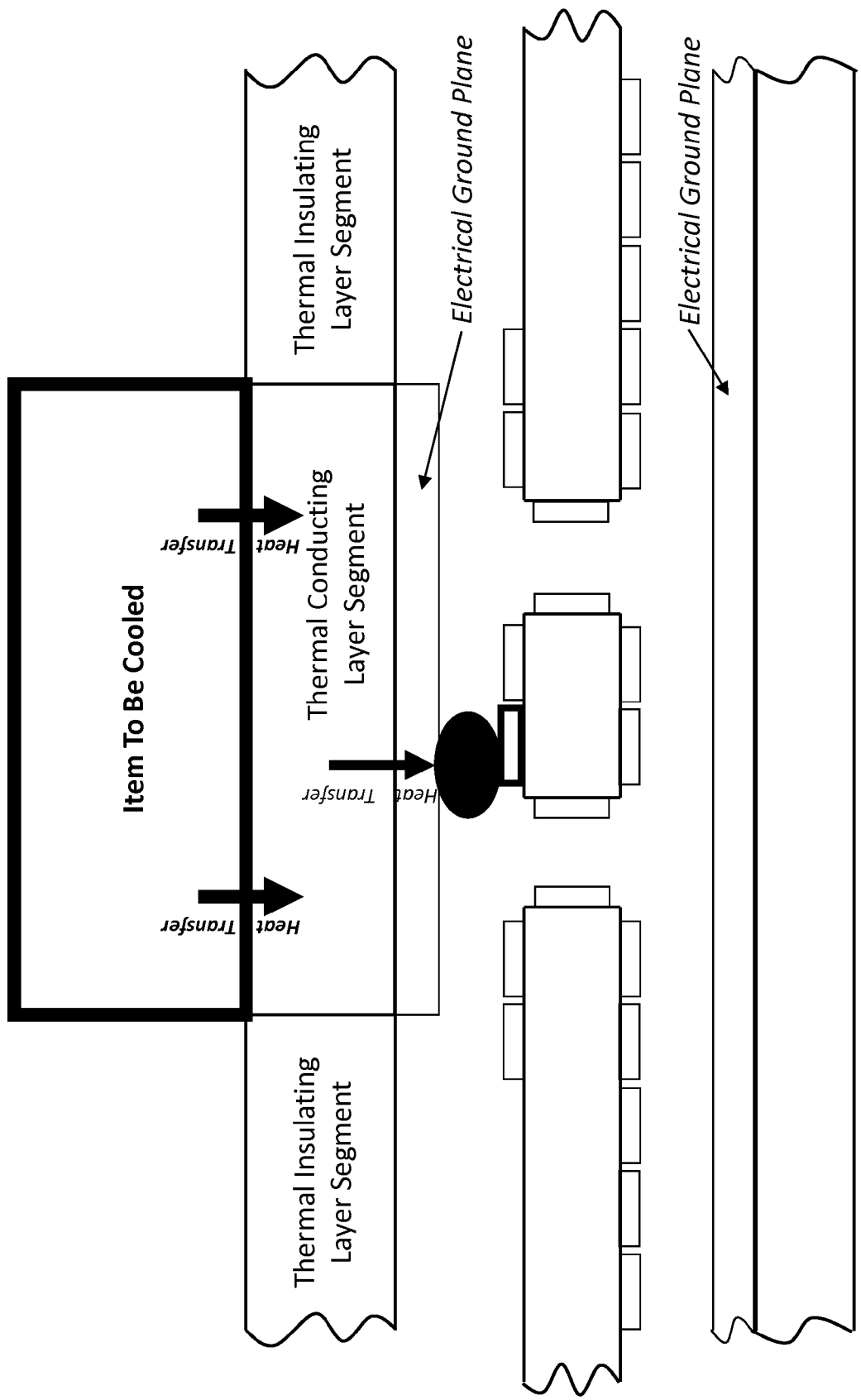
Figure 22A:
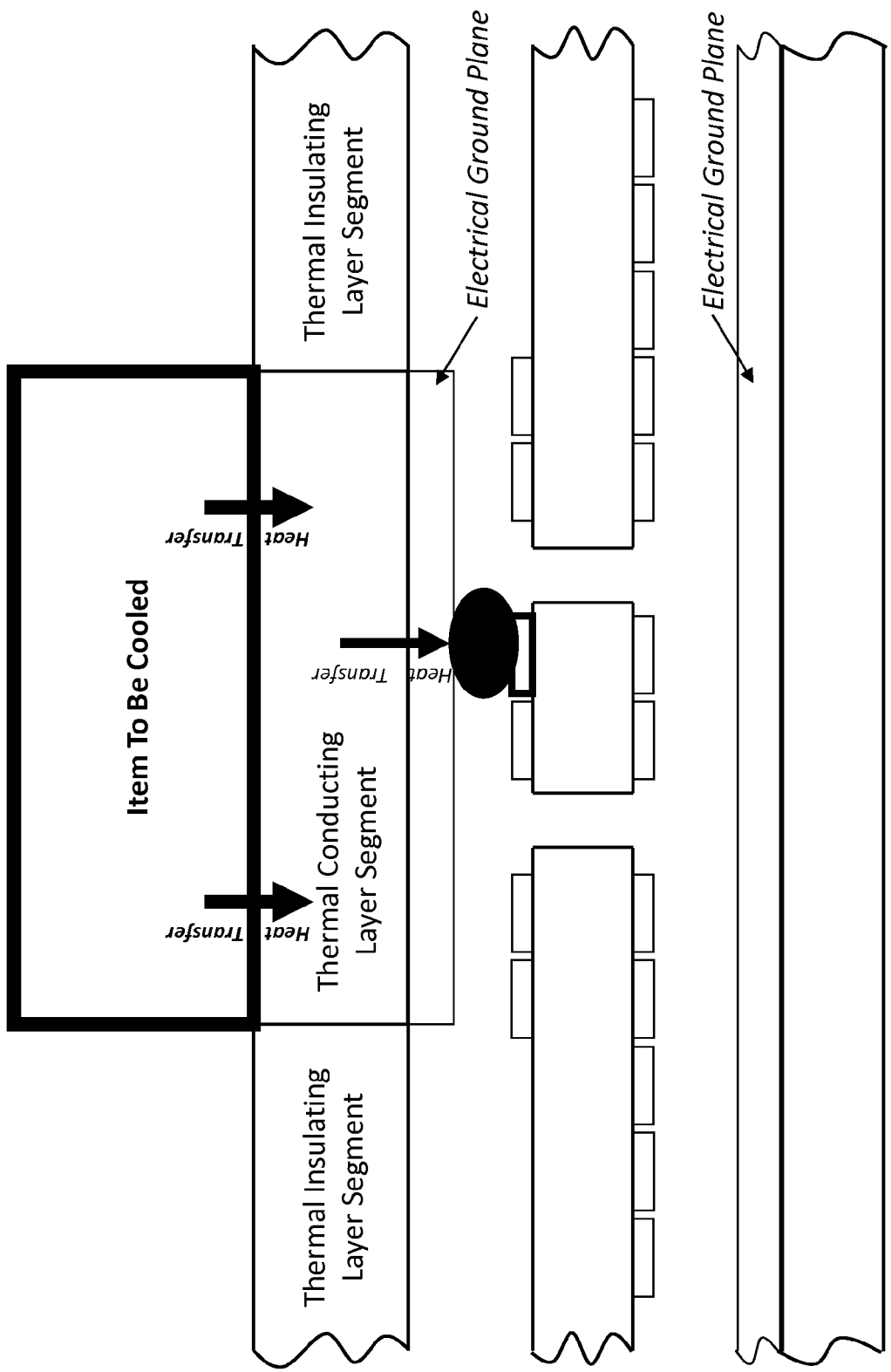
Figure 22B:
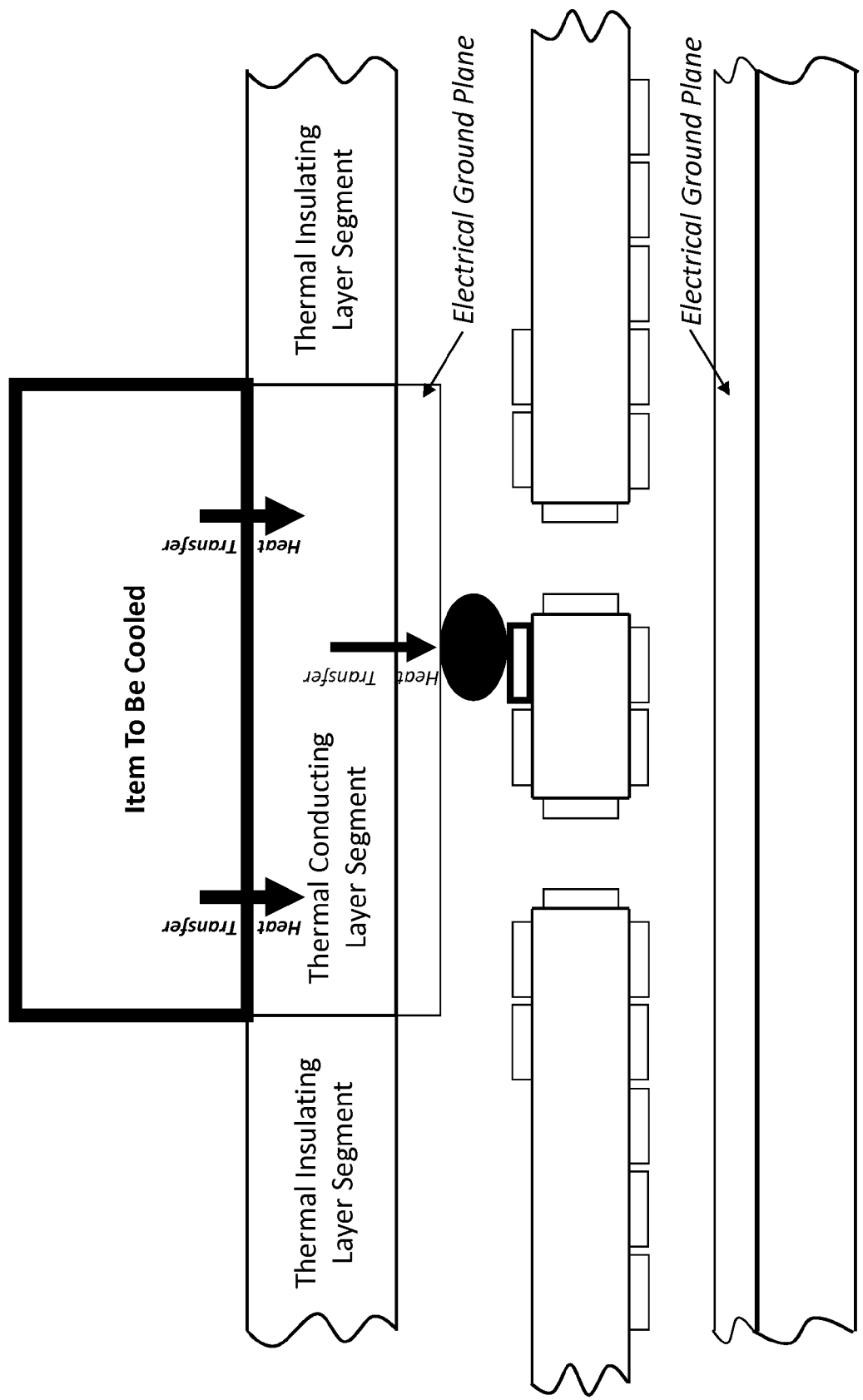
Figure 23A:
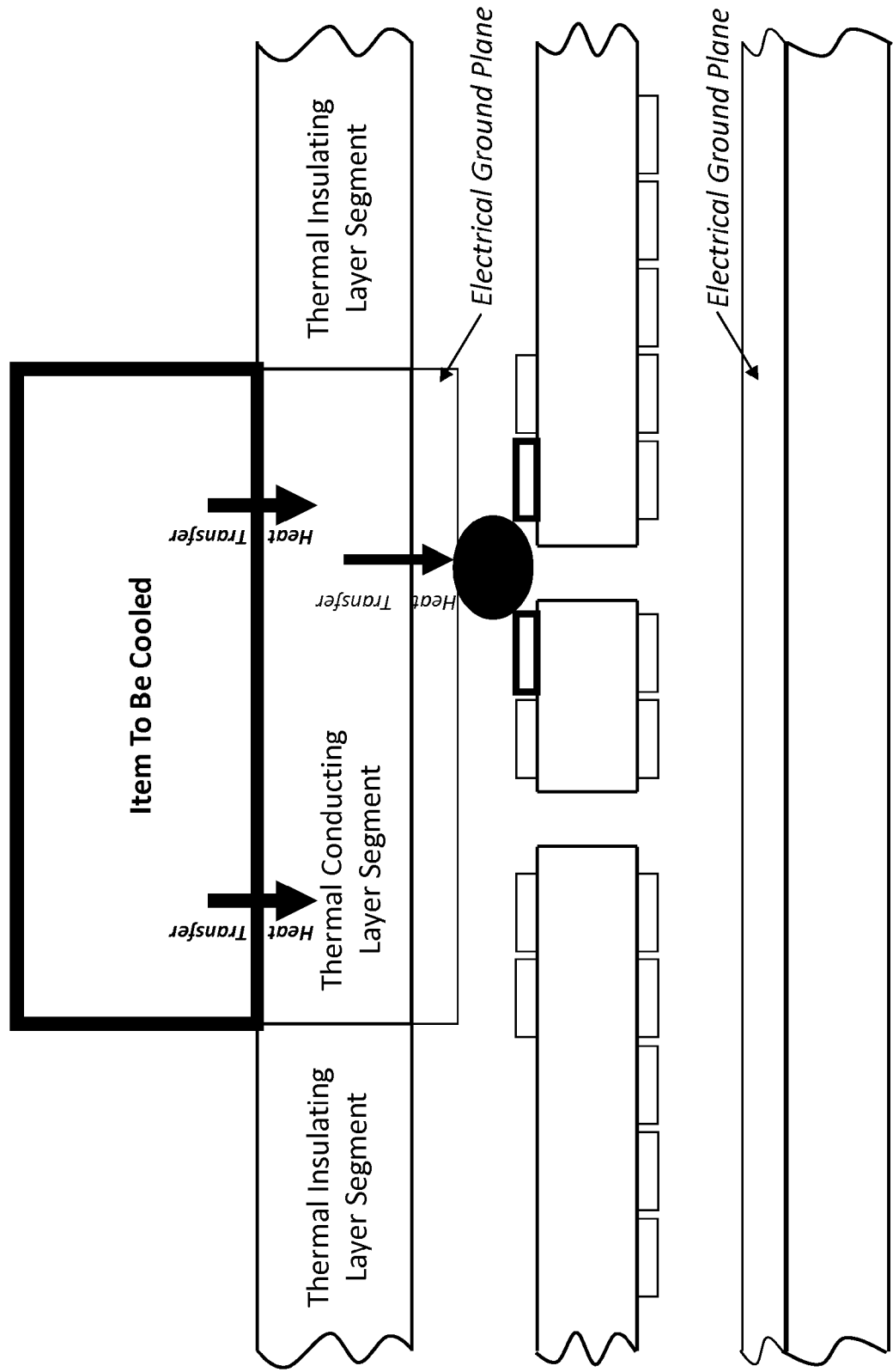
Figure 23B:
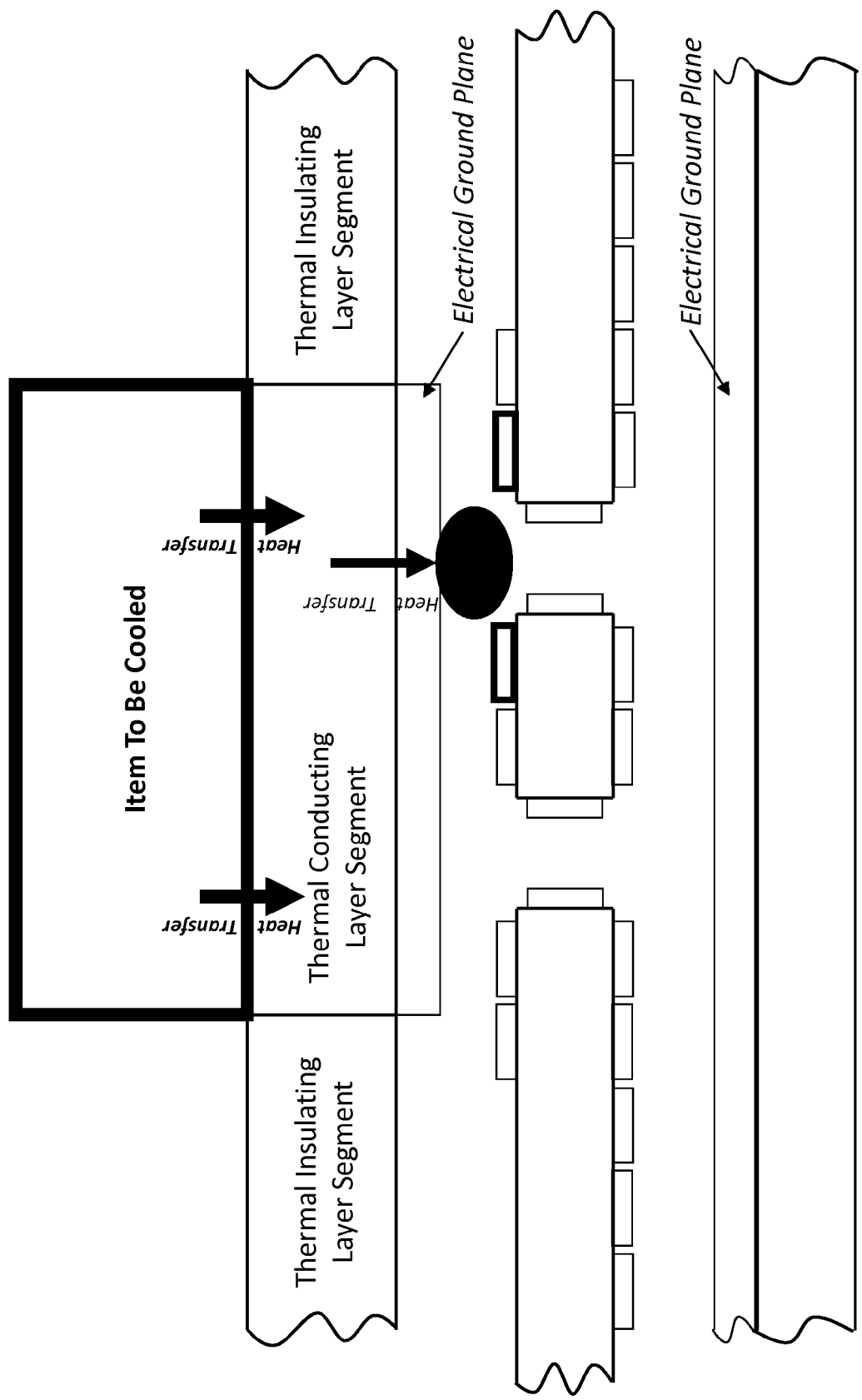
Figure 23C:
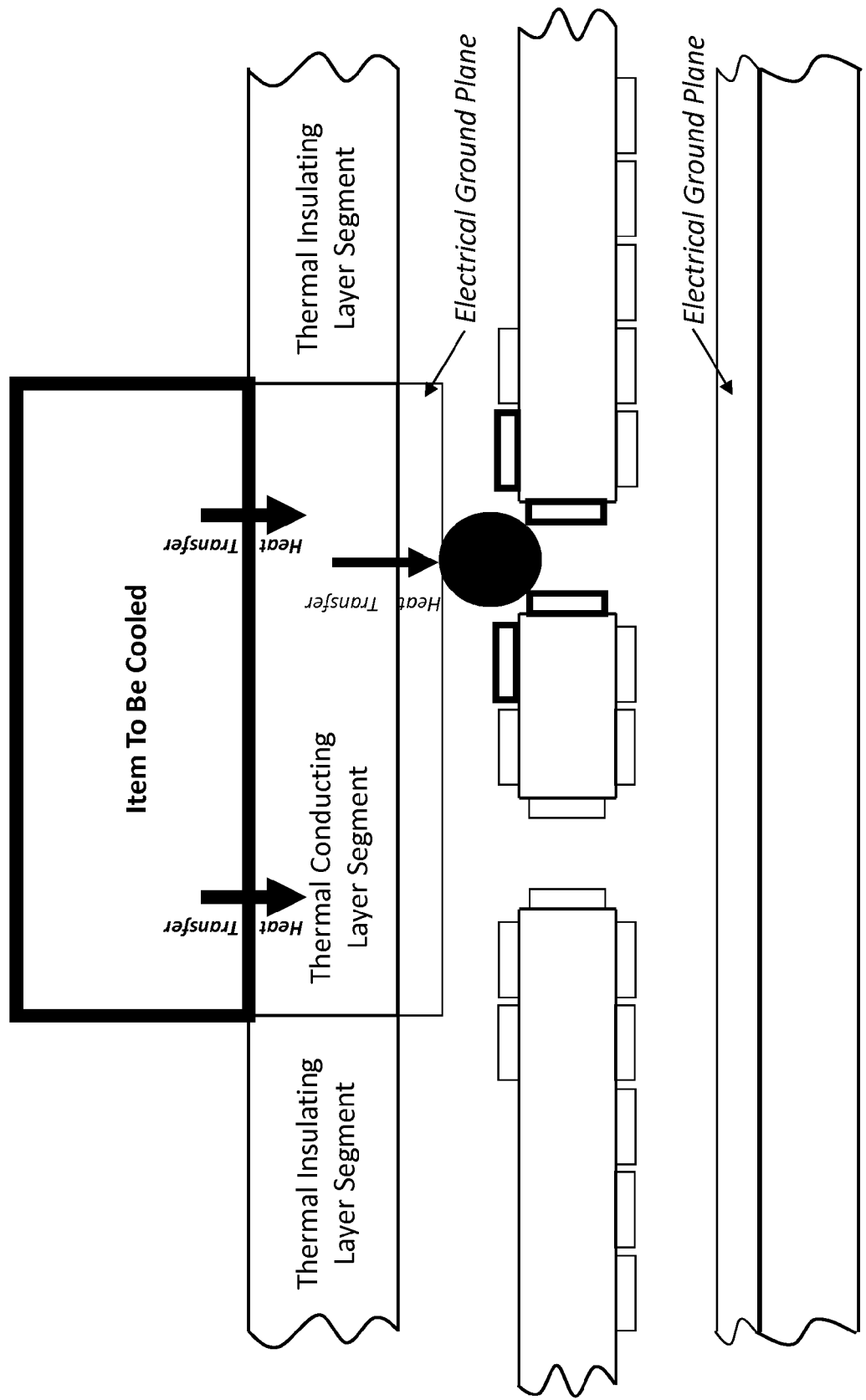
Figure 24A:
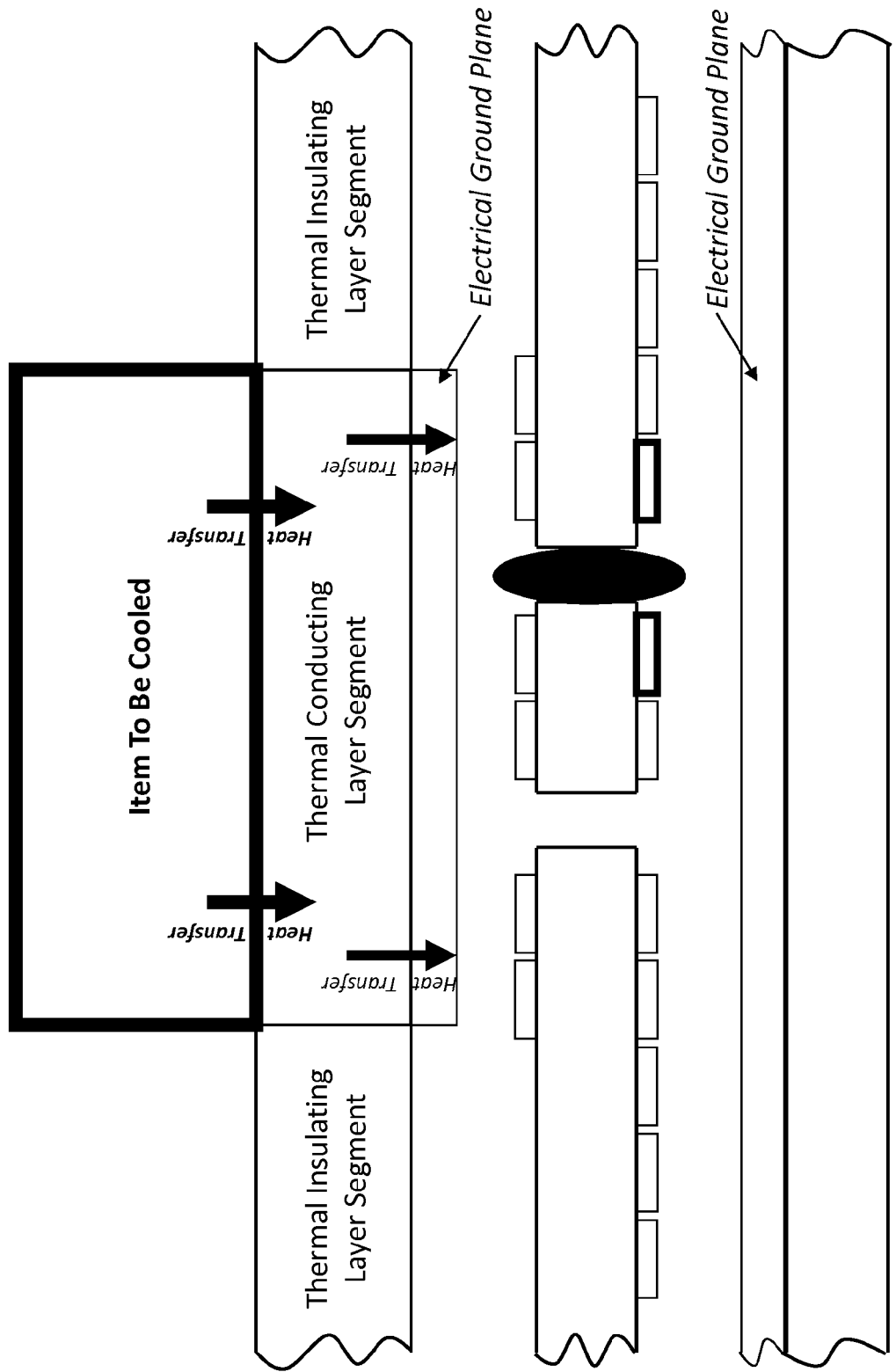
Figure 24B:
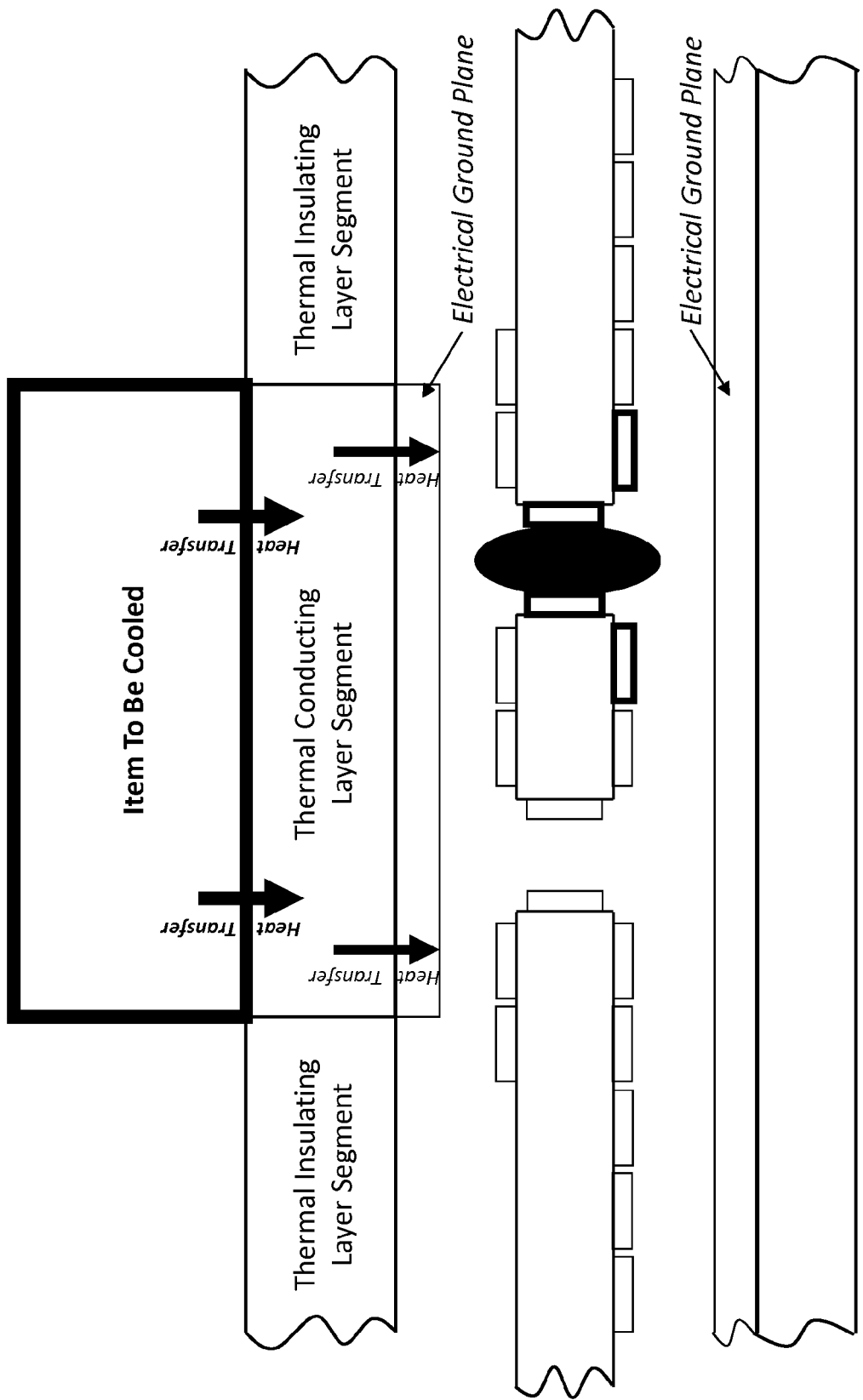
Figure 25A:
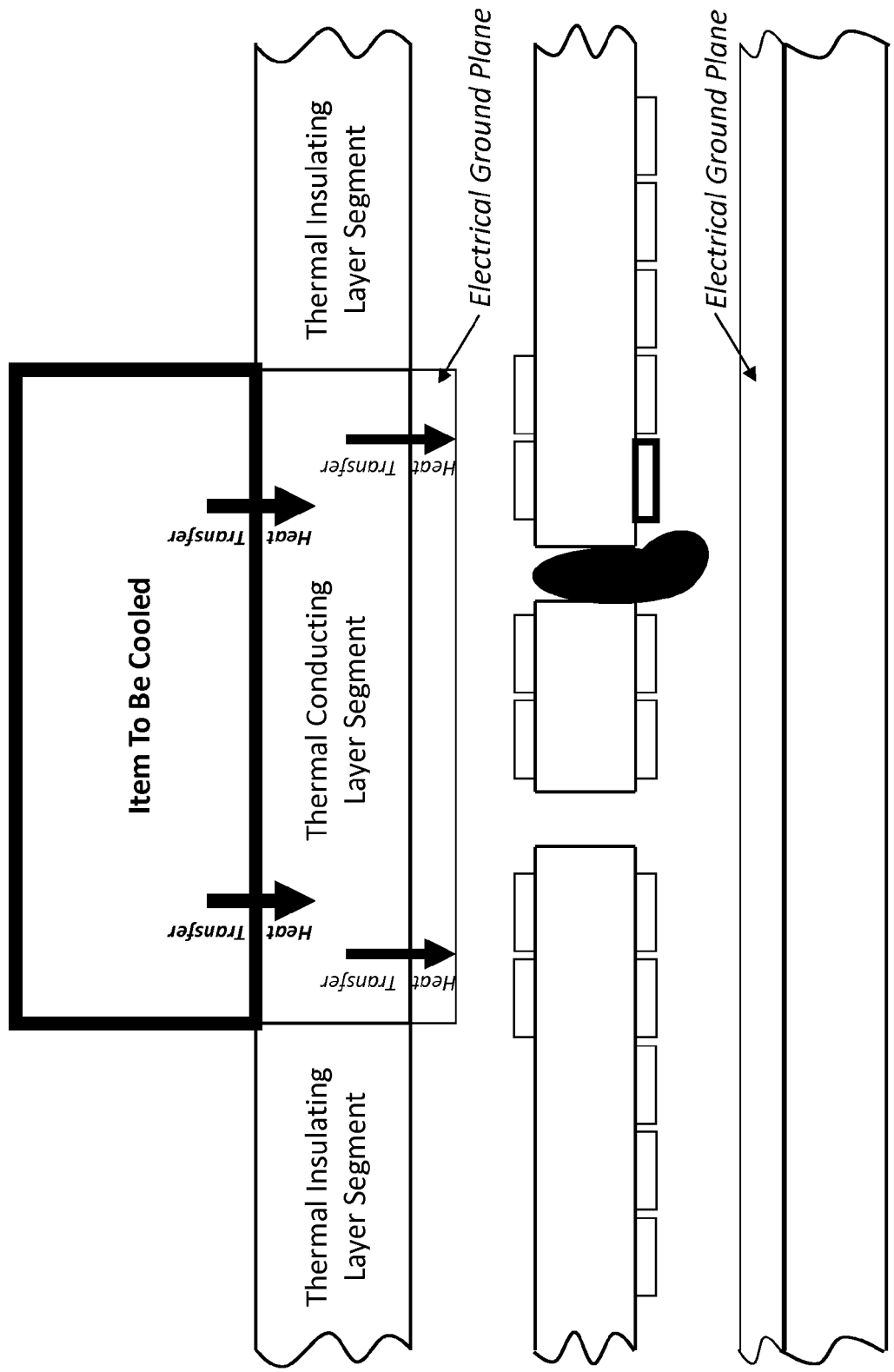
Figure 25B:
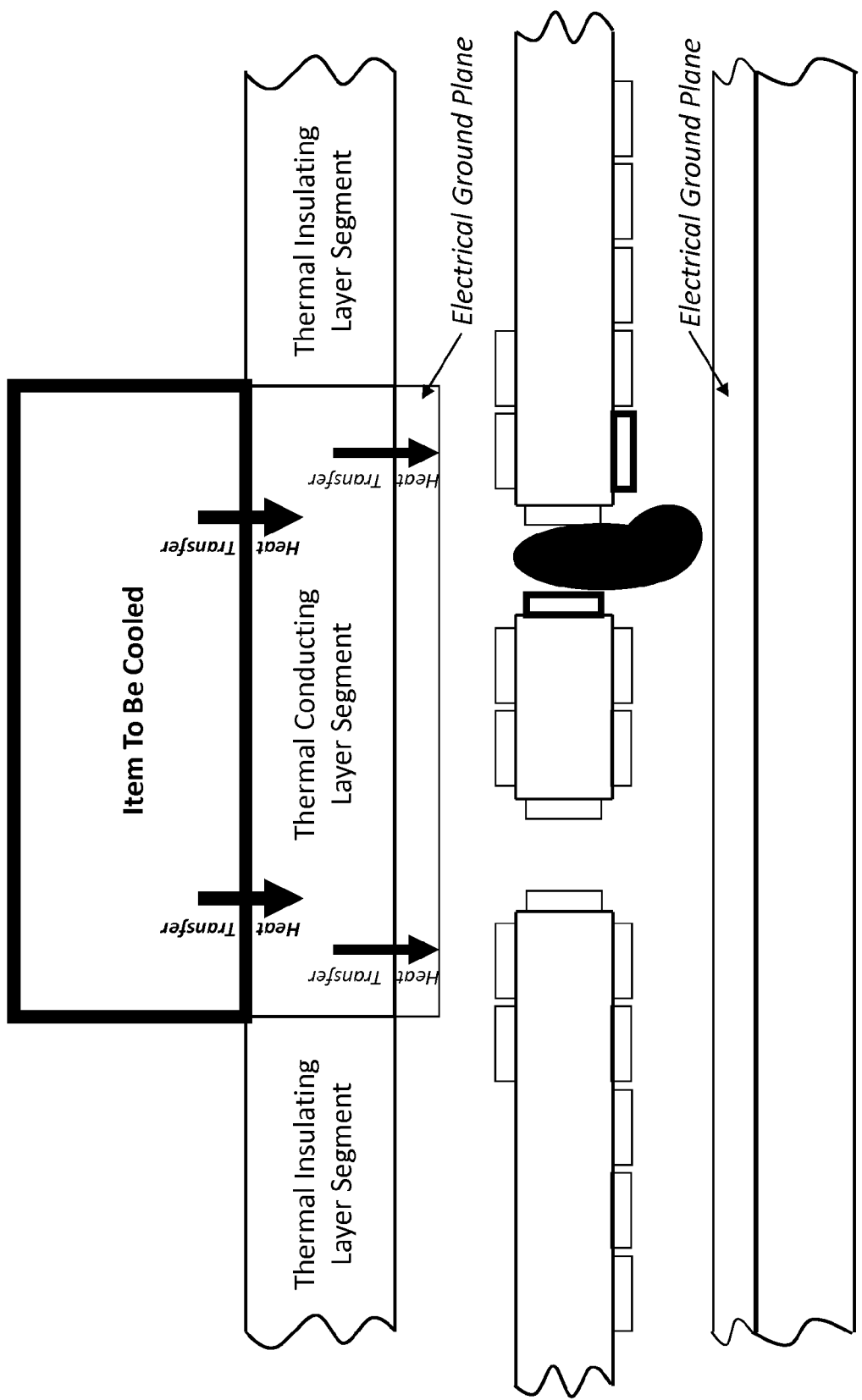
Figure 25C:
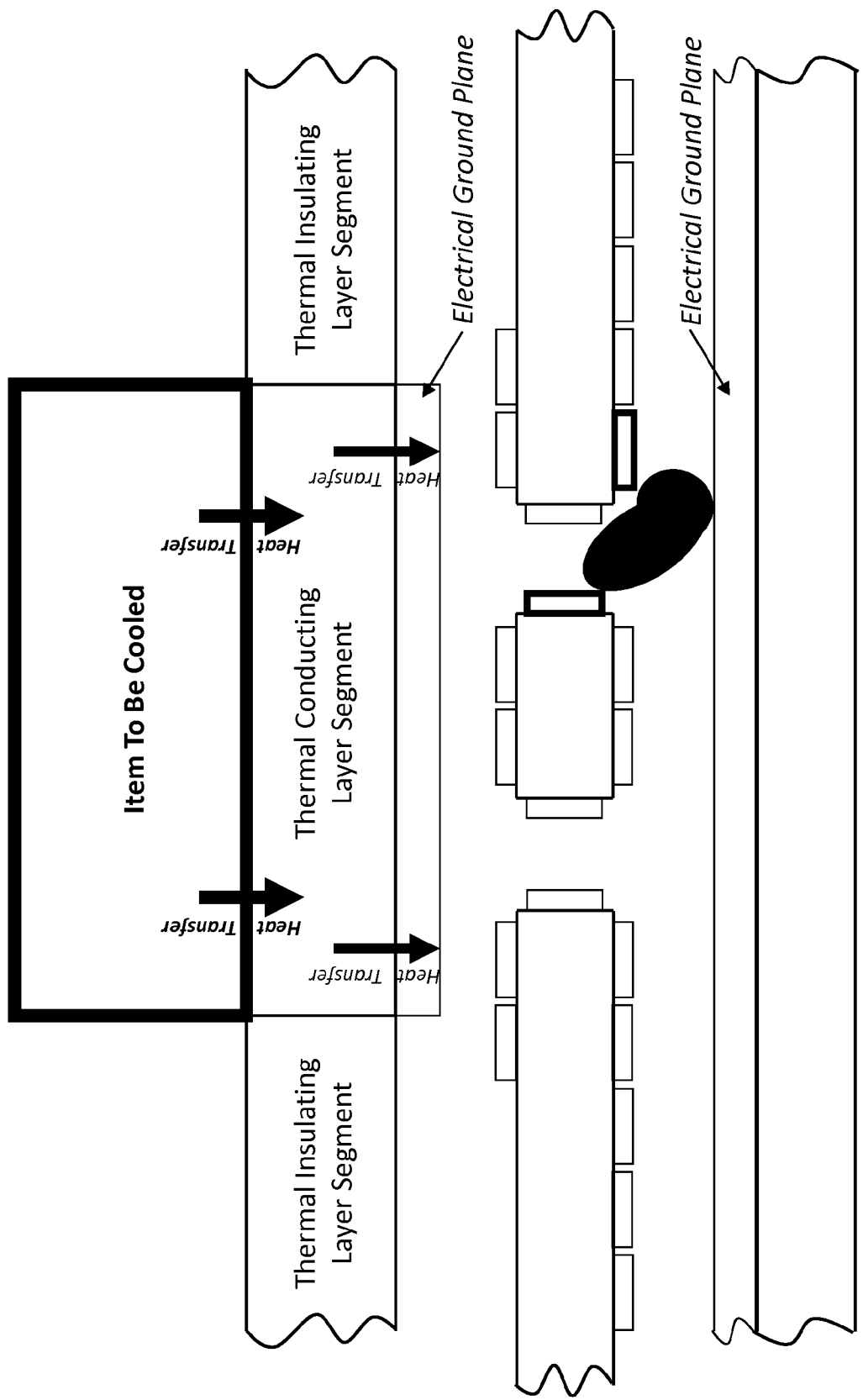

Example Micro-Droplet Transport Through Conduits into and from Heated Transport Region FIG. 17 depicts an example alternative to the course represented by FIG. 16, herein where the momentum of the micro-droplet is suppressed by the simultaneous activation of the microelectrodes on either side of the conduit joining the lower micro-droplet transport region and the upper micro-droplet transport region and maintaining this condition for an adequate length of time for the micro-droplet to recover from the depicted motion and (via surface tension or other droplet-maintaining processes and forces) settle into a stable position under the depicted activated electrode.

FIGS. 18a-18b, 19a-19b, 20a-20d, 21a-21b, 22a-22b, 23a-23c, 24a-24b, and 25a-25c depict two alternative arrangements for transmission through a first conduit joining two droplet-transport layers from a non-heat-gathering-layer to a heat-gathering-layer and transmission through a second conduit joining the two droplet-transport regions so as to return to a non-heat-gathering-layer. As a first example, the sequence depicted in the series of FIGS. 18a, 19a, 20a, 21a, 22a, 23a, 24a, and 25a depict example transmission employing a component of capillary forces and electric fields from distant microelectrodes. Other approaches differing in various ways from that depicted in this series of figures can also be used and are anticipated in the example embodiments.

Alternatively, microelectrodes can be provided in the conduits to facilitate precise electrowetted transport, while comparatively the sequence depicted in the series of FIGS. 18b, 19b, 20b, 20c, 20d, 21b, 22b, 23b, 23c, 24b, 25b, and 25c depict example transmission through the first and second microelectrode-including conduits joining the two droplet-transport layers, wherein the transmission through the conduits employs essentially only proximate microelectrodes. The microelectrodes can be implemented within the conduits through a variety of ways, including insertion of prefabricated cylindrical structures within the conduits. Further, the voltage potential applied to microelectrodes within the conduit in various implementations and transport schemes take on different values over time, for example sometime the electrowetted transport voltage potential and sometimes the ground plane voltage potential. In some implementations and transport schemes, other voltage potentials can also or alternatively be used so as to manipulate the path and shape of the micro-droplet as advantageous. Other approaches differing in various ways from that depicted in this series of figures can also be used and are anticipated in the example embodiments.

While in the upper transport region (FIGS. 21a-b, 22a-22b, 23a-23c) the micro-droplet absorbs heat generated by the item to be cooled through the thermal conducting layer segment and electrical ground plane, or via other arrangements in alternate implementations. The absorbed heat in the resulting heated micro-droplets can then be transported to other regions where the heat can be processed in various ways (as in the examples to be described as well as other ways applicable to various applications and/or alternate embodiments).

Example Continued Micro-Droplet Transport Through Non-Heated Transport Region

Figure 26:
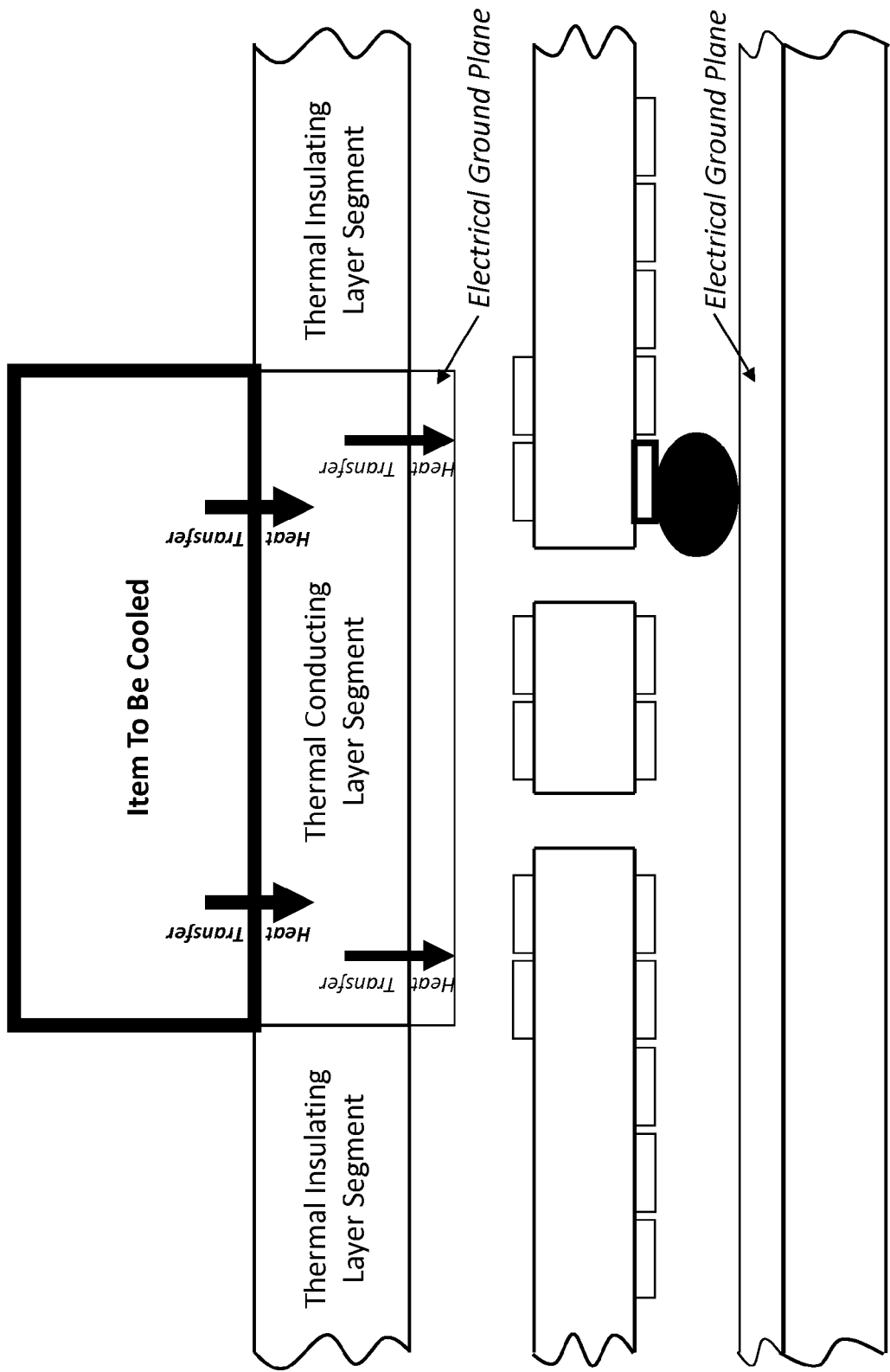
FIG. 26 depicts the attraction of the micro-droplet to a region immediately to the right of the second conduit joining the two droplet-transport regions via activation of the microelectrode immediately to the right of the second conduit joining the two droplet-transport regions.

FIG. 26 depicts the attraction of the micro-droplet to a region immediately to the right of the second conduit joining the two droplet-transport regions via activation of the microelectrode immediately to the right of the second conduit joining the two droplet-transport regions. The situation depicted in FIG. 26 can occur immediately after the situation depicted in FIG. 16, or immediately after the situation depicted in FIG. 25a, or immediately after the situation depicted in FIG. 25c. Other strategies for sequencing the voltage potentials applied to the microelectrodes involved are also possible and provided for in various implementations.

Figure 27:
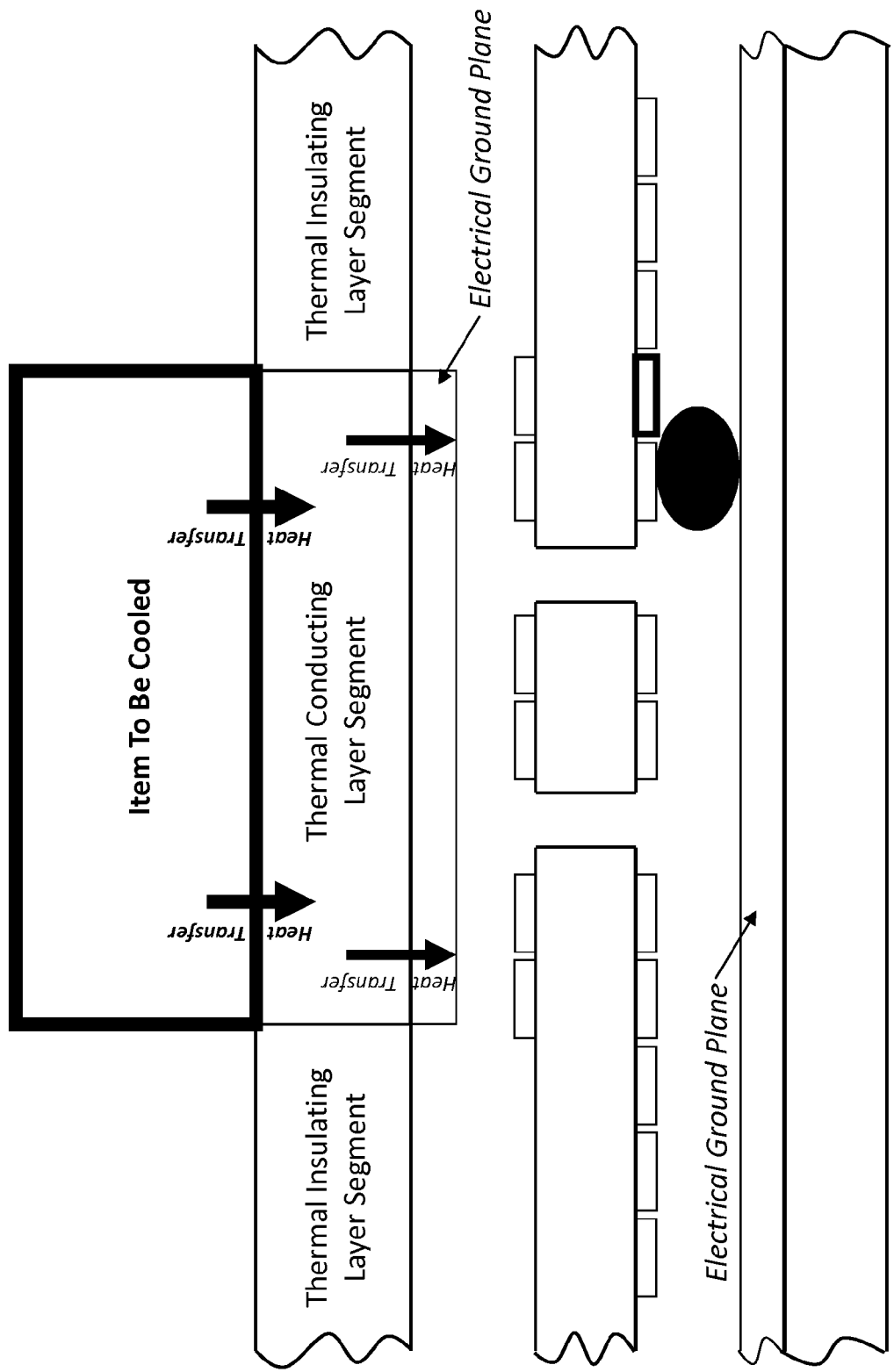
FIG. 27 depicts the attraction of the micro-droplet towards the next microelectrode by activation of that microelectrode.

FIG. 27 depicts the attraction of the micro-droplet towards the next microelectrode by activation of that microelectrode.

Figure 28:
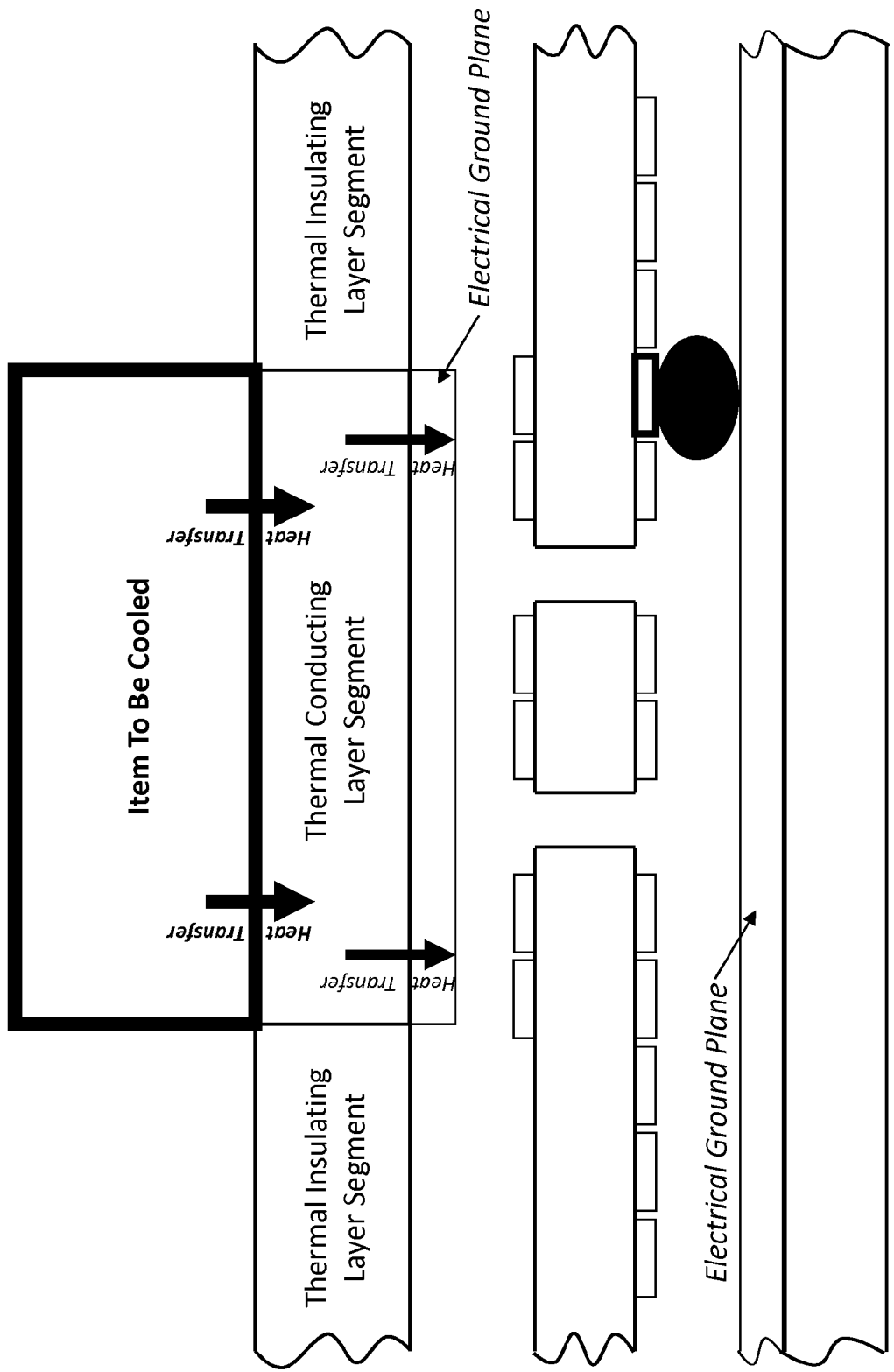
FIG. 28 can depict an arrangement for the suppression of micro-droplet momentum by locking it into position under the activated microelectrode for an interval of time.

FIG. 28 can depict an arrangement for the suppression of micro-droplet momentum by locking it into position under the activated microelectrode for an interval of time. FIG. 28 can also depict a transient situation of micro-droplet transport wherein the momentum of the micro-droplet is not suppressed (i.e., the micro-droplet is not locked into position under the activated microelectrode for an interval of time).

Figure 29:
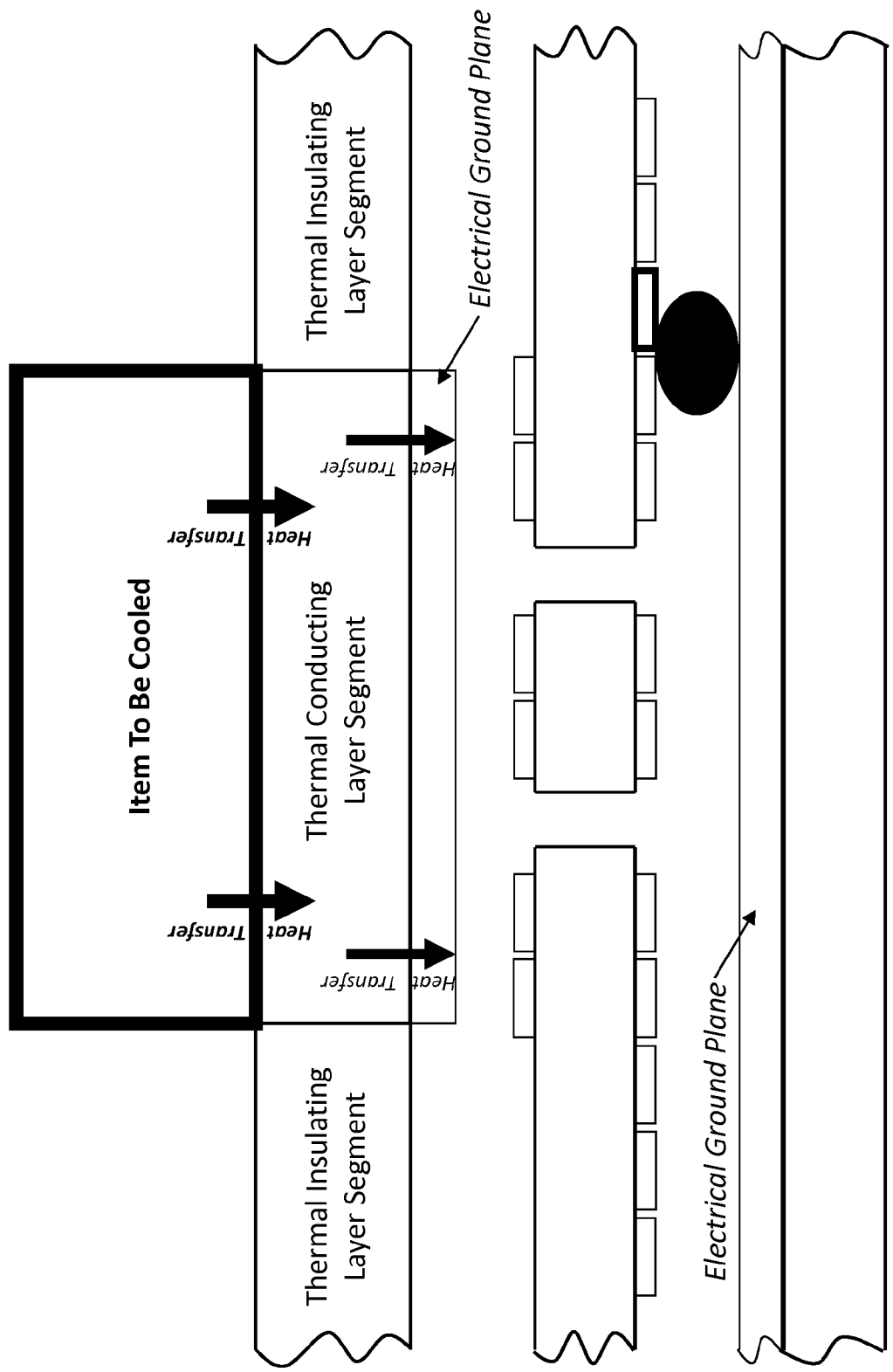
FIG. 29 depicts the attraction of the micro-droplet towards the next microelectrode by activation of that microelectrode.

FIG. 29 depicts the attraction of the micro-droplet towards the next microelectrode by activation of that microelectrode.

Figure 30:
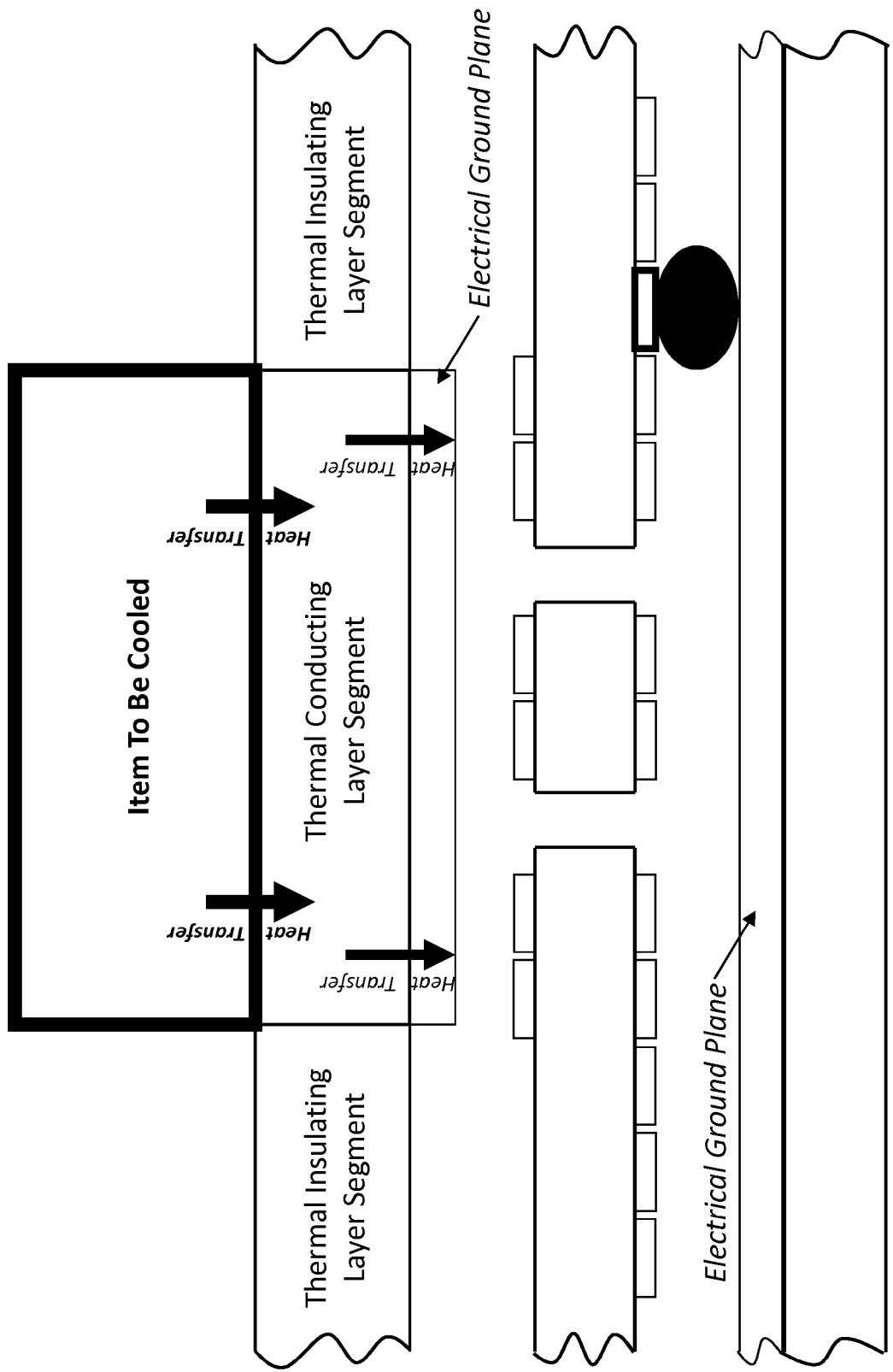
FIG. 30 can depict an arrangement for the suppression of micro-droplet momentum by locking it into position under the activated microelectrode for an interval of time.

FIG. 30 can depict an arrangement for the suppression of micro-droplet momentum by locking it into position under the activated microelectrode for an interval of time. FIG. 30 can also depict a transient situation of micro-droplet transport wherein the momentum of the micro-droplet is not suppressed (i.e., the micro-droplet is not locked into position under the activated microelectrode for an interval of time).

Figure 31:
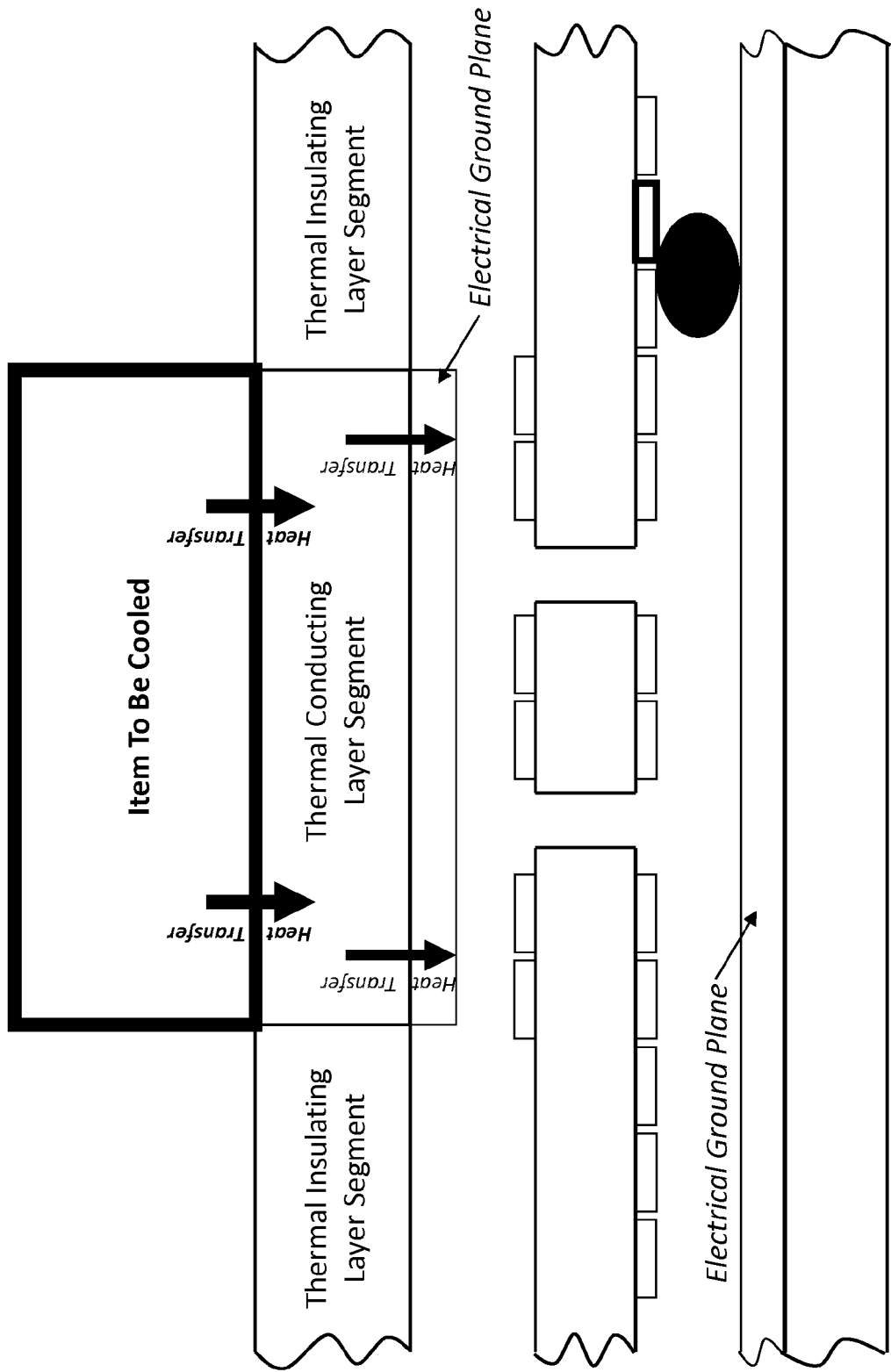
FIG. 31 depicts the attraction of the micro-droplet towards the next microelectrode by activation of that microelectrode.

FIG. 31 depicts the attraction of the micro-droplet towards the next microelectrode by activation of that microelectrode.

Figure 32:
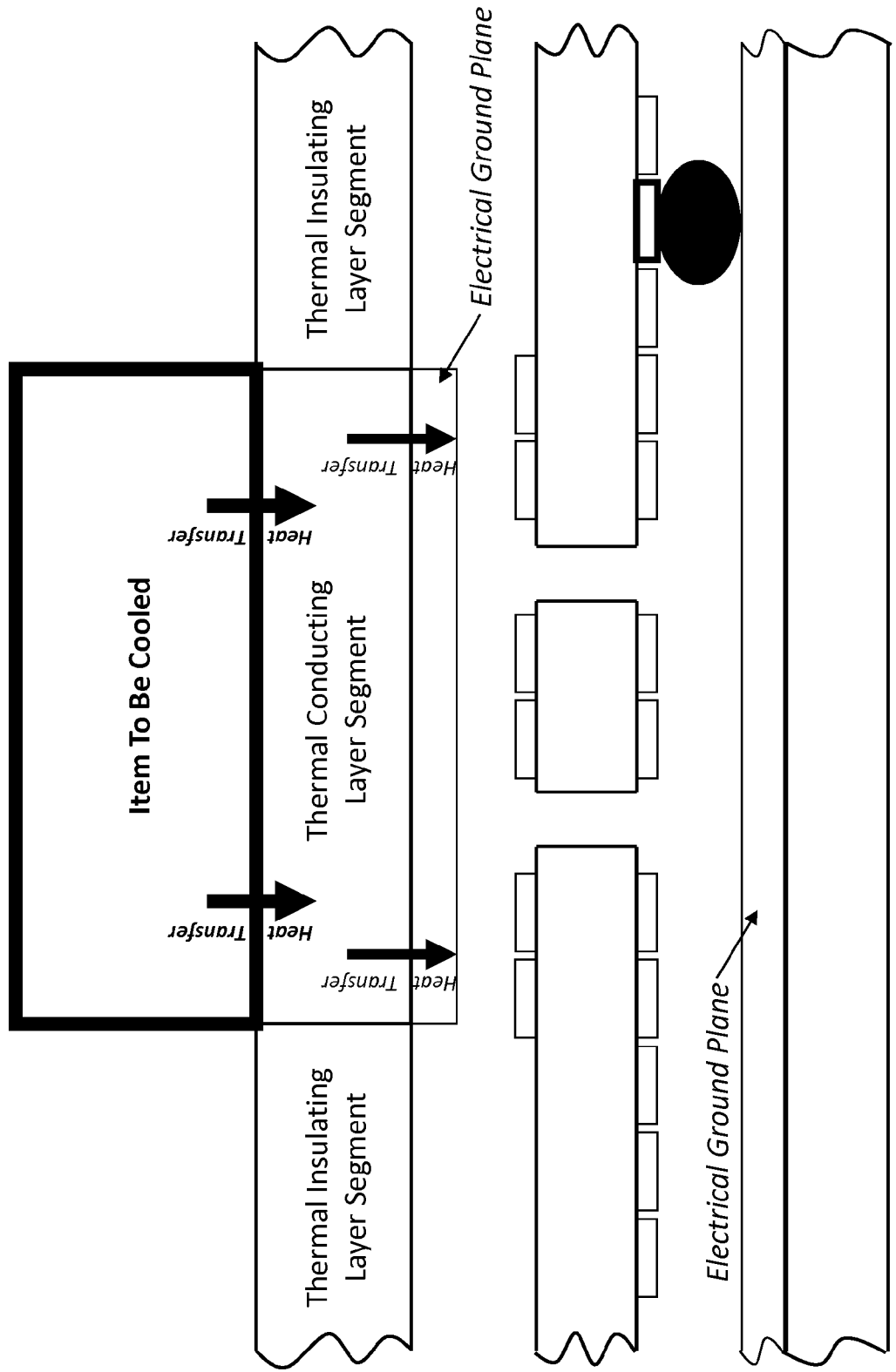
FIG. 32 can depict an arrangement for the suppression of micro-droplet momentum by locking it into position under the activated microelectrode for an interval of time.

FIG. 32 can depict an arrangement for the suppression of micro-droplet momentum by locking it into position under the activated microelectrode for an interval of time. FIG. 30 can also depict a transient situation of micro-droplet transport wherein the momentum of the micro-droplet is not suppressed (i.e., the micro-droplet is not locked into position under the activated microelectrode for an interval of time).

Thermodynamic Models Abstracting Various Types of Thermal Transfer from Heated Micro-Droplets FIG. 33 depicts a general thermodynamics passive heat transfer process from a hot body to a broader environment.

Figure 34B:
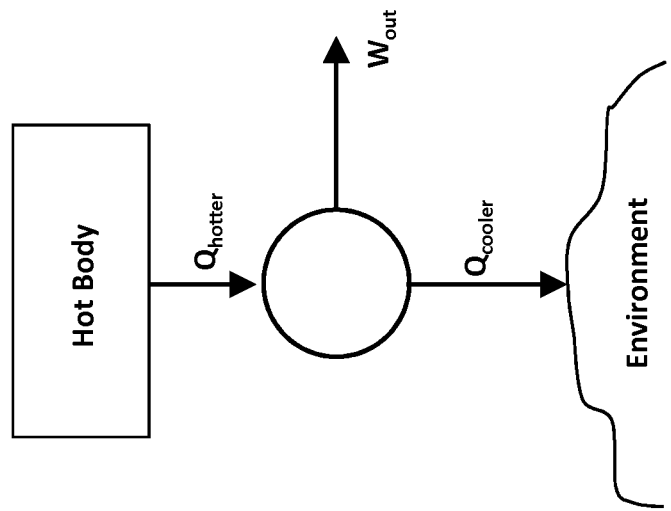
FIG. 34b depicts a heat engine arrangement for an active heat transfer process from a hot body to a broader environment. Energy is harvested over time by the heat engine (amounting to harvested work) and consumed (at least in part) by external processes.
Figure 34A:
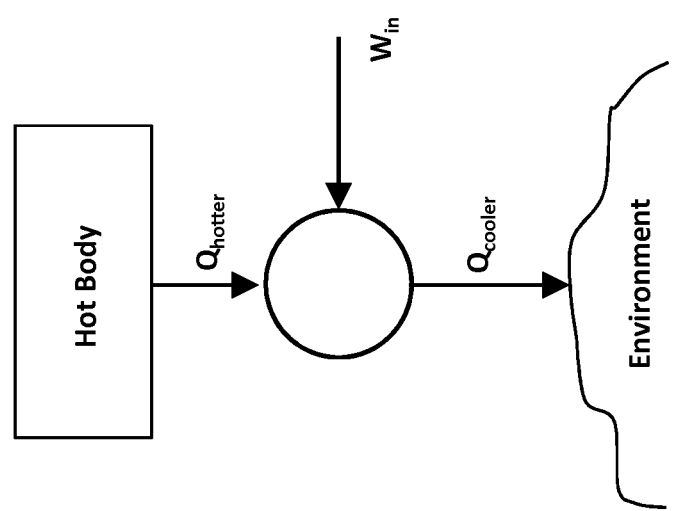
FIG. 34a depicts a heat pump arrangement for an active heat transfer process from a hot body to a broader environment. Energy is applied over time to the heat pump (amounting to applied work) and consumed in the heat-pumping process.

FIG. 34a depicts a heat pump arrangement for an active heat transfer process from a hot body to a broader environment. Energy is applied over time to the heat pump (amounting to applied work) and consumed in the heat-pumping process. Thermoelectric cooling (for example employing the Peltier process and analogous processes employing Avto metals and quantum well materials) is an example of such a heat pump arrangement. Additional considerations relating to the energy and work applied to the heat pump (for example Thomson effect, Joule heating, etc.) are not brought forth in this representation.

FIG. 34b depicts a heat engine arrangement for an active heat transfer process from a hot body to a broader environment. Energy is harvested over time by the heat engine (amounting to harvested work) and consumed (at least in part) by external processes. Thermoelectric electric current generation (for example employing the Seebeck process and analogous processes employing Avto metals and quantum well materials) is an example of such a heat engine arrangement. Additional considerations relating to the energy and work applied to the heat engine (for example Benedicks effect, Joule heating, etc.) are not brought forth in this representation.

Example Micro-Droplet Thermal Transfer within Non-Heated Transport Region

FIG. 35a depicts a representation of heat transfer from the previously heated micro-droplet to the electrical ground plane.

FIG. 35b depicts a representation of heat transfer from the previously heated micro-droplet to the electrical ground plane and further into the material joined to the electrical ground plane.

FIG. 35c depicts a representation of heat transfer from the previously heated micro-droplet to the electrical ground plane and further into a local thermal conducting structure joined to the electrical ground plane.

Each of the situations depicted in FIGS. 35a-35c are special cases of the abstract representation depicted in FIG. 33.

Example Micro-Droplet Thermal Transfer To Thermoelectric Devices in the Non-Heated Transport Region and Resultant Capabilities FIG. 36 depicts a variation on the arrangement of FIG. 35b wherein the material joined to the electrical ground plane comprises a "global" (large area) thermoelectric structure. In various embodiments the thermoelectric structure can be a thermoelectric cooler (an "electrical" case of the abstract heat pump representation depicted in FIG. 34a), a thermoelectric electric current generator (an "electrical" case of the abstract heat engine representation depicted in FIG. 34b), or a reciprocal thermoelectric device capable of operating in either a thermoelectric cooler (i.e., an "electrical" heat pump) or a thermoelectric electric current generator (i.e., an "electrical" heat engine) as determined by imposed thermal conditions and electrical connections to the reciprocal thermoelectric device. In an embodiment, the role of electrical ground plane (used for micro-droplet transport) can be served by the electrical conditions and physical location of a portion of the thermoelectric device itself (such as electrically conducting material joining two legs of the thermoelectric device). In some embodiments, the role of electrical shielding (from electrical field and electromagnetic generation noise) can also be served by the electrical conditions and physical location of the same portion of the thermoelectric device itself. In other embodiments, the role of electrical shielding can also be served by the electrical conditions and physical location of another portion of the thermoelectric device itself. In yet other embodiments, the role of electrical shielding can also be served by another electrical shielding element.

FIG. 37 depicts a variation on the arrangements of FIG. 35c and FIG. 36 combining features from each, wherein heat is transferred from the previously heated micro-droplet to a local (small area) thermoelectric structure. In various embodiments the thermoelectric structure can be a thermoelectric cooler, a thermoelectric electric current generator, or a reciprocal thermoelectric device capable of operating in either a thermoelectric cooler or a thermoelectric electric current generator as determined by imposed thermal conditions and electrical connections to the reciprocal thermoelectric device. In an embodiment, the role of electrical ground plane (used for micro-droplet transport) can be served by the electrical conditions and physical location of a portion of the thermoelectric device itself (such as electrically conducting material joining two legs of the thermoelectric device). In some embodiments, the role of electrical shielding (from electrical field and electromagnetic generation noise) can also be served by the electrical conditions and physical location of the same portion of the thermoelectric device itself. In other embodiments, the role of electrical shielding can also be served by the electrical conditions and physical location of another portion of the thermoelectric device itself. In yet other embodiments, the role of electrical shielding can also be served by another electrical shielding element.

Additionally, in some embodiments, the thermoelectric device can serve as a temperature sensor.

In some embodiments, the mode of the thermoelectric device is switched over time. As one example, the thermoelectric device can be a thermoelectric cooler one moment and a temperature sensor at another moment. As another example, the thermoelectric device can be a thermoelectric electric current generator one moment and a temperature sensor at another moment. As yet another example, the thermoelectric device can be a thermoelectric cooler one moment and a thermoelectric electric current generator at another moment. As still another example, the thermoelectric device can be a thermoelectric cooler one moment, a temperature sensor at another moment, and a thermoelectric electric current generator at yet another moment.

FIG. 38 depicts a variation on the arrangement of FIG. 35b comprising a plurality of local (small area) thermoelectric structures. In an embodiment, each local thermoelectric structure can separately attend to processing heat from properly positioned previously heated micro-droplet. In an embodiment, the role of electrical ground plane can be served by the electrical conditions and physical location of a portion of the thermoelectric device itself (such as electrically conducting material joining two legs of the thermoelectric device), and the individual portion of each of the plurality of thermoelectric devices collectively serve as an electrical equivalent to an electrical ground plane used for micro-droplet transport. In some embodiments, the role of electrical shielding (from electrical field and electromagnetic generation noise) can also be served by the electrical conditions and physical location of the same portion of the thermoelectric device itself. In other embodiments, the role of electrical shielding can also be served by the electrical conditions and physical location of another portion of the thermoelectric device itself. In yet other embodiments, the role of electrical shielding can also be served by another electrical shielding element. In various embodiments, each of the local thermoelectric structures can be a thermoelectric cooler, a thermoelectric electric current generator, or a reciprocal thermoelectric device capable of operating in either a thermoelectric cooler or a thermoelectric electric current generator as determined by imposed thermal conditions and electrical connections to the reciprocal thermoelectric device.

In some embodiments, all of the local thermoelectric structures are thermoelectric coolers. In other embodiments, all of the local thermoelectric structures are thermoelectric electric current generators.

In yet other embodiments, each of the local thermoelectric structures are reciprocal thermoelectric devices capable of operating in either a thermoelectric cooler or a thermoelectric electric current generator as determined by imposed thermal conditions and electrical connections to the reciprocal thermoelectric device. In some implementations of such (i.e., all reciprocal thermoelectric device) embodiments, all local thermoelectric structures are used in the same mode at the same time. In other implementations of such (i.e., all reciprocal thermoelectric device) embodiments, a first plurality of local thermoelectric structures are used in thermoelectric cooler mode at the same time that a second non-overlapping plurality of local thermoelectric structures are used in thermoelectric electric current generator mode. In yet other implementations of such (i.e., all reciprocal thermoelectric device) embodiments, each of the local thermoelectric structures are reciprocal thermoelectric devices is configured to be independently operable in either a thermoelectric cooler or a thermoelectric electric current generator as determined by imposed thermal conditions and electrical connections to the reciprocal thermoelectric device.

Additionally, in some embodiments, at least one of the thermoelectric devices can serve as a temperature sensor.

In some embodiments, the mode of a given thermoelectric device is switched over time. As one example, a given thermoelectric device can be a thermoelectric cooler one moment and a temperature sensor at another moment. As another example, a given thermoelectric device can be a thermoelectric electric current generator one moment and a temperature sensor at another moment. As yet another example, a given thermoelectric device can be a thermoelectric cooler one moment and a thermoelectric electric current generator at another moment. As still another example, a given thermoelectric device can be a thermoelectric cooler one moment, a temperature sensor at another moment, and a thermoelectric electric current generator at yet another moment.

FIG. 39 depicts an expanding variation on the arrangement of FIG. 38 wherein the electrical ground plane depicted throughout earlier figures is replaced by an extended array of local thermoelectric structures. In an embodiment, the role of electrical ground plane can be served by the electrical conditions and physical location of a portion of the thermoelectric device itself (such as electrically conducting material joining two legs of the thermoelectric device), and the individual portion of each of the plurality of thermoelectric devices collectively serve as an electrical equivalent to an electrical ground plane used for micro-droplet transport. In some embodiments, the role of electrical shielding (from electrical field and electromagnetic generation noise) can also be served by the electrical conditions and physical location of the same portion of the thermoelectric device itself. In other embodiments, the role of electrical shielding can also be served by the electrical conditions and physical location of another portion of the thermoelectric device itself. In yet other embodiments, the role of electrical shielding can also be served by another electrical shielding element. In various embodiments, each of the local thermoelectric structures can be a thermoelectric cooler, a thermoelectric electric current generator, or a reciprocal thermoelectric device capable of operating in either a thermoelectric cooler or a thermoelectric electric current generator as determined by imposed thermal conditions and electrical connections to the reciprocal thermoelectric device.

In some embodiments, all of the local thermoelectric structures are thermoelectric coolers. In other embodiments, all of the local thermoelectric structures are thermoelectric electric current generators.

In yet other embodiments, each of the local thermoelectric structures are reciprocal thermoelectric devices capable of operating in either a thermoelectric cooler or a thermoelectric electric current generator as determined by imposed thermal conditions and electrical connections to the reciprocal thermoelectric device. In some implementations of such (i.e., all reciprocal thermoelectric device) embodiments, all local thermoelectric structures are used in the same mode at the same time. In other implementations of such (i.e., all reciprocal thermoelectric device) embodiments, a first plurality of local thermoelectric structures are used in thermoelectric cooler mode at the same time that a second non-overlapping plurality of local thermoelectric structures are used in thermoelectric electric current generator mode. In yet other implementations of such (i.e., all reciprocal thermoelectric device) embodiments, each of the local thermoelectric structures are reciprocal thermoelectric devices is configured to be independently operable in either a thermoelectric cooler or a thermoelectric electric current generator as determined by imposed thermal conditions and electrical connections to the reciprocal thermoelectric device.

Additionally, in some embodiments, at least one of the thermoelectric devices can serve as a temperature sensor.

In some embodiments, the mode of a given thermoelectric device is switched over time. As one example, a given thermoelectric device can be a thermoelectric cooler one moment and a temperature sensor at another moment. As another example, a given thermoelectric device can be a thermoelectric electric current generator one moment and a temperature sensor at another moment. As yet another example, a given thermoelectric device can be a thermoelectric cooler one moment and a thermoelectric electric current generator at another moment. As still another example, a given thermoelectric device can be a thermoelectric cooler one moment, a temperature sensor at another moment, and a thermoelectric electric current generator at yet another moment.

Arrangements such as those depicted in FIG. 39 (and to some extent FIG. 38) provide a wide range of capabilities. As one example, local thermoelectric elements on the left side of the figure could remove heat from previously-heated micro-droplets and then send the cooled micro-droplets to the upper level for another cycle of heat gathering. As another example, the duration of a micro-droplets exposure to heat in the upper region can be modulated by the measured temperature of previous heated micro-droplets returning from that particular area of the item to be cooled. As yet another example, local thermoelectric elements on the left side of the figure could pre-cool micro-droplets to below-ambient temperatures and then send the extra-cool micro-droplets to the upper level for a cycle of additional heat gathering. Many other capabilities are made possible by various embodiments, implementations, and adaptations.

Thermal Fluids ("Thermofluids") and Their Conditioning for Droplet Transport in Cooling Applications Thermal fluids (also known as "thermofluids") suitable for heat transport with various performance and physical properties are known, for example propylene glycol, ethylene glycol, various types of oils including various types of liquid polymerized siloxane ("silicone oil"), and specialty thermal fluids, for example such as those sold by Duratherm, P.O. Box 563, Lewiston, N.Y., 14092 and Dow Chemical Company, P.O. Box 1206, Midland, Mich. U.S.A. 48674. Thermal fluids can be conditioned in various fashions to behave more suitably for microdroplet formation and integrity, for example by employing one or more surfactant materials. It is to be expected that the viscosity and interfacial tension (factors in droplet stability, formation, and mechanics) of a thermal fluid will vary at least somewhat with temperature, and in choice of both the thermal fluid and any treatment components (such as surfactants) the range of anticipated temperature extremes that can be expected must be considered to avoid unwanted material breakdowns, phase changes, decompositions, etc.

Electrode Sequencing and Related Droplet Transport Issues

The sequencing of electrode-driven electrical manipulation of droplets is known. Discussion of design issues for droplet transport can be found, for example, in pp. 56-60 of *Adaptive Cooling of Integrated Circuits Using Digital Microfludics* by P. Paik, K. Chakrabarty, and V. Pamula, published by Artech House, Inc., Norwood, Me., Artech House, 2007, ISBN 978-1-59693-138-1.

For cooling applications, it is to be expected that a number of droplets, and perhaps a relatively large number, will be in transport simultaneously. In some implementations or situations it can be advantageous to route droplets continuously according to a predefined pattern that is executed in a periodic fashion. The rate at which the pattern is executed can in some implementations or situations be advantageously varied in time in response to temperature or competing tasks.

In other situations, more complex routing of more arbitrary types of routes, each with associated requirements, can be expected. In some cases, various droplet transport tasks can compete for shared transport paths. Methods for droplet planning and scheduling accordingly can become more complex and in many situations can be optimally designed. Some representative techniques applicable to these situations are taught by K. Bohringer, "Modeling and Controlling Parallel Tasks in Droplet-based Microfluidic Systems," in *Design Automation Methods and Tools for Microfluidics-Based Biochips*, K. Chakabarty, J. Zeng (ed.), Springer, ISBN 1-4020-5122-0, 2006, pp. 301-327

Use of Surface Acoustic Wave Transport instead of Electrode Array Transport

As an alternative or supplement to electrode-driven electrical manipulation of droplets, various embodiments and implementations can advantageously incorporate the use of Surface Acoustic Wave (SAW) droplet transport is known, for example as taught in P. Tabourier, J.-C. Camart, C. Druon, "Surface acoustic wave two-dimensional transport and location of microdroplets using echo signal," *Journal of Applied Physics*, Volume: 100, Issue 11, pp. 116101-116101-3.

Use for Heating, Heating/Cooling, Temperature Equilibrium

As an alternative or supplement to cooling, various embodiments and implementations can advantageously incorporate the aforementioned heat transfer mechanisms in reverse so as to deliver heat from the outside world or other source to one or more target elements, for example to deliver heat to a reaction element or cell culture chamber. Accordingly, the aforementioned heat transfer mechanisms can thus also be used for combined heating and cooling for robust temperature control, exchanging heat between entities to attain thermal equilibrium, etc.

Incorporation of Sensors

Various embodiments and implementations can advantageously incorporate various types of sensors responsive to or interrogating microdroplets, for example temperature sensors, capacitive sensors, optical sensors, bioFET sensors, acoustic wave sensors, electric-field sensors, etc. In some embodiments and implementations the signals provided from such sensors can advantageously used for reporting measurements, feedback control for droplet transport rate modulation, feedback control for droplet transport routing, feedback control for droplet transport task scheduling, feedback control for higher-level task scheduling, and other applications.

Incorporation of Controlled Valves

As an alternative or supplement to electrode-driven electrical manipulation of droplets, various embodiments and implementations can advantageously incorporate the use of microfluidic or other types of controlled valves to direct microdropets, provide controlled access to reservoirs, seal and provide access to reaction chambers, interface with droplet-creation nozzles, as well as other uses.

Closed-Loop Fluidic Routing

Various embodiments and implementations can advantageously incorporate closed-system routing of microdroplets. For example, in a cooling application, microdroplets of thermal fluid can circulate in a cooling arrangement, delivering heat to or from a thermoelectric device.

External-System Fluidic Interfaces

Various embodiments and implementations can advantageously incorporate fluidic interfaces to external systems, external reservoirs, droplet-creation nozzles, etc.

Various embodiments and implementations can advantageously incorporate controlled valves in the input and/or output structure for external system fluidic interfaces.

Additional Layers and other Extended Three-Dimensional Structures

Further, the microfluidic transport system need not be confined to two layers (i.e., a first planar arrangement for transporting microdroplets of fluidic material in two spatial dimensions and second planar arrangement for transporting microdroplets of fluidic material in two spatial dimensions) as described in the examples provided thus far. For example, at least a third planar arrangement for transporting microdroplets of fluidic material in two spatial dimensions can be connected by at least one conduit situated between the first planar arrangement and third planar arrangement, the at least one conduit connecting the first planar arrangement and third planar arrangement and arranged to permit at least one microdroplet of fluidic material to move between the first planar arrangement and third planar arrangement. For example, the system can be arranged so that a microdroplet of fluidic material is transported by the first planar arrangement, then moved through the at least one conduit, and then transported by the third planar arrangement.

As an example, FIG. 40a depicts three planar arrangements for transporting microdroplets of fluidic material in two spatial dimensions (heavier-lined) arranged with openings for interlinking conduits and a connecting section (lighter-lined) providing conduit pathways between these two layers. The conduit pathways can be passive passageways or can comprise electrodes or other transport mechanisms. It is understood that in some embodiments the connecting section can be omitted and the planar arrangements can be directly connected. For the case where the connecting section is employed, FIG. 40b depicts a final assembly of the three example planar microdroplet transport arrangement layers assembled together interleaved with the two example connecting sections presented in FIG. 40a. Again, it is to be understood that in some embodiments the connecting section can be omitted and the planar arrangements can be directly connected.

In such a way, a multiple-level three-dimensional droplet transport arrangement can be implemented, wherein each layer comprises for example a planar arrangement for transporting microdroplets of fluidic material in two spatial dimensions, and the layers are joined by one or more conduits in the manner described extensively above for the two-layer case. FIG. 40c depicts a representation of an example comprising some number of planar microdroplet transport arrangement layers, said number greater than three. Again, it is to be understood that in some embodiments the connecting section can be omitted and the planar arrangements can be directly connected.

In one approach, pairs of planar microdroplet transport arrangement layers are connected strictly pairwise, for example as suggested in FIG. 41a. Alternatively, various embodiments and implementations can advantageously configure, for example, the at least one connecting conduit to be an extension of a conduit used to link a given planar microdroplet transport arrangement layer with another planar microdroplet transport arrangement layers. FIG. 41b depicts an example wherein at least one common extended conduit is used to connect three microdroplet transport arrangement layers. These approaches can be combined, for example as depicted in FIG. 41c. In these, again it is to be understood that in some embodiments the connecting section can be omitted and the planar arrangements can be directly connected.

Using such approaches, a connective topology among three or more microdroplet transport arrangement layers can be implemented. For example, FIG. 42a depicts an arrangement that implements a connective droplet transport topology of at least the linear three-dimension ('cube') lattice depicted in FIG. 42b. As each microdroplet transport arrangement layer can have a rich two-dimensional internal transport capability, the arrangement depicted in FIG. 42a can implement connections among other types of planar lattices. In these, again it is to be understood that in some embodiments the connecting section can be omitted and the planar arrangements can be directly connected.

Further, by incorporating some conduits between adjacent layers and other conduits that pass through adjacent layers in a sealed manner or otherwise bypass fluidic access, connective topologies among the layers can be implemented other than a linear three-dimension ('cube') lattice. For example, a topological ring, torus, hyper-torus, hypercube, and other inter-connective topologies can be realized as advantageous in an implementation or embodiment. As a simple example, FIG. 42c illustrates a group of pairwise conduits that interconnect the microdroplet transport lattices within the three depicted microdroplet transport arrangement layers in a ring topology. In these, again it is to be understood that in some embodiments the connecting section can be omitted and the planar arrangements can be directly connected.

Non-Planar Layers

It is to be understood that various embodiments and implementations can advantageously incorporate non-planar layers in place of one or more of the aforementioned planar layers. For example, a curved layer in the shape of a sphere, hemisphere, ellipsoidal surface, or other arrangement can be used as advantageous in an implementation or embodiment.

Topologically One-Dimensional Layers

It is to be understood that various embodiments and implementations can advantageously incorporate topologically one-dimensional layers in place of one or more of the aforementioned planar layers. For example, a topologically one-dimensional layer in the shape of a linear path, curved path, spiral path, helix, coil, or other arrangement can be used as advantageous in an implementation or embodiment.

Implementation of a Microfluidic Bus

U.S. Pat. No. 8,032,258 and pending U.S. patent application Ser. Nos. 13/251,286 and 13/251,288 teach conduit-based valve-controlled multichannel microfluidic bus technologies for the transport of continuous liquid, gas, and multiphase flows as well as burst transport.

Alternatively or in addition to this, various embodiments and implementations can advantageously be organized as a microfluidic bus, using one or more levels of a three-dimensional microdroplet arrangement as a shared transport bus linking microfluidic subsystems implemented in one or more other levels of the three-dimensional microdroplet arrangement. FIG. 43 depicts an example use of a single microdroplet transport arrangement layer configured to serve as a microfluidic bus in service to four other microdroplet transport arrangement layers. In these, again it is to be understood that in some embodiments the connecting section can be omitted and the planar arrangements can be directly connected.

Example Fabrication

The arrangements and embodiments as described above can be fabricated within a printed circuit board, integrated circuit housing, or using materials such as metal, glass, polymer, plastic, layered materials, fibrous materials, etc. Manufacturing techniques can employ multi-stage assembly and/or functional printing (popularly known as "3D printing").

Adaptations to Chemical, Biochemical, and Other Microfluidic Systems

The arrangements and embodiments as described above can be used for a wide range of applications including microfluidic systems, chemical reactors, biochemical reactors, chemical analysis arrangements, biochemical analysis arrangements, and other apparatus.

For example, a each layer in the three-dimensional microdroplet arrangement can fluidically interface to one or more chemical and/or biochemical reactor elements, one or more chemical and/or biochemical analysis arrangements, one or more cell culture chambers, one or more chemical and/or biochemical sensors, one or more controlled valves, and/or other apparatus within that layer, for example as suggested in FIG. 44a. The resulting layer can be combined with other layers, for example as depicted in FIG. 44b.

Other more specialized arrangements can also be provided. For example, the detailed arrangements provided earlier and variations upon them can be modified so that membrane elements are used in place of the many depicted thermal interface elements, Additionally, the heat transport capabilities described can be used to provide highly localized cooling, heating, temperature regulation, and thermal equilibrium operations to chemical and/or biochemical reactor elements, one or more chemical and/or biochemical analysis arrangements, one or more cell culture chambers, one or more chemical and/or biochemical sensors, etc.

Example Applications

The arrangements and embodiments as described above can be used for a wide range of applications relating to heat transfer, fluidic transfer, and other uses, and can be implemented within a printed circuit board, integrated circuit housing, or using materials such as metal, glass, polymer, plastic, layered materials, fibrous materials, etc. Example applications include integrated circuit cooling, energy harvesting, microfluidic systems, chemical reactors, biochemical reactors, chemical analysis arrangements, biochemical analysis arrangements, and other apparatus.

For example, the arrangements and embodiments as described above can be applied to a wide range of electronic cooling and energy harvesting for heat-producing integrated circuits and other electronic components in computers, particularly in large high-density blade servers and data center environments, as taught in pending U.S. patent application Ser. No. 13/385,411.

As another example, the arrangements and embodiments as described above can be applied to microfluidic chemical processing systems. In such systems it is difficult to localize significant variations in temperature. Some micro-reactor chemical reactions require heat while other micro-reactor chemical reactions give off heat. Various embodiments and implementations can thus be useful in creating localized temperature environments, removing heat of reactions, and harvesting power from heat of reactions.

As yet another example, the arrangements and embodiments as described above can be applied to microfluidic biochemical processing systems. In such systems it is important to localize and precisely control temperature. Some micro-reactor biochemical reactions require heat while other micro-reactor biochemical reactions require heat to be removed. Various embodiments and implementations can thus be useful in creating localized temperature environments, removing heat from reactions, and in some cases even provide harvesting of power from the heat of biochemical reactions.

As a further example, the arrangements and embodiments as described above can be applied to microfluidic bioreactor systems. In such systems it is difficult to localize significant variations in temperature. In such systems it is important to localize and precisely control temperature. Some bioreactor processes require heat while other bioreactor processes require heat to be removed. Various embodiments and implementations can thus be useful in creating localized temperature environments, removing heat from reactions, and in some cases even provide harvesting of power from the heat of bioreactor processes.

CLOSING

The terms "certain embodiments," "an embodiment," "embodiment," "embodiments," "the embodiment," "the embodiments," "one or more embodiments," "some embodiments," and "one embodiment" mean one or more (but not all) embodiments unless expressly specified otherwise. The terms "including," "comprising," "having" and variations thereof mean "including but not limited to," unless expressly specified otherwise. The enumerated listing of items does not imply that any or all of the items are mutually exclusive, unless expressly specified otherwise. The terms "a," "an" and "the" mean "one or more," unless expressly specified otherwise.

The foregoing description, for purpose of explanation, has been described with reference to specific embodiments. However, the illustrative discussions above are not intended to be exhaustive or to limit the implementation to the precise forms disclosed. Many modifications and variations are possible in view of the above teachings. The embodiments were chosen and described in order to best explain the principles of the implementation and its practical applications, to thereby enable others skilled in the art to best utilize the implementation and various embodiments with various modifications as are suited to the particular use contemplated.

While the implementation has been described in detail with reference to disclosed embodiments, various modifications within the scope of the inventive concept will be apparent to those of ordinary skill in this technological field. It is to be appreciated that features described with respect to one embodiment typically can be applied to other embodiments.

The inventive concept can be embodied in other specific forms without departing from the spirit or essential characteristics thereof. The present embodiments are therefore to be considered in all respects as illustrative and not restrictive, the scope of the inventive concept being indicated by the appended claims rather than by the foregoing description, and all changes which come within the meaning and range of equivalency of the claims are therefore intended to be embraced therein.

Although exemplary embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used for all applications. Also, not all limitations need be implemented in methods, systems, and apparatuses including one or more concepts described with relation to the provided embodiments. Therefore, the implementation properly is to be construed with reference to the claims.

The invention claimed is:

1. A microfluidic transport system for transporting microdroplets of fluidic material in three spatial dimensions, the system comprising:
a first planar arrangement for transporting microdroplets of fluidic material in two spatial dimensions, the first planar arrangement comprising a first array of electrodes, the first array of electrodes configured for controlled transport of microdroplets responsive to electric fields created by electrical operation of at least some of the electrodes within the first array of electrodes;
a second planar arrangement for transporting microdroplets of fluidic material in two spatial dimensions, the second planar arrangement comprising a second array of electrodes, the second array of electrodes configured for controlled transport of microdroplets responsive to electric fields created by electrical operation of at least some of the electrodes within the second array of electrodes, and
a first conduit situated between the first planar arrangement and second planar arrangement, the first conduit connecting the first planar arrangement and second planar arrangement and arranged to form at least one 3D micro-droplet transit structure to permit at least one microdroplet of fluidic material to move between the first planar arrangement and second planar arrangement;
wherein at least one of the first and second planar arrangements further comprise an interface to a thermoelectric material,
wherein the system is arranged so that a microdroplet of fluidic material is transported by the first planar arrangement, then moved through the first conduit, and then transported by the second planar arrangement,
wherein said transport is responsive to electric fields created by at least electrical operation of at least some of the electrodes within the first array of electrodes and second array of electrodes.

2. The microfluidic transport system of claim 1, wherein the first conduit further comprises at least one conduit electrode.

3. The microfluidic transport system of claim 2, wherein the microdroplet moves between the first planar arrangement and second planar arrangement responsive in at least part to electrical operation of the conduit electrode.

4. The microfluidic transport system of claim 1, further comprising:

a second conduit situated between the first planar arrangement and second planar arrangement, the second conduit connecting the first planar arrangement and second planar arrangement and arranged to permit at least one microdroplet of fluidic material to move between the first planar arrangement and second planar arrangement;
wherein the system is arranged so that a microdroplet of fluidic material is transported by the second planar arrangement, then moved through the second conduit, and then transported by the first planar arrangement.

5. The microfluidic transport system of claim 4, wherein the second conduit further comprises at least one conduit electrode.

6. The microfluidic transport system of claim 1, further comprising:
at least a third planar arrangement for transporting microdroplets of fluidic material in two spatial dimensions, the third planar arrangement comprising a third array of electrodes, the third array of electrodes configured for controlled transport of microdroplets responsive to electric fields created by electrical operation of at least some of the electrodes within the third array of electrodes, and
at least one conduit situated between the first planar arrangement and third planar arrangement, the at least one conduit connecting the first planar arrangement and third planar arrangement and arranged to permit at least one microdroplet of fluidic material to move between the first planar arrangement and third planar arrangement;
wherein the system is arranged so that a microdroplet of fluidic material is transported by the first planar arrangement, then moved through the at least one conduit, and then transported by the third planar arrangement, and
wherein said transport is responsive to electric fields created by at least electrical operation of at least some of the electrodes within the first array of electrodes and third array of electrodes.

7. The microfluidic transport system of claim 6, wherein the at least one conduit is an extension of the first conduit.

8. The microfluidic transport system of claim 1, wherein the microdroplet comprises a thermofluid.

9. The microfluidic transport system of claim 1, wherein the resulting system provides a heat transfer function by using the microdroplet to carry heat.

10. The microfluidic transport system of claim 1, wherein the first planar arrangement further comprises an interface to a sensor.

11. The microfluidic transport system of claim 1, wherein the second planar arrangement further comprises an interface to a sensor.

12. The microfluidic transport system of claim 1, wherein the resulting system provides fluidic transport in a chemical reaction system.

13. The microfluidic transport system of claim 1, wherein the resulting system provides fluidic transport in a chemical analysis system.

14. The microfluidic transport system of claim 1, wherein the resulting system provides fluidic transport in a biochemical reaction system.

15. The microfluidic transport system of claim 1, wherein the resulting system provides fluidic transport in a biochemical analysis system.

16. The microfluidic transport system of claim 1, wherein the first planar arrangement further comprises an interface to a membrane.

17. The microfluidic transport system of claim 1, wherein the second planar arrangement further comprises an interface to a membrane.

18. The microfluidic transport system of claim 1, wherein the first planar arrangement further comprises an interface to a reaction chamber.

19. The microfluidic transport system of claim 1, wherein the second planar arrangement further comprises an interface to a reaction chamber.

* * * * *